(12) United States Patent
Johnson et al.

(10) Patent No.: US 8,425,516 B2
(45) Date of Patent: Apr. 23, 2013

(54) APPARATUS AND METHOD FOR SCULPTING THE SURFACE OF A JOINT

(75) Inventors: Wesley D. Johnson, Eden Prairie, MN (US); Gerard A. Engh, Alexandria, VA (US); Aaron J. Bisek, Elk River, MN (US); Michael N. Travanty, Minneapolis, MN (US); Robert E. Kohler, Lake Elmo, MN (US); Daryl R. Pilarski, East Bethel, MN (US); Anthony G. Kremer, Becker, MN (US); Kevin D. Swanson, Elk River, MN (US); Kevin T. Stables, Forest Lake, MN (US)

(73) Assignee: Alexandria Research Technologies, Inc., Plymouth, MN (US)

( * ) Notice: Subject to any disclaimer, the term of this patent is extended or adjusted under 35 U.S.C. 154(b) by 349 days.

(21) Appl. No.: 12/594,389

(22) PCT Filed: Apr. 4, 2008

(86) PCT No.: PCT/US2008/059482
§ 371 (c)(1),
(2), (4) Date: Oct. 2, 2009

(87) PCT Pub. No.: WO2008/124633
PCT Pub. Date: Oct. 16, 2008

(65) Prior Publication Data
US 2010/0145343 A1    Jun. 10, 2010

Related U.S. Application Data

(60) Provisional application No. 60/910,131, filed on Apr. 4, 2007.

(51) Int. Cl.
*A61B 17/56* (2006.01)
*A61B 17/00* (2006.01)
*A61B 17/60* (2006.01)

(52) U.S. Cl.
USPC .................. 606/79; 606/90; 606/96

(58) Field of Classification Search .............. 606/85, 606/86 R, 87, 88, 90, 96, 79, 80; 408/69
See application file for complete search history.

(56) References Cited

U.S. PATENT DOCUMENTS

| | | | |
|---|---|---|---|
| 4,808,185 A | 2/1989 | Penenberg et al. | |
| 5,041,119 A * | 8/1991 | Frigg et al. | 606/96 |
| 5,810,828 A * | 9/1998 | Lightman et al. | 606/80 |
| 6,716,249 B2 | 4/2004 | Hyde | |
| 2002/0111690 A1 | 8/2002 | Hyde | |
| 2006/0064100 A1 | 3/2006 | Bertagnoli et al. | |
| 2006/0161045 A1* | 7/2006 | Merril et al. | 600/117 |
| 2006/0241569 A1* | 10/2006 | DiSilvestro | 606/1 |

* cited by examiner

*Primary Examiner* — Kevin T Truong
*Assistant Examiner* — Christian Sevilla
(74) *Attorney, Agent, or Firm* — Barbara A. Wrigley; Oppenheimer Wolff & Donnelly, LLP

(57) ABSTRACT

Methods and devices for sculpting bones, particularly in preparation for implanting prosthetic devices to replace articulating bone joint surfaces. Improved bone removal devices including burr mills driven by gears and loop drives are provided. Reciprocating cutters and belt cutters are also provided. Some devices have either integral or removable expandable portions to vary the force and bone resection depth. Devices can have irrigation ports and plenums to remove bone fragments. Some cutters are dual cutters, adapted to remove bone in two or more regions, such as the knee joint, simultaneously.

23 Claims, 41 Drawing Sheets

Lateral Condyle

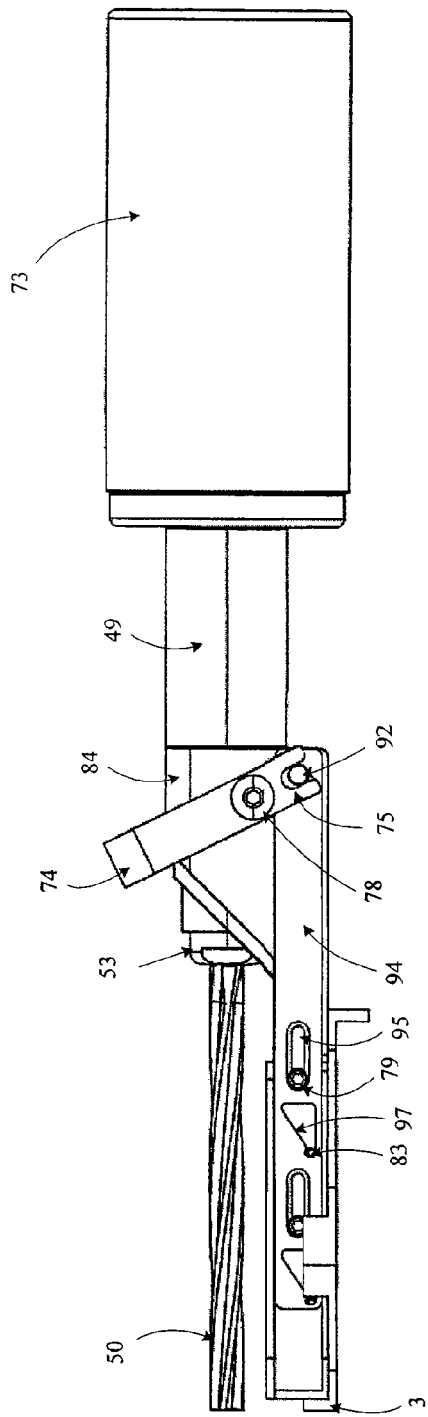
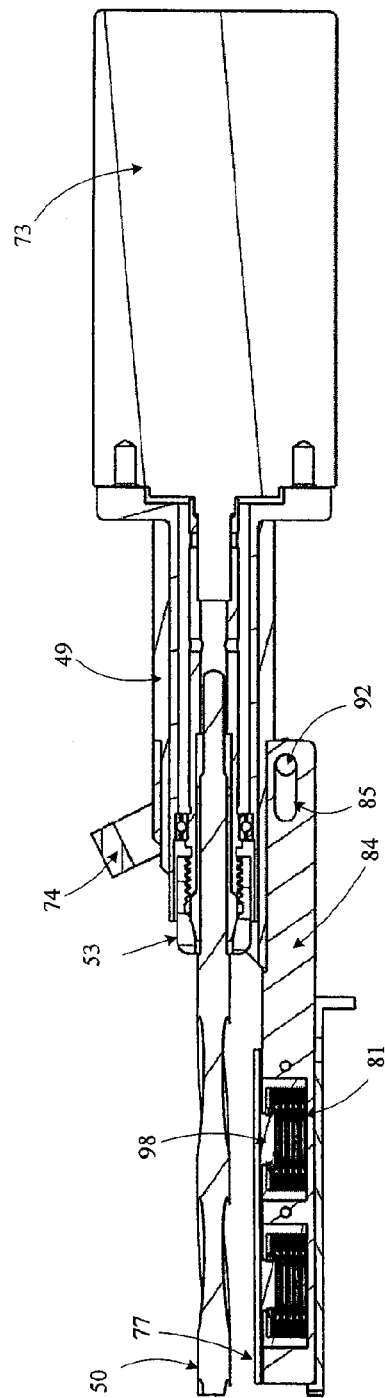
FIG 61
FIG 62

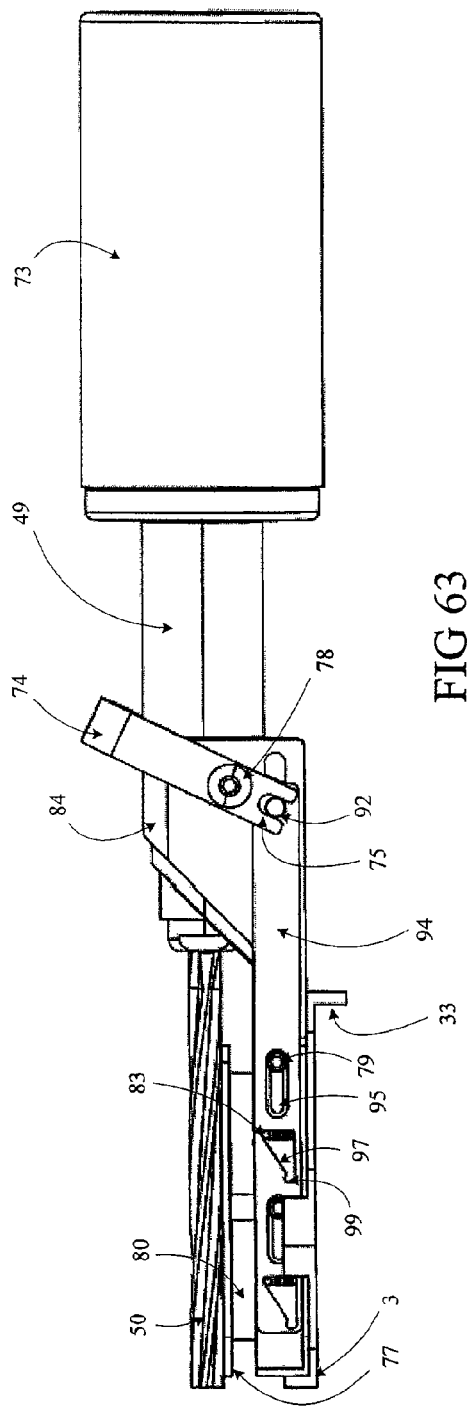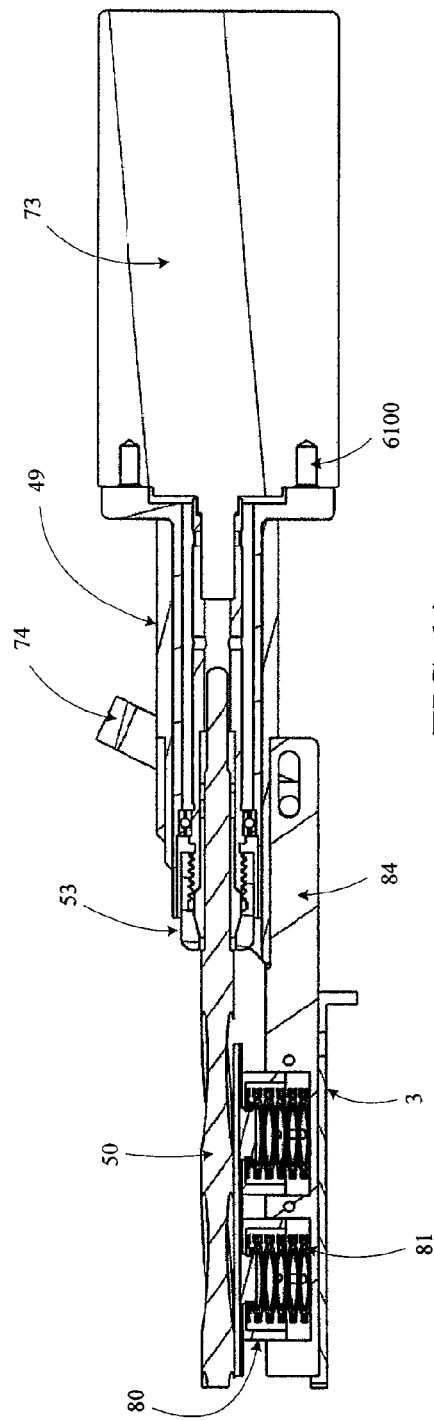
FIG 63
FIG 64

APPARATUS AND METHOD FOR SCULPTING THE SURFACE OF A JOINT

TECHNICAL FIELD

This invention relates to implants and instruments for use in cutting and preparing bone, for example, in total and partial knee arthroplasty. Such instruments are applicable in other total and partial joint replacement surgeries which include, but are not limited to the hip, the shoulder, the ankle, the elbow, the joints of the hand, the joints of the wrist, the joints of the foot and the temporal mandibular joint, articulating joints such as the knee and hip, and also motion segments of the spine.

BACKGROUND OF THE INVENTION

A joint, such as the ankle, knee, hip or shoulder, generally consists of two or more relatively rigid bony structures that maintain a relationship with each other. In the case of the spine, a motion segment generally consists of two vertebral bodies, a disc and two facet joints. Soft tissue structures spanning the bony structures hold the bony structures together and aid in defining the motion of one bony structure relative to the other. In the knee, for example, the bony structures are the femur, tibia and patella. Soft tissue structures spanning the knee joint, such as muscles, ligaments, tendons, menisci, and capsule, provide force, support and stability to facilitate motion of the knee. Muscle and tendon structures spanning the knee joint, as in other joints of the body and in the spine provide dynamics to move the joint in a controlled manner while stabilizing the joint to function in an orderly fashion. The joint is dynamically stabilized by contraction of primary muscles to move the joint in a desired direction combined with antagonistic muscle contraction to direct resultant joint loads within favorable orientation limits relative to the bony structures of the joint. It is believed that proprioceptive feedback provides some of the control or balance between primary and antagonistic muscle contraction.

In an articulating joint, a smooth and resilient surface consisting of articular cartilage covers the bony structures. In the spine, the disc, consisting of an annulus and a nucleus, spans the space between adjacent vertebral bodies and two facet joints provide articulation posteriorly. The articular surfaces of the bony structures work in concert with the soft tissue structures spanning the joint to form a mechanism that defines the envelop of motion between the structures. Within a typical envelop of motion, the bony structures move in a predetermined pattern with respect to one another. When articulated to the limits of soft tissue constraint, the motion defines a total envelop of motion between the bony structures. In the knee, the soft tissue structures spanning the joint tend to stabilize the knee from excessive translation in the joint plane of the tibiofemoral compartments. Such tibiofemoral stability enables the femur and tibia to slide and rotate on one another in an orderly fashion. The motion of the patella relative to the femur in the patellofemoral compartment is related to tibiofemoral motion because the patella is linked at a fixed distance from the tibia by the patellar ligament.

Current methods of preparing a joint to receive implants that replace the articular surfaces or motion segments involve an extensive surgical exposure. In traditional total knee arthroplasty, the surgical exposure, ligament release and sacrifice of the anterior cruciate ligament must be sufficient to permit the introduction of guides that are placed on, in, or attach to the femur, tibia or patella, along with cutting blocks to guide the use of saws, burrs and other milling devices, and other instruments for cutting or removing cartilage and bone to provide a support surface for implants that replace the articular surfaces or motion segment. In traditional unicompartmental knee arthroplasty the surgical exposure may be smaller to enable access to the medial or to the lateral tibiofemoral compartment of the knee. The anterior cruciate ligament is generally preserved. For traditional knee joint replacement, the distal end of the femur may be sculpted to have flat anterior and posterior surfaces generally parallel to the length of the femur, a flat end surface generally normal to the anterior and posterior surfaces, and angled flat surfaces joining the above mentioned surfaces, all for the purpose of receiving a prosthetic device. In general these are referred to as the anterior, posterior, distal and chamfer cuts, respectively. Similarly, in traditional unicompartmental knee joint arthroplasty may be sculpted to have a flat posterior surface generally parallel to the length of the femur, a flat end surface generally normal to the posterior surface, and an angled flat surface joining the above mentioned surfaces, all for the purposes of receiving prosthetic device.

In current knee arthroplasty proper knee alignment is attained by preoperative planning and x-ray templating. Anterior-posterior (A/P) and lateral x-ray views are taken of the knee in full extension. The mechanical axis of the tibia and of the femur is marked on the A/P x-ray. The angle between these lines is the angle of varus/valgus deformity to be corrected. In the A/P view, the angle and depth of the distal femoral resection relative to the femoral mechanical axis, hence the angle of the femoral implant and depth of positioning into the femoral condyle, is predetermined per the surgical technique for a given implant system. Similarly, the angle of the tibial resection relative to the tibial mechanical axis, hence the angle of the tibial implant, is predetermined per the surgical technique for a given implant system. The femoral resection guides are aligned on the femur to position the distal femoral resection relative to the femoral mechanical axis and the tibial resection guides are aligned on the tibia to position the proximal tibial resection relative to the tibial mechanical axis. If the cuts are made accurately, the femoral mechanical axis and the tibial mechanical axis will align in the A/P view. Once the femur and tibia have been resected, the medial and lateral collateral ligaments may be released to balance the knee. Soft tissue balancing is generally done with the knee in full extension. The spacing between the femur and tibia at full extension is used to guide ligament release to attain an appropriate extension gap.

Typically, an appropriate extension gap is evidenced by parallel orientation of the distal femoral resection to the tibial plateau resection and with a gap sufficient to accommodate the femoral and tibial implants for partial or total knee arthroplasty. This approach addresses knee alignment and balancing at full extension. Knee alignment and tissue balance at 90° of flexion is generally left to surgeon judgment and knee alignment and tissue balance throughout the range of motion has not been addressed in the past. In aligning the knee at 90° the surgeon rotates the femoral component about the femoral mechanical axis to a position believed to provide proper tensioning of the ligaments spanning the knee.

Current implants and instruments for joint replacement surgery have numerous limitations. These relate to the invasiveness of the procedure and achieving proper alignment, soft tissue balance and kinematics of the joint with the surgical procedure. Such difficulties are present in all joint replacement surgery. Although the spinal disc is not an articular joint, interest in restoring the kinematic function of a degenerated disc has lead to spinal arthroplasty incorporating metal and/or plastic articulating surfaces. Polymers, including hydrogels and urethanes, have also been used to restore spinal disc function. Such spinal implants are preferably placed via minimally invasive surgical approaches and restore motion and kinematics, hence require accurate alignment and orientation of the implant components one to another. In addition, the kinematics of a spinal motion segment are defined by the combined motion across the disc which is a function of the annulus, nucleus, anterior ligament, posterior ligament, facet joint articulation and muscles spanning the motion segment. A spinal motion segment is the motion between adjacent vertebral bodies.

A difficulty with implanting modular knee implants in which the femur or tibia is resurfaced with multiple components has been achieving a correct relationship between the components. For ease of description, multiple components comprising a component such as a femoral component will be referred to as subcomponents. For example, a modular femoral component may include subcomponents for the trochlea, the lateral femoral condyle and the medial condyle, and reference to a "femoral component" includes subcomponents in the case of a multi-piece femoral component.

In the case of a plurality of subcomponents resurfacing the distal femur or proximal tibia, the orientation and alignment of the subcomponents to each other has largely not been addressed. This may account for the high failure rates in the surgical application of free standing compartmental replacements used individually or in combination. Such compartmental replacements include medial tibiofemoral compartment, lateral tibiofemoral compartment, patellofemoral compartment and combinations thereof. Component malalignment may account for the higher failure rate of uni-compartmental implants relative to total knee implants as demonstrated in some clinical studies. When considering bi-compartmental and tri-compartmental designs, orientation and alignment of subcomponents, as well as components, is critical to avoid accelerated wear with a mal-articulation of the implant.

Surgical instruments available to date have not provided trouble free use in implanting multi-part implants wherein the distal femur, proximal tibia and posterior patella are prepared for precise subcomponent-to-subcomponent and component-to-component orientation and alignment. While current femoral alignment guides aid in orienting femoral resections relative to the femur and current tibial alignment guides aid in orienting tibial resections relative to the tibia, they provide limited positioning or guidance relevant to correct subcomponent-to-subcomponent alignment or orientation. Nor do such alignment guides provide guidance relevant to soft tissue balance (i.e. ligament tension to restore soft tissue balance). Moreover, they provide limited positioning or guidance relevant to correct flexion/extension orientation of the femoral component, to correct axial rotation of the femoral component, nor to correct posterior slope of the tibial component. For the patellofemoral joint, proper tibiofemoral alignment is required to re-establish proper tracking of the patella as defined by the lateral pull of the quadriceps mechanism, the articular surface of the femoral patellar groove and maintaining the tibiofemoral joint line. For optimum knee kinematics, femoral component flexion/extension and external rotation orientation, tibial component posterior slope and ligaments spanning the joint work in concert maintaining soft tissue balance throughout the knee's range of motion.

For patients who require articular surface replacement, including patients whose joints are not so damaged or diseased as to require whole joint replacement, the implant systems available for the knee have unitary tri-compartmental femoral components, unitary tibial components, unitary patellar components and instrumentation that require extensive surgical exposure to perform the procedure.

It would be desirable to provide surgical methods and apparatuses that may be employed to gain surgical access to articulating joint surfaces, to appropriately prepare the bony structures, to provide artificial, e.g., metal, plastic, ceramic, or other suitable material for an articular bearing surface, and to close the surgical site, all without substantial damage or trauma to associated muscles, ligaments or tendons, and without extensive distraction of the joint. To attain this goal, implants and instruments are required to provide a system and method to enable articulating surfaces of the joints to be appropriately sculpted using less or minimally invasive apparatuses and procedures, and to replace the articular surfaces with implants suitable for insertion through small incisions, assembly within the confines of the joint cavity and conforming to prepared bone support surfaces.

BRIEF SUMMARY OF THE INVENTION

The present invention is related to implants and instruments for use in less and minimally invasive total knee replacement surgery. More particularly, this invention relates to instruments for cutting and preparing bone. Such bone cutting instruments are applicable in total and partial knee arthroplasty. In addition, such instruments are applicable in other total and partial joint replacement surgery to include, but not limited to the hip, the shoulder, the ankle, the elbow, the joints of the hand, the joints of the wrist, the joints of the foot and the temporal mandibular joint. Such instruments are also applicable to motion segments of the spine to include, but not limited to the spinal disc and the facet joints. For the purposes of this document, the term joint will be used to refer to articulating joints such as the knee and hip, and also motion segments of the spine.

The present invention provides a system and method for partial or total joint replacement to restore joint kinematics. The instruments and implants disclosed accomplish accurate bone and soft tissue preparation, restoration of anatomical alignment, soft tissue balance, kinematics, component to component orientation and alignment, subcomponent to subcomponent orientation and alignment, and implant fixation through limited surgical exposure.

Proper alignment and positioning of the implant components and subcomponents are enabled by instruments guided by the soft tissue structures of the knee to guide bone resections for patient-specific anatomical alignment and component orientation. The medial and lateral tibial articular surfaces and the patellar articular surface are generally prepared with planar resections. The medial and lateral femoral condyles and trochlea are kinematically prepared. Such instrumentation is referred to as Tissue Guided Surgery (TGS) and is described in U.S. Pat. No. 6,723,102 and is incorporated by reference in its entirety.

Proper alignment of the femoral, tibial and patellar implants requires proper anatomical alignment of the knee joint throughout the range of motion. By using the soft tissue structures spanning the knee to guide bone resection. TGS instrumentation established proper soft tissue balancing throughout the range of motion. TGS knee procedures include, but are not limited to, unicompartmental arthroplasty of the medial or lateral tibiofemoral compartments; bicompartmental arthroplasty of the patellofemoral and either the medial or lateral tibiofemoral compartment or of both tibiofemoral compartments; or tricompartmental arthroplasty of the patellofemoral joint and both tibiofemoral compartments. In such procedures, the knee joint is generally exposed through a small medial patellar incision. The anterior and posterior cruciate ligaments are left intact. Applicants believe that the instrument system will function in cases where the anterior cruciate ligament is partially or completely compromised. In one embodiment of the invention bicompartmental arthroplasty of the medial and lateral tibiofemoral compartments described herein, the medial and lateral tibial articular surfaces are removed with planar resections. Bone scribing instruments are placed on the resected surfaces in the medial and lateral tibiofemoral compartments. Each scribing instrument is extended to load against its respective condyle to score a shallow groove as the knee is flexed and extended. Primary bone sculpting instruments are then placed on the resected surfaces in the medial and lateral tibiofemoral compartments. Each primary sculpting instrument is structured to extend to distract the respective tibiofemoral compartment independent of one or more sculpting elements, such sculpting elements are then advanced into the respective femoral condyle to a depth relative to the resected tibial plateau and the knee is flexed and extended to kinematically prepare a guide surface in the femoral condyles. Secondary bone sculpting instruments are then placed on the resected surfaces in the medial and lateral tibiofemoral compartments. Each secondary sculpting instrument is structured with a guide element slidably receivable by the prepared guide surface in the respective femoral condyle. Each secondary sculpting instrument is structured to extend to distract the respective tibiofemoral compartment with a distraction force applied between the tibial plateau and the femoral guide surface applied through the guide element. In one embodiment, the secondary sculpting instrument is structured with one or more sculpting elements at a fixed distance from the guide element bearing surface such that as the knee is flexed and extended such sculpting elements prepare a surface on the respective femoral condyle at a predetermined distance from the guide surface previously prepared in the femoral condyle by the primary sculpting instrument. In another embodiment, the secondary sculpting instrument is structured with one or more sculpting elements at a variable distance from the guide element bearing surface, such sculpting elements structured to be advanced into the respective condyle to a predetermined depth relative to the guide element bearing surface. Such advancement of cutting elements is done before starting knee flexion and extension to prepare the femoral condyles. Alternatively, such advancement of cutting elements is done as the knee is flexed and extended to prepare the femoral condyles.

Alternatively, the knee can be positioned at specific flexion angles. At each knee flexion angle each primary sculpting instrument is structured to extend to distract the respective tibiofemoral joint independent of one or more sculpting elements. Such sculpting elements are then advanced into the respective femoral condyle to a depth relative to the resected tibial plateau to kinematically prepare a guide surface in the femoral condyles. The knee is then rotated to the next flexion angle and the process repeated. Secondary bone sculpting instruments are then placed on the resected surfaces in the medial and lateral tibiofemoral compartments. Each secondary sculpting instrument is structured with a guide element slidably receivable by the prepared guide surface in the respective femoral condyle. Each secondary sculpting instrument is structured to extend to distract the respective tibiofemoral compartment with a distraction force being applied between the tibial plateau and the femoral guide surface applied through the guide element. The secondary sculpting instrument is structured with one or more sculpting elements at a variable distance from the guide element bearing surface, such sculpting elements structured to be advanced into the respective condyle to a predetermined depth relative to the guide element bearing surface to kinematically prepare an implant support surface. Sculpting is stopped and the knee is rotated to the next flexion angle and the process repeated. Optionally, the sculpting instruments can be structured to prepare a curved, hemi-spherical or contoured surface as may be required to match various support surfaces on a mating unitary femoral implant or a femoral implant structured with a plurality of sub-components.

As the femoral condyles are sculpted by primary sculpting instruments, varus/valgus alignment at full extension is periodically checked. Intracompartmental distraction of the primary sculpting instrument may be biased to the medial or lateral tibiofemoral compartment for valgus or varus correction, respectively. Alternatively, primary sculpting instruments are placed in both medial and lateral tibiofemoral compartments and the respective femoral condyles are prepared simultaneously until appropriate guide surface depth is reached on one condyle. The primary sculpting instrument in this compartment is replaced with a spacer and preparation of the guide surface in the other femoral condyle is continued until anatomical align of the knee is attained. When the femoral mechanical axis and tibial mechanical axis align, the knee is properly aligned. Secondary sculpting instruments are then placed into each tibiofemoral compartment to prepare implant support surfaces in the femoral condyles as described above. Therefore, proper knee alignment and soft tissue balance is attained throughout knee range of motion.

In an alternative technique, each tibiofemoral compartment is prepared independently. The knee joint is exposed as described above. One of the tibiofemoral compartments is prepared first, typically the one with more severe pathology. The respective tibial articular surface is resected as described above. A bone scribing instrument, primary sculpting instrument and secondary sculpting instrument are used as described above to prepare one of the tibiofemoral compartments. Appropriately sized femoral and tibial trials are placed on the prepared bone surfaces and the other tibiofemoral compartment is prepared as described above. In the case of unicompartmental knee arthroplasty, the diseased tibiofemoral compartment is prepared with as described above for the first tibiofemoral compartment to be prepared. In the case of patellofemoral arthroplasty, the patella is resected in a planar resection, a primary sculpting instrument structured to extend to distract the patellofemoral joint independent of one or more sculpting elements, such sculpting elements are then advanced into the femoral trochlear groove to a predetermined depth below the articular surface of the trochlear groove along a path guided by patellofemoral articulation. Advancement of such sculpting elements is done after placing the primary sculpting instrument on the resected patella and before starting to flex and extend the knee. Alternatively, such advancement of sculpting elements is done while the knee is flexed and extended to create the guide surface in the femoral trochlear groove. A secondary bone sculpting instrument is placed on the resected patella. The secondary sculpting instrument structured with a guide element slidably receivable by the prepared guide surface in the trochlea. The secondary sculpting instrument is structured to extend to distract the patellofemoral joint with a distraction force applied between the patella and the trochlear guide surface applied through the guide element. In one embodiment, the secondary sculpting instrument is structured with one or more sculpting elements at a fixed distance from the guide element bearing surface such that as the knee is flexed and extended such sculpting elements prepare a surface on the trochlea at a predetermined distance from the guide surface previously prepared in the trochlea by the primary sculpting instrument. In another embodiment, the secondary sculpting instrument is structured with one or more sculpting elements at a variable distance from the guide element bearing surface, such sculpting elements structured to be advanced into the trochlea to a predetermined depth relative to the guide element bearing surface. Such advancement of cutting elements is done before starting knee flexion and extension to prepare the trochlea. Alternatively, such advancement of cutting elements is done as the knee is flexed and extended to prepare the trochlea. Patellofemoral joint and patellofemoral compartment are interchangeable terms for the patella and femoral trochlea combination.

For bicompartmental and tricompartmental knee arthroplasty involving the patellofemoral joint, one or both tibiofemoral compartments, whichever the case may be, are prepared as described above and trial femoral condylar and tibial components are placed to establish knee kinematics. The patellofemoral compartment is then prepared as described above. Alternatively, the patellofemoral joint is prepared as described above and trial patellar and trochlear components are placed to establish knee kinematics. One or both tibiofemoral compartments, whichever the case may be, are then prepared as described above. Optionally, in the case of tricompartmental knee arthroplasty, the femoral trochlea and both femoral condyles can be prepared at the same time by first resecting the medial and lateral tibial plateaus the patella. Then applying the scribing instruments, primary sculpting instruments and secondary sculpting instruments as described above for the patellofemoral joint and tibiofemoral compartments. Optionally, the sequence for preparing the patellofemoral joint, the medial tibiofemoral compartment and the lateral tibiofemoral compartment can be varied in any order or any combination. Alternatively, the femoral trochlea can be resected with a cutting guide placed on the distal femur or medial to the trochlea. A surgical saw, either oscillating or reciprocating, is placed on or through the cutting guide to resect the femoral trochlea.

Alternatively, the femoral condyles and trochlea are prepared simultaneously. The articular surfaces of the tibia and patella are removed with planar resections. Bone sculpting instruments are placed on the medial and lateral tibial resections and the patellar resection. Bone is resected from the femoral condyles and trochlea as described above. Resection depth is monitored on each condyle and the trochlea. When appropriate depth is reached in one compartment that sculpting instrument is replaced with a spacer and sculpting of remaining surfaces is continued. Once a spacer has been placed into one of the tibiofemoral compartments, resection of the other femoral condyle is continued until desired knee alignment is attained. If resection of both femoral condyles is completed before completion of the trochlear resection, the sculpting instrument in the remaining tibiofemoral compartment is replaced with a spacer and sculpting of the trochlea is continued to the appropriate depth.

Femoral, tibial and patellar bone resections attained with TGG instrumentation are properly positioned and orientated for anatomic knee alignment, soft tissue balance and kinematic function throughout knee range of motion. Using these bone support surfaces to position and orientate the femoral, tibial and patellar components, respectively, will maintain anatomic knee alignment, soft tissue balance and kinematic function. In general, the tibial and patellar resections are planar, making placement of the corresponding implant components, which have planar support surfaces, straight forward. The femoral resections are not planar, and the relative position of the lateral condyle, the medial condyle, and the trochlear resections to one another is a function knee kinematics for a given patient. Therefore, the femoral implant should accommodate this variability.

In an alternative embodiment surgical navigation is used in conjunction with TGS instrumentation to kinematically prepare the femur, tibia and patella to support knee implant components. Surgical navigation technologies applicable to this approach include, but are not limited to, image and image free navigation systems and Hall Effect based navigation systems. The knee joint is exposed as described above. Navigational trackers are attached to the femur, tibia and patella. If a tracker cannot be attached to the patella, then tracking of the patella is done periodically or at discrete points during the procedure with a tracking stylus. Pre-operative alignment and kinematics of the knee are measured per the protocol for the navigation system being used. The tibial plateau and patella are prepared as described above. Alternatively, the navigation system is used to position tibial resection guides for resection of the medial and lateral tibial articular surfaces. The navigation system may be used to align a patellar resection guide for resection of the patella. The anterior and posterior cruciate ligaments are left intact. Primary and secondary bone sculpting instruments are applied as described above as the navigation system monitors and displays femoral resection depths for the primary sculpting instruments in the patellofemoral joint and each tibiofemoral compartment throughout the range of motion while monitoring knee alignment and kinematics. The navigation system indicates when appropriate resection depth is attained on a given femoral articular surface and signals the surgeon to replace that sculpting instrument with trial implants. Femoral resection is continued until the navigation system indicates that desired knee alignment is attained. The surgical navigation system monitors trochlear resection depth and notifies the surgeon when the desired depth is attained. If appropriate trochlear resection depth is attained before completing femoral condylar resection, then trial implants can be placed in the patellofemoral compartment and femoral condylar resection continued. This technique describes using surgical navigation in conjunction with TGS instrumentation to prepare the three compartments of the knee simultaneously. In addition, surgical navigation can be used in conjunction with TGS instrumentation to prepare the knee compartments in the sequences and combinations previously described.

The sculpting instruments in the TGS instrumentation can be instrumented with sensors to measure intracompartmental distraction force and/or distraction distance. Such instrumentation enables monitoring of soft tissue balance during primary sculpting throughout the full range of motion. Force and/or displacement sensors can be attached to the ligaments spanning the knee as complementary measurements of soft tissue balance, distraction force and/or distraction displacement. Instrumented sculpting instruments also enable monitoring resection depth during primary sculpting and/or secondary sculpting throughout the full range of motion. Load cells are placed in a primary and/or secondary sculpting instrument to measure distraction force. Alternatively, if hydraulic pressure is used to extend the primary or secondary sculpting instrument, then pressure sensors are used to measure distraction force by multiplying pressure applied by the cross sectional area of the hydraulic actuator or bladder or balloon. Displacement sensors are placed in primary or secondary sculpting instruments to measure distraction distance. Alternatively, if hydraulics pressure is used to extend the sculpting instrument, then change in volume of fluid delivered to the hydraulic actuator or bladder or balloon by calibrating the distraction device for displacement vs. volume change. Distraction load and distraction displacement readout can be provided by digital readouts, bar graph or other graphical display. The readout can also be displayed in a surgical navigation system display. Such instrumented sculpting instruments can be used with each of the procedures and embodiments described above. Pressure to the hydraulic actuator or bladder may be provided by a syringe pump, or by a pre-charged compliant bladder designed to maintain a relatively constant pressure in the fluid over a workable change in volume required to activate the actuators or bladders used to distract the joint. Alternately, the distraction force can be applied by threaded mechanisms, inclined ramps, scissors mechanisms or other mechanical means.

In a more sophisticated embodiment TGS instrumentation is integrated with surgical navigation, intracompartmental distraction and displacement sensors, and programmable controllers to provide simultaneous closed loop control of the femoral resections. This application specific robotic system sculpts the femoral condyles and trochlea with primary sculpting instruments while the surgeon flexes and extends the knee. The knee joint is access as previously described. A surgical navigation system and navigation trackers are applied as previously described and pre-operative alignment and knee kinematics are measured and archived. The tibia and patella are resected as previously described. Hydraulically extended primary sculpting instruments with integral distraction force and distraction displacement sensors are placed into the three compartments of the knee. The primary sculpting instruments are applied as described above to prepare the respective femoral articular surface. Intracompartmental distraction force in each compartment can be controlled by independent closed loop controllers with distraction force as the feedback. Alternatively, distraction displacement is used for the closed loop feedback for one or more of the sculpting instruments. The robotic TGS instrument system applies a preliminary intracompartmental distraction force to the medial and lateral tibiofemoral compartments and to the patellofemoral compartment, and indicates to the surgeon that the system is ready to start femoral resection. The surgeon repeatedly flexes and extends the knee while the robotic TGS instrument system monitors primary sculpting instrument resection depth, knee alignment and knee kinematics throughout the full range of motion. The robotic TGS instrument system monitors such resection depth in each compartment to assess completion of primary sculpting in a specific compartment, at which point the system prompts the surgeon to replace that sculpting instrument with trial implants. The system then monitors knee alignment while the surgeon continues to flex and extend the knee until the navigation system indicates desired knee alignment is attained. Replacement of the patellofemoral primary sculpting instrument with a spacer is prompted by the system when a preset trochlear resection depth is attained which may occur before or after completion of condyle resections.

Although the application of the TGS instrumentation system to the knee is described in detail herein, it is clear that the TGS instrumentation system is applicable to other total joint arthroplasty and to spinal arthroplasty is a similar manner. The combination of TGS instrumentations with navigation and with closed loop control and robotics can have application in other joint and spinal arthroplasty applications.

The present invention includes methods for sculpting the articular surface of a first bone that normally articulates in a predetermined manner with a second bone. One method includes fixing one or more primary bone sculpting instruments or tools to the second bone, applying a distraction force between the two bones independent of the bone sculpting elements, sculpting a guide surface into the first bone by advancing one or more bone sculpting elements into the first bone and articulating the bones with respect to each other, fixing one or more secondary bone sculpting instruments to the second bone, slidably receiving the guide element of the secondary bone sculpting instrument in the guide surface in the first bone, applying a distraction force between the secondary bone sculpting instrument and the second bone, advancing one or more bone sculpting elements to a predetermined depth relative to the guide element, and sculpting an implant support surface into the second bone by articulating the bones with respect to each other. Optionally, sculpting the articular surface of the first bone by positioning a second bone at a specific orientation to the first bone, fixing one or more primary bone sculpting instruments to the second bone, applying a distraction force between the first and second bones independent of the bone sculpting elements, sculpting a guide surface into the first bone by advancing one or more bone sculpting elements into the first bone and articulating the bones with respect to each other, fixing one or more secondary bone sculpting instruments to the second bone, slidably receiving the guide element of the secondary bone sculpting instrument in the guide surface in the first bone, applying a distraction force between the secondary bone sculpting instrument and the second bone, advancing one or more bone sculpting elements to a predetermined depth relative to the guide element to prepare an implant support surface in the first bone. The second bone is oriented to another position relative to the first bone and the process is repeated to provide another implant support surface in the first bone.

Another method includes fixing one or more bone-sculpting tools to the second bone, sculpting the articular surface of the first bone by articulating the bones with respect to each other, and applying a distracting force between the bone-sculpting tool and the second bone. Optionally, sculpting the articular surface of the first bone by positioning one of the bones with respect to the other, and applying a distracting force between the bone-sculpting tool and the second bone. The distracting force is applied so as to tension the soft tissue structures spanning the knee and force the bone-sculpting tool into the first bone, in which the force applying is operated at least in part under load control. An alternative method includes fixing one or more bone-sculpting tools to the second bone, sculpting the articular surface of the first bone by articulating or positioning one of the bones with respect of the other, and applying a first distraction force between the tibia and femur so as to tension the soft tissue structures spanning the knee. With the first distraction force applied, a second distraction force, independent of the first distraction force, is applied between the bone-sculpting tool and the second bone so as to force the bone-sculpting tool into the first bone. The first distraction force is operated at least in part under load control. The second distraction force is operated at least in part under load control as material is removed from the femur, said material removal continuing until bone-sculpting tool advances to a desired orientation and position relative to the second bone.

In some methods, applying the distracting force includes applying a fluid under pressure, in which the load control includes controlling the fluid pressure. Controlling the fluid pressure can include controlling a gaseous fluid pressure or a liquid fluid pressure, in various embodiments. The method may include measuring the load between the two bones and controlling the distracting force at least in part as a function of the measured load. In some methods, the force applying is controlled under load control, followed by displacement control after a displacement limit is reached. The displacement control can include mechanically limiting the range of displacement.

In some such methods, the load control is at least in part performed by an automatic controller which automatically controls the distraction force at least in part as a function of the load. The load control may be at least in part performed under manual control, in which a human controls the distraction force at least in part in response to a load read-out value.

Some embodiments utilize barrel cutters. One apparatus includes a frame having a space within, an outside region without, and a plurality of cutting cylinders rotatably disposed within the frame. A drive member can be externally accessible from outside of the frame, and the drive member operably coupled to rotate the cutting cylinders. In some embodiments, the housing has a posterior region for inserting into a mammalian body, an anterior region opposite the posterior region, a right side and a left side both extending between the posterior and anterior regions, in which the drive member is a shaft which protrudes outside of the housing through the right and/or left sides.

In some barrel cutter embodiments, the drive member is operably coupled to the cutting cylinders through gears. In others, the drive member is operably coupled to the cutting cylinders through a flexible drive loop. In others, the drive member is operably coupled to the cutting cylinders through connecting arms. Some embodiments also include a fluid inlet port and outlet port in fluid communication with the housing interior for providing irrigation and tissue debris removal. Embodiments may also include a plurality of nested telescoping platforms, the platforms having an interior, an extended configuration and a collapsed configuration, in which the platforms can be urged from the collapsed configuration to the extended configuration through direct or indirect application of fluid pressure to the platforms interior. Some embodiments include two barrel cutter device coupled side by side in substantially the same plane, and which may be coupled to transfer applied torque between the first and second devices. In some embodiments two barrel cutters may be powered independently.

The present invention also provides belt cutter embodiments. One apparatus includes a frame having a posterior region for inserting into a mammalian body, an anterior region opposite the posterior region, a posterior roller rotatably coupled to the frame posterior region, an anterior roller rotatably coupled to the frame anterior region, and a cutting belt looped around both the posterior and anterior rollers. The apparatus can further include a drive member operably coupled to the anterior roller to rotatably drive the anterior roller and cutting belt.

In some belt cutters, the cutting belt includes a plurality of apertures therethrough, where which the apertures may optionally have a raised trailing edge. Some embodiments also include a posterior tissue protector coupled to the frame to protect tissue from the cutting belt posterior region. The belt cutter may have an anterior frame member coupled to the frame anterior portion. The drive member may be externally accessible from outside the frame, with the drive member disposed along an anterior-posterior axis, or disposed perpendicular to an anterior-posterior axis, in various embodiments.

Some belt cutter apparatus further include a housing base operably coupled to the frame for protecting tissue from a bottom portion of the cutting belt. A tensioning arm can be operably coupled to the anterior and posterior roller for adjusting belt tension in some embodiments.

Some embodiment cutting belts have a longitudinal axis, a substantially planar surface, and a plurality of outer cutting ridges disposed on the belt outer surface. The belt may have a plurality of inner ridges disposed on the belt inner surface. The ridges are oriented substantially perpendicular to the belt longitudinal axis in some embodiments, and are oriented at between about a 20 and a 70 degree angle with respect to the longitudinal axis in other embodiments. The belt may have a first set of substantially parallel cutting ridges on the belt outer surface, and a second set of substantially parallel cutting ridges on the belt outer surface, in which the first and second set of ridges cross each other to form a diamond shape pattern. In some belts, a first set of substantially parallel ridges are disposed on the belt outer surface, a second set of substantially parallel ridges are disposed on the belt outer surface, where the first and second set of ridges are disposed at least a 20 degree angle with respect to each other. Cutting belts can be tensioned and supported on rollers. A posterior tissue protector is present in some embodiment devices. Some cutting belts have a hole trailing edge that forms a grater. One cutting belt has a cutting pattern with alternating, opposing, inclined ridges partially spanning the belt. Cutting teeth can be directed anteriorly in direction of belt movement (i.e. the belt is rotating so as the superior surface is moving generally in an anterior direction) to urge the femur in an anterior direction while cutting.

The present invention also provides various reciprocating cutter embodiments. One such embodiment includes a frame having a posterior region for inserting into a mammalian body, an anterior region opposite the posterior region, and a substantially planar upper cutting element having a cutting surface. The apparatus also includes a drive member operably coupled to the cutter element so as to drive the cutting element to move substantially within a plane, in which the drive member is accessible from outside of the frame. In some embodiments, the drive member operable coupling is through an offset or eccentric cam. Some drive members are disposed along an anterior-posterior axis, while others are disposed orthogonal to an anterior-posterior axis, in various embodiments. Some embodiments include at least 2 upper cutting elements, each configured to operate in substantially the same plane.

In some reciprocating cutters, the upper cutting element cuts primarily only when moved in one direction, but not the opposite direction. In others, the upper cutting element out when moved in one direction and also in the opposite direction. Some embodiments have adjacent sub-components or sub-cutting elements 180° out of phase to each other. Some embodiments have two or more sub-cutting elements; some have four to six.

The present invention also provides an expandable apparatus for cutting into mammalian bone, where the apparatus can include a frame having a posterior region for inserting into a mammalian body, an anterior region opposite the posterior region, and at least one upper cutting element having a cutting surface. The apparatus also includes an extendable body operably coupled to the bottom portion, the extendable body having a first configuration, and a second configuration, in which the apparatus has a greater height in the second configuration than in the first configuration.

In some embodiments, the extendable body is directly coupled to the housing, while in others the extendable body is at least partially received within the housing. Some extendable bodies include a bellows. The bellows can include inward and/or outward folds. The extendable body may include a balloon or bladder received within an expandable housing having a rigid top and bottom and side panels having inward and/or outward folds. The bladder can be formed of polyethylene terephthalate (PET), nylon, polyethylene (PE), urethane, or other materials. The extendable body may include at least one leg received into the housing. The extendable body can include an expandable envelope, which may be nested within another structure. Some embodiments include at least two nested structures, one at least partially nested within the other. The nested structures can include nested, telescoping structures. The cutting element having the extendable body can include a cutting element selected from the group consisting of cutting cylinders, cutting belts, and reciprocating cutting planar surfaces.

A shaver cartridge apparatus is also provided by the present invention. The apparatus can include a frame having a posterior region for inserting into a mammalian body, an anterior region opposite the posterior region, and a removable cartridge. The removable cartridge can have an upper surface bearing a plurality of cutting elements, with the cartridge slidably coupled to the frame to allow for movement of the cutting elements with respect to the frame, and a drive member operably coupled to the cartridge so as to reciprocatingly drive the cartridge, where the drive member is accessible from outside of the frame. In some embodiments, the drive member is rotatably coupled to an off-center cam, where the off-center cam reciprocatingly drives the removable cartridge. The apparatus can have a protected, non-cutting posterior end region for protecting tissue.

The present invention also provides an apparatus for simultaneously cutting into two or more distinct regions of mammalian bone. The apparatus can include a first frame having a posterior region for inserting into a mammalian body and an anterior region opposite the posterior region, and a second frame having a posterior region for inserting into a mammalian body and an anterior region opposite the posterior region. The first and second frames can have a first and second respective moveable cutting body including an upper cutting surface capable of cutting into tissue and bone. The apparatus can include a first drive member operably coupled to the first cutting body, a second drive member operably coupled to the second cutting body, and at least one connecting member for maintaining the first and second frames in spaced apart relation to each other.

In some embodiments, the first and second moveable cutting bodies are each a rotating cylinder having cutting surfaces, while in other embodiments the first and second moveable cutting bodies are reciprocating cutting surfaces each bearing cutting elements. In still other embodiments, the first and second moveable cutting bodies are each closed loop belts bearing cutting elements, wherein the belts are driven by the drive members to move in a longitudinal direction.

Various other aspects are provided by the present invention, in various embodiments. Some devices are driven by a flexible drive belt that is a continuous loop. Some cutting surfaces have cutting teeth or abrasive material. Some cutters can expand in height using telescoping platforms. Guide posts may be used in some embodiments. The height expansion can be accomplished with a mechanical cam, screw mechanism, scissors jack, or a bladder. This may be via hydraulics in a bladder or in a piston/cylinder, via mechanical scissors, via mechanical cam, or via a spacer or shim. A stand alone telescoping or otherwise extendable section is used in some embodiments, which can be placed below or within a cutter body. In some embodiments of the present invention expand in height independent of the position of moveable cutting bodies with the moveable cutting bodies position relative to the expandable housing adjustable by height expansion mechanisms described above.

The present invention also provides an apparatus for cutting into two or more distinct regions of mammalian bone. The apparatus can include an expandable apparatus for cutting into mammalian bone, where the apparatus can include a frame having a posterior region for inserting into a mammalian body, an anterior region opposite the posterior region, and at least one upper cutting element having a cutting surface, and a standalone telescoping or otherwise extendable apparatus having a posterior region for inserting into a mammalian body, an anterior region opposite the posterior region, and at least one extendable body. The cutting apparatus is placed in a first distinct region of mammalian bone. The telescoping section is placed in a second distinct region of mammalian bone. The apparatus can include a drive member operably coupled to the cutting apparatus, and optionally at least one connecting member for maintaining the cutting apparatus in spaced apart relation to the telescoping apparatus. In some embodiments, the telescoping section includes one or more extendable bodies. The telescoping section can have an extendable body directly coupled to the housing, while in others the extendable body is at least partially received within the housing. The extendable body having a first configuration, and a second configuration, in which the apparatus has a greater height in the second configuration than in the first configuration. In one embodiment at least one cutting element moves along with the extendable body. In another embodiment at least one cutting element is stationary with the base housing with the extendable body moving independently of at least one cutting element.

Some cutters are made primarily from stainless steel. The frame and housing can be made of suitable plastics, such as Polyetheretherketone (PEEK).

Unless otherwise noted, some embodiments of the barrel cutter, reciprocating, and belt cutter devices according to the present invention can have a frame length of between about 10 mm and 90 mm, and a width of between about 10 mm and 50 mm. Others have a frame length of between about 10 mm and 90 mm, and a width of between about 40 mm and 100 mm. Still others may have a frame length of less than about 10 cm and a width of less than 10 cm. Yet others may have a frame length of less than about 2 cm and a width of less than about 1 cm.

Unless otherwise noted, some embodiments of the barrel cutter, reciprocating, and belt cutter devices according to the present invention can be used by operating two or more cutters at the same time. One cutter can be placed in the medial tibiofemoral compartment and one placed in the lateral tibiofemoral compartment. One cutter may be placed in the patellofemoral compartment as well. Any combination of these may be used. The cutters may have a common drive member, or they may have individual drive members. They can be distracted independently, or be distracted (i.e. deployed) as a set. They can be distracted with at least one cutting element maintaining a constant distance from the base of the cutter, or be distracted with at least one cutting element maintaining a constant distance from the leading surface of the extendable housing of the cutter. Each may be deployed under "load" control or under "displacement" control, or a combination thereof. Each may be initially deployed under "load" control, then changed to "displacement" control, or visa versa. As they deploy, the frame may constrain the cutting elements in a plane parallel to the base of the frame, or allow the plane of the cutting elements to angulate relative to the base of the frame. The frame may be integral with the base of the cutter or it may be integral with the extendable housing of the cutter.

Surgical Procedure

The surgical procedure involves exposing the diseased tibiofemoral compartment through a small, vertical incision without disrupting muscle structure, or everting or dislocating the patella. The diseased tibial plateau is removed with a conventional tibial resection guide and oscillating and/or sagittal bone saw(s). A primary femoral cutter, referred to as a primary sculpting instrument herein, is placed onto the resected tibial plateau and vertically expanded under load control to tension the joint space. The cutting elements, referred to as sculpting elements herein, are then activated and advanced into the femoral condyle while the surgeon flexes and extends the knee. As the knee joint is flexed the cutter appropriately cuts the articular surface of the femur in a manner that is dependent upon the individual physiology of the patient's knee as established by the patient's cruciate and collateral ligaments, patellar tendon, and soft tissue structures spanning the knee joint. The cutter expands to a height greater than the combined thickness of the intended tibial and femoral implants. As a result, a guide surface (referred to as "SGG" or "groove" in US Provisional Application add number) is created in the femoral condyle; the ceiling of which represents a kinematically correct reference position for the femoral implant. The primary sculpting instrument is removed and replaced with a secondary femoral cutter, referred to as a secondary sculpting instrument herein. Sculpting of the remaining femoral condyle by the secondary sculpting instrument is guided by this groove.

The secondary sculpting instrument is structured to distract the joint space thereby providing alignment, stability and uniform kinematic motion as a function of the cruciate and collateral ligaments. Distraction is provided by a telescoping between the base of the cutter and the resected tibial plateau. The Guide Bar, referred to as a guide element herein, rests against the ceiling of the prepared guide surface. Bone is removed from the condyle on either side of the guide surface to a predetermined depth below the ceiling of the groove, which is the guide surface, previously prepared in the femoral condyle. The result is a kinematically prepared bony support surface for the condylar implant that allows for the combined thickness of the femoral and tibial implants within the joint space. A partial depth of the guide surface remains to expose trabecular bone for bone cement interdigitation and space for a sagittal fin on the condylar component for cement fixation.

BRIEF DESCRIPTION OF THE DRAWINGS

FIG. 61 is a side view of the primary sculpting instrument of FIG. 59 showing the distraction platform collapsed.

FIG. 62 is a cross sectional view of the parallel distractor of FIG. 61 taken through a mid-section showing the distraction platform in a collapsed position and the springs providing distraction force.

FIG. 63 is a side view of the primary sculpting instrument of FIG. 59 showing the distraction platform extended.

FIG. 64 is a cross sectional view of the parallel distractor, motor and tibial trial base of FIG. 63 taken through a mid-section showing the distraction platform in an extended position and the springs providing distraction force.

DETAILED DESCRIPTION OF THE INVENTION

Some embodiments of the invention include replacing the articulating surfaces of the knee with implants. Supporting information is included in current patents and patent applications, to include U.S. Pat. No. 6,482,209 and U.S. Pat. No. 6,723,102, herein incorporated by reference.

The present application includes disclosure of bone scribing instruments, primary sculpting instruments and secondary sculpting instruments for preparing the femoral condyles and trochlea. Various embodiments of each are presented. Sculpting instruments, sculpting instrumentation, sculpting devices, sculpting apparatus and bone-sculpting tools are interchangeable terms. It should be noted that tissue guided surgery and the sculpting device embodiments are applicable to other joints in the body, to include but not limited to the hip, shoulder, ankle; and motion segments of the spine, to include the disc and facet joints. The femoral cutter (sculpting devices) described herein include a shaver (as initially described in U.S. Pat. No. 6,428,209), a barrel cutter, a reciprocating cutter and a belt cutter. Various embodiments of each are presented.

Figure 1:
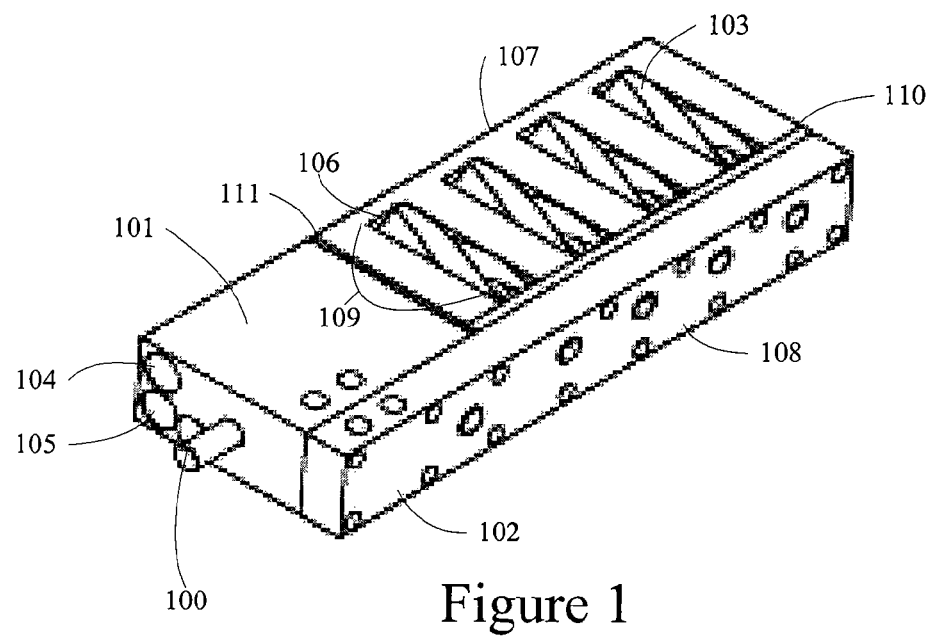
FIG. 1 is a perspective view of a barrel cutter having transversely mounted rotatable cylindrical cutting elements, irrigation ports, and a drive shaft.
Figure 12:
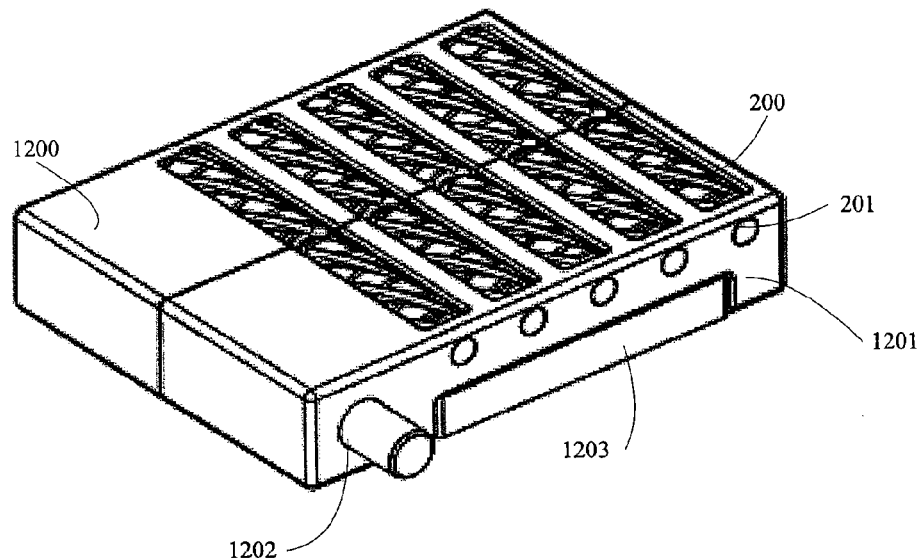
FIG. 12 is a perspective view of a string driven barrel cutter having a bottom telescoping platform, a side drive shaft, and which can use the cutter element of FIG. 2.

FIG. 1 illustrates a barrel cutter designed with multiple cylindrical cutting elements 103. The barrel cutter can be designed with one or more cutting elements 103. In one embodiment the barrel cutter is designed with five cutting elements 200 (as shown in FIG. 12).

The area of contact between the bony surfaces of the tibiofemoral and patellofemoral compartments moves along the surface of the femur, within each compartment, as the knee flexes and extends. This movement is greater on the lateral side due to rotation of the tibia. Hence, it is desirable to have a cutting surface sized to remove bone as the location of the contact area moves over the surface of the femur. In one embodiment the cutting elements 103 are small in diameter and spaced closely together. The overall cutting surface area as shown in FIG. 1 has a cutting surface length 108, a cutting surface width 109, and is sized to accommodate the movement of the medial or lateral tibiofemoral contact area during knee flexion and extension and the width of the medial or lateral femoral condyle. In general, in some embodiments, the cutting surface length may range from approximately 10 mm to 90 mm and the cutting surface width may range from 10 mm to 50 mm, for cutters designed to be placed in either tibiofemoral compartment. In another embodiment in which the tibial plateau is resected, the cutting surface width matches that of the mediolateral width of the distal femur, which may range from approximately 40 mm to 100 mm.

FIGS. 1, 6, 7, 8, 9 and 10, illustrate one embodiment of a barrel cutter, in which the cutting elements 103 are supported by a cutter housing 107 and a side plate 102. Cutter housing 107 is separated from drive housing 101 by spacer plate 111, and from side plate 102 by spacer plate 110. Side plate 102 can be secured using fasteners 1000 (shown in FIG. 10). Side plate 102 can also include top attachment holes 900 (shown in FIG. 9). Optionally, two barrel cutters can be used simultaneously to prepare the medial and lateral femoral condyles. In a left knee the shown barrel cutter is placed in the medial tibiofemoral compartment. A barrel cutter (not shown) structured as the mirror image of the barrel cutter shown is placed in the lateral tibiofemoral compartment. Each barrel cutter structured with four attachment holes 900 to which a cross bar (not shown) can be attached with threaded fasteners (not shown) to stabilize and orient one barrel cutter to the other. Alternatively, each barrel cutter can be placed in respective tibiofemoral compartments independently without connecting them together.

Figure 7:
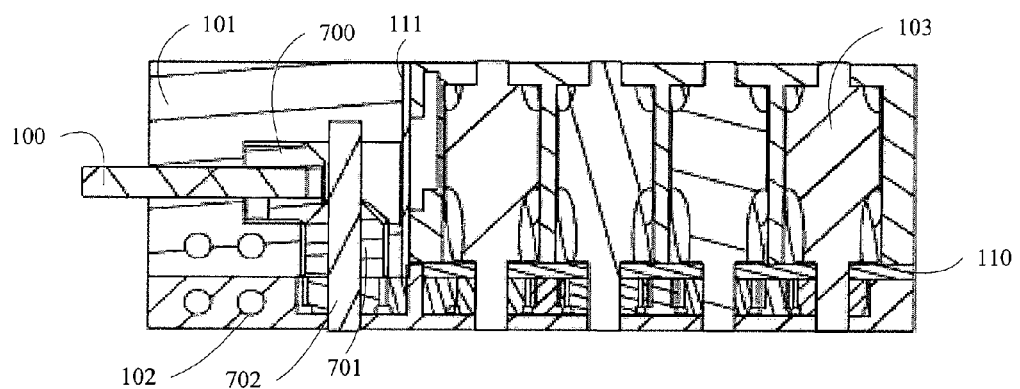
FIG. 7 is a top, cross-sectional view, taken through the cutting element centers, of the barrel cutter of FIG. 1, showing the bevel gear drive for driving the barrel cutters.
Figure 8:
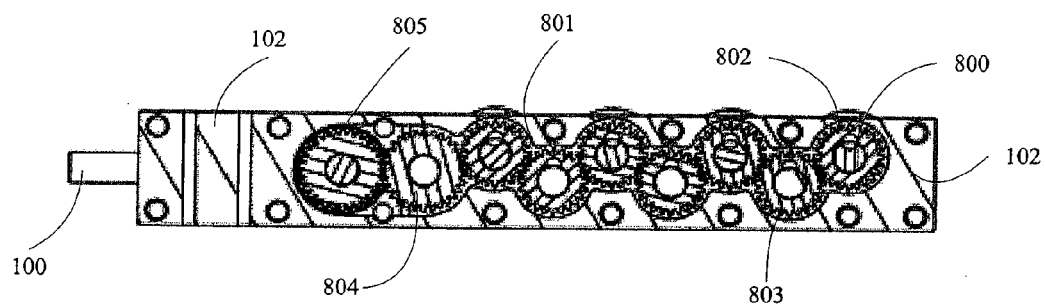
FIG. 8 is a side, cross-sectional view, taken though the drive gears, of the barrel cutter of FIG. 1, showing the end driven cutter elements and gear drive train.
Figure 9:
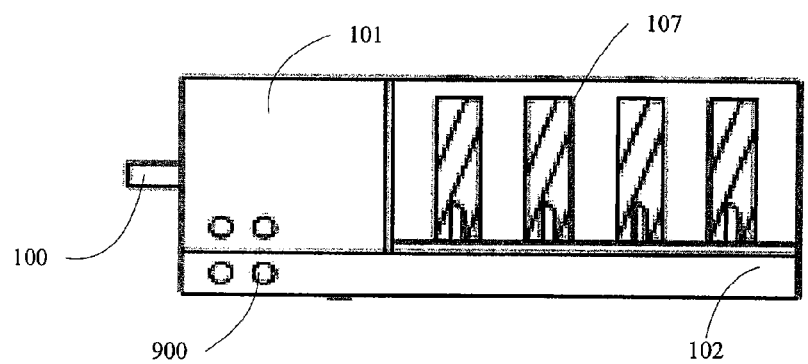
FIG. 9 is a top, schematic view of the barrel cutter of FIG. 1.
Figure 10:
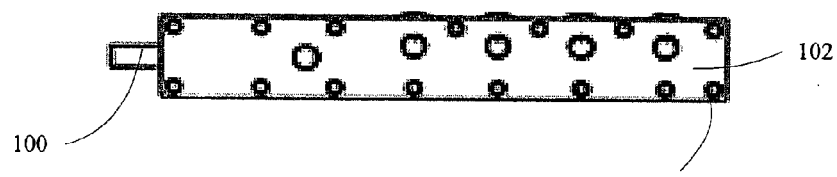
FIG. 10 is a side, elevation view of the barrel cutter of FIG. 1.
Figure 11:
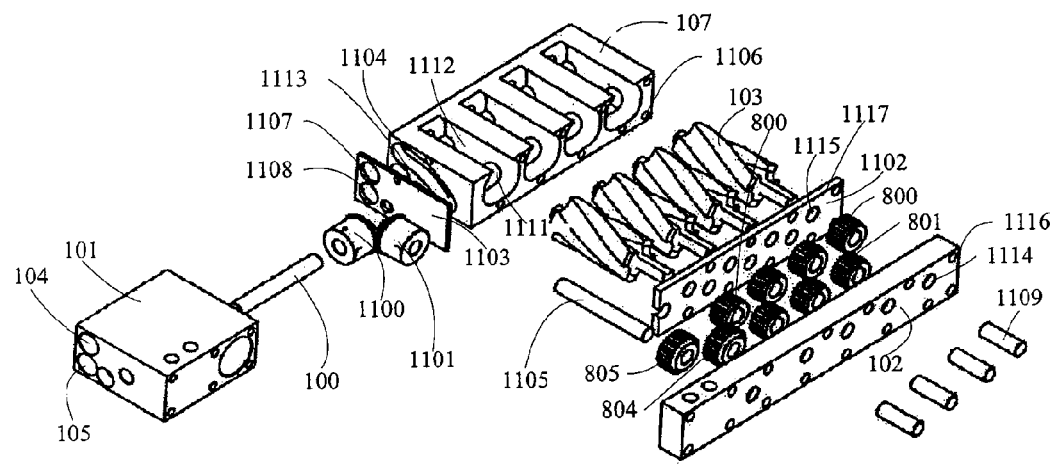
FIG. 11 is an exploded view of the barrel cutter of FIG. 1.

The drive housing 101 supports a drive shaft 100. A rigid or flexible drive shaft extension (not shown) can be attached between the drive shaft 100 and a rotational power supply, such as a surgical power drill or a motor. FIG. 7 illustrates how input torque can be delivered to drive shaft 100 which is attached to a bevel gear set 700 and 701 (or bevel gears 1100 and 1101 in FIG. 11). FIG. 8 illustrates how torque is transferred to drive gear 805 by shaft 702. From the cutter drive gear 800, torque is transferred to a transfer gear 804 to a cutter drive gear 800. Idler gears 803 are placed between subsequent cutter drive gears 800 to transfer torque to each of the cutting elements 103. A lock pin 802 is placed into gear relief 801 and relief 303 to secure the gear to the cutter. In one embodiment, the cutter drive gears 800 are pinned to the cutter hub 302 (shown in FIG. 3). Referring to FIGS. 8 and 11, the barrel cutter is structured to drive cutting elements 103 with drive shaft 100 connected to bevel gear 1100. Bevel gear 1100 meshed with bevel gear 1101 which is connected to shaft 1105 which is connected to drive gear 805 which meshes with transfer gear 804. Transfer gear 804 meshes with cutter drive gear 800 which meshes with idler gear 803 and torque is transferred to each cutting element via idler gear 803 and drive gear 800 combinations. Transfer gear 804 and idler gears 803 are supported by shafts 1109. Shafts 1109 passing through and supported by clearance hole 1114 in side plate 102 and clearance hole 1115 in face plate 1102. Face plate 102 is assembled with cutter housing 107 by threaded fasteners (not shown) passing through clearance holes 1116 in side plate 102, clearance holes 1117 in face plate 1102 and into threaded holes 1106 in cutter housing 107.

Figure 3:
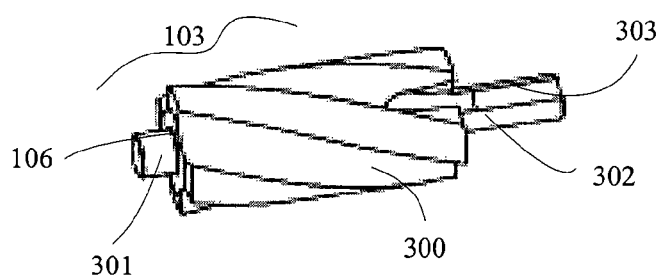
FIG. 3 is a perspective view of another cylindrical cutting element suitable for use in some end driven barrel cutters, for example, that of FIG. 1.

FIG. 3 illustrates that cutting element 103 has one or more cutting edges 106, and in one embodiment there are four cutting edges 106 as shown in FIG. 3. Cutting element 103 is supported on one end by a hub 301 and at the other end by a gear hub 302. A cutter relief 300 is designed trailing the cutting edge 106 to enhance cutting.

Figure 6:
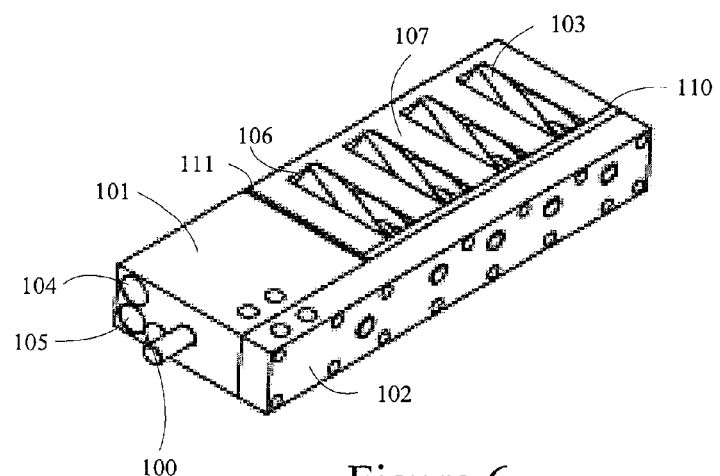
FIG. 6 is a perspective view of the barrel cutter of FIG. 1.

FIGS. 1, 6 and 11 illustrate features which beneficially flush bone debris out of the femoral cutter during operation. Sterile saline or other suitable fluid may be used for this purpose. The barrel cutter is designed with input port 104 and output port 105. Irrigation fluid is delivered to the barrel cutter by a plastic tube (not shown) structured to attach to the barrel cutter at port 104 to be channeled through housing 101, through face plate 1103 via irrigation input port 1107, into channel 1104 leading to longitudinal hole 1111 in communication with each cutting element 103 relief channel 1112. Irrigation fluid flows over cutting element 103 to be gathered in longitudinal hole 1113 in communication therewith. Irrigation fluid flowing through face plate 1103 via irrigation output port 1108 in communication with port 105 in housing 101 and into a plastic tube (not shown) structured to attach to housing 101.

Durability, sharpness and cleanability are important for the function and use of the femoral cutter. Given the small size of the femoral cutters, a single use device is preferred to provide sharp cutting elements in each surgical case and to ensure durability of the device. Cost is an important factor in single use devices. The use of gears to drive the cutting elements is costly for two reasons, the cost of the gears and the cost of machining to hold tolerances for proper function of the gears. Hence, a less expensive drive means would be desirable.

Figure 13:
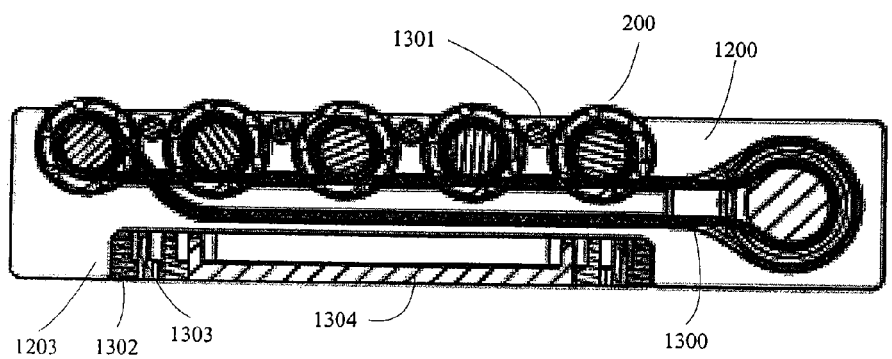
FIG. 13 is a side, cross-sectional view of the string driven barrel cutter of FIG. 12, taken through the drive loop.

FIG. 13 illustrates another embodiment of a barrel cutter, in which a string drive is used to drive each of the cutting elements. The string drive can be a continuous loop that is wrapped around each cutter and around an input shaft so that as the input shaft is rotated, each cutting element rotates. The string drive is designed with a drive loop 1300, which may be a monofilament string, multi-strand woven string or cord; single or multi-strand wire; drive belt, V-belt or timing belt; or other flexible band that can be placed around or on the cutting elements to impart rotation. The drive loop 1300 is wrapped around a drive shaft 1202 one time as shown, or in another embodiment multiple times (not shown) to take advantage of the increased friction between the drive loop and shaft with multiple windings.

The drive loop 1300 can be wrapped one or more times around each cutting element 200.

Figure 2:
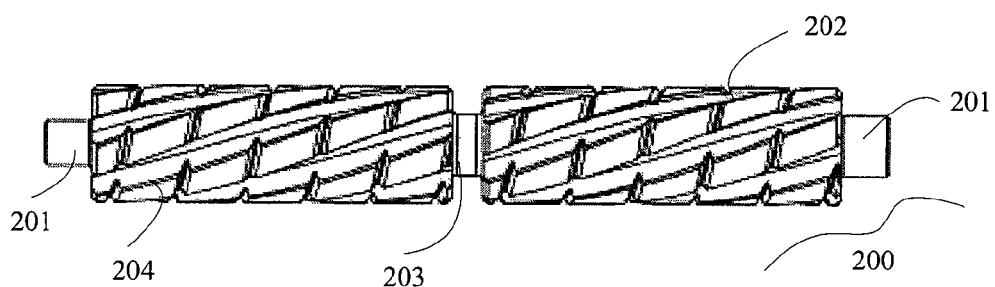
FIG. 2 is a perspective view of a cylindrical cutting element having a central drive recess suitable for use in some string driven barrel cutters, for example, that of FIG. 12.
Figure 14:
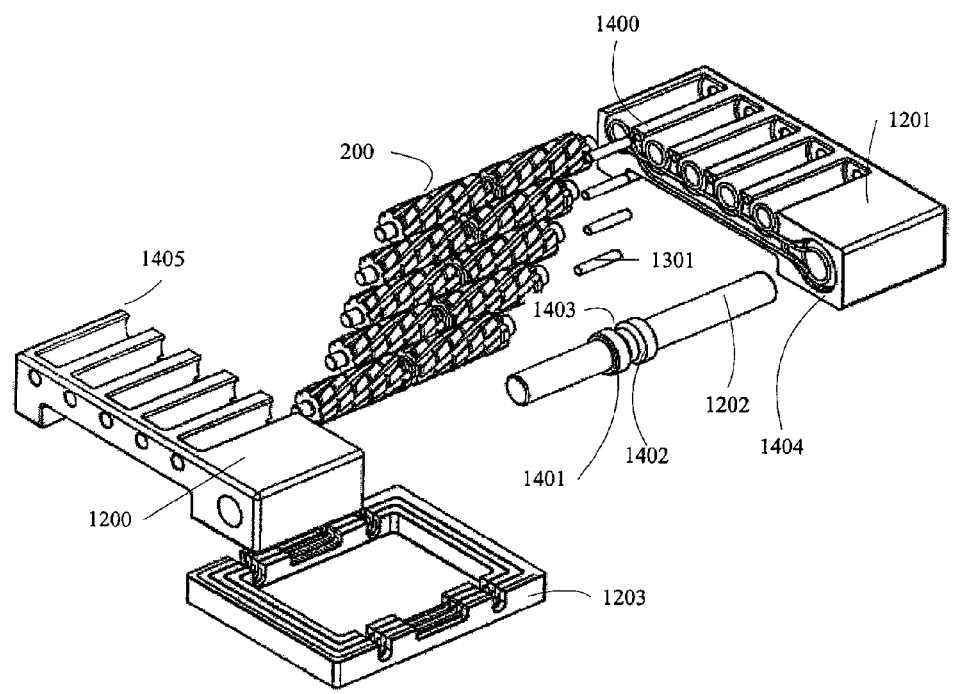
FIG. 14 is an exploded view of the string driven barrel cutter of FIG. 12.

FIG. 2 illustrates a cutting element 200 designed with a recess 203 for receiving drive loop 1300. The cutting element can be supported by hubs 201. Cutting element 200 includes cutting edges 202, and chip relief 204, formed as a circumferential groove in this embodiment. Cutting element 200 is structured with one or more cutting edges 202. Each cutting edge 202 is structured with one or more chip relief's 204 that improve cutting element's 200 chopping of articular cartilage present on the femoral condyle and in chopping bone to be removed. FIGS. 12, 13 and 14 illustrate an embodiment in which the string drive is integral to the femoral cutter. Drive shaft 1202 and cutting elements 200 are supported by a common housing 1200 and 1201, and a means for tensioning the loop drive 1300 is provided. Common housings 1200 and 1201 are held in alignment by alignment pins 1301 slidably received in holes 1400. Common housings 1200 and 1201 structured to be adhesively bonded together between common faces 1404 and 1405. In another embodiment (not shown) the drive shaft is supported in a separate housing and one or two flexible tubes connect the drive shaft housing to the cutting element housing. In an embodiment using one flexible tube the dive loop is wrapped around the drive shaft one or more times and passed through the flexible tube into the cutter housing wherein the loop drive is wrapped one or more times around each cutting element. In an embodiment using two flexible tubes, the drive loop would be an open loop in which the string is passed through one tube, into the cutting element housing, wrapped one or more times around each cutting element, routed out of the cutting element housing, through the second tube, into the drive shaft housing, then wrapped one or times around the drive shaft and connected to the other end of the drive loop. Alternatively, for the single or dual tube embodiments, the flexible tube may be rigid and made of steel, plastic or other suitable material.

FIG. 14 illustrates an embodiment in which drive shaft 1202 is designed with ridges 1401 and 1402 and a groove 1403 to guide drive loop 1300. The opposing faces 1404 and 1405 of the housing can be brought together over alignment pins 1301 inserted into holes 1400.

Figure 15:
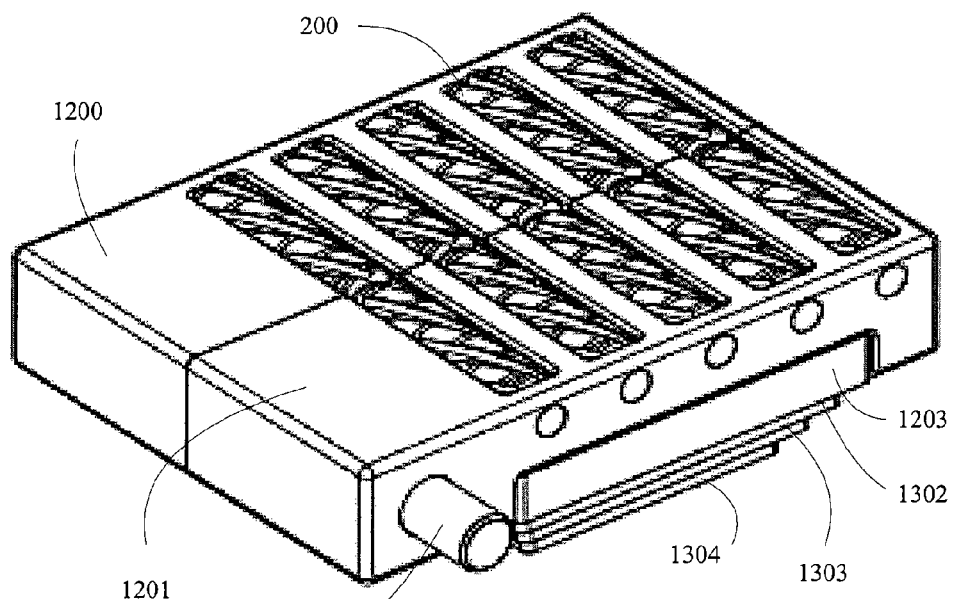
FIG. 15 is a perspective view of the string driven barrel cutter of FIG. 12, shown in a collapsed configuration.
Figure 16:
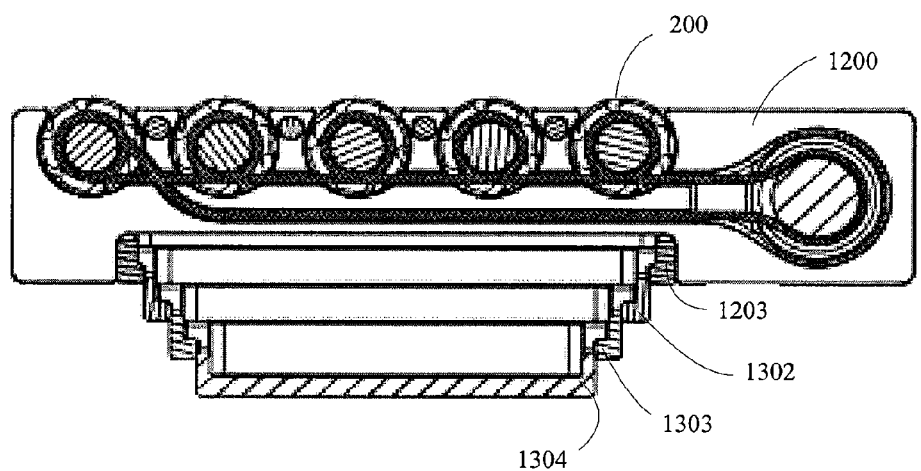
FIG. 16 is a side, cross-sectional view of the string driven barrel cutter of FIG. 12, taken through the drive loop, shown in an expanded telescope configuration.
Figure 17:
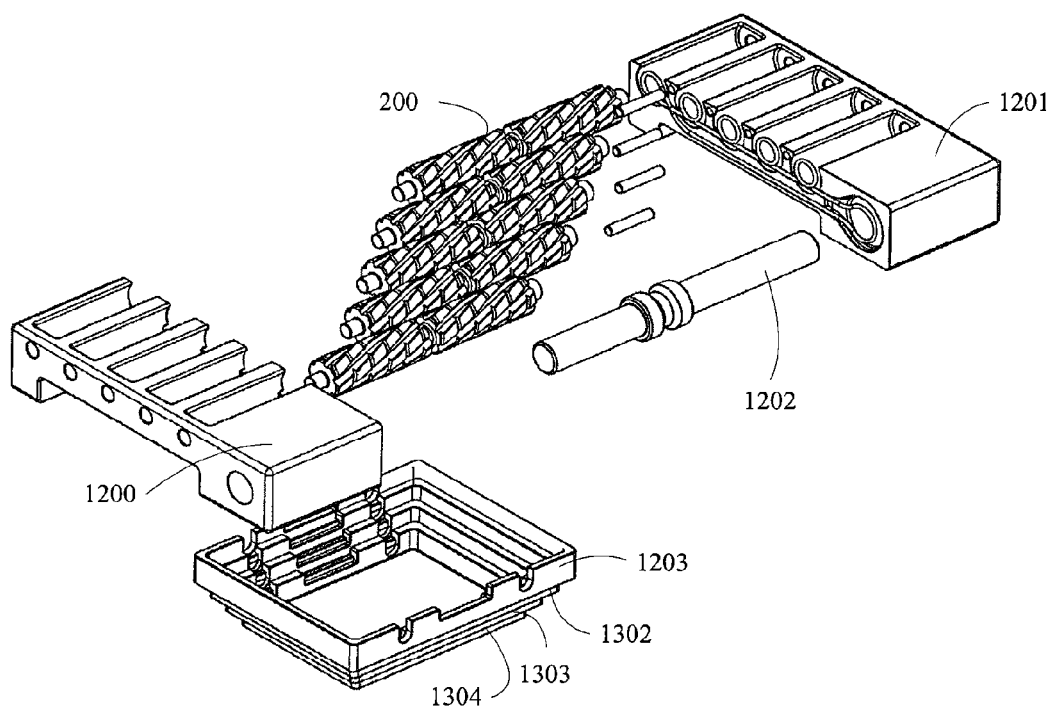
FIG. 17 is an exploded view of the string driven barrel cutter of FIG. 12, with the telescoping platforms shown in an expanded, configuration.

As described above, it is beneficial to expand the cutters within the patellofemoral compartment and tibiofemoral compartments. The barrel cutter is designed with a cylinder to provide axial expansion of the cutter. FIG. 13 illustrates that the cylinder may be of multiple stages as shown by telescoping platforms 1302, 1303 and 1304, which are held in place within housing 1200 and 1201 with telescoping platform 1203. FIG. 13 shows the cylinder in a collapsed position. FIGS. 15, 16 and 17 show the cylinder in an extended position.

Figure 4:
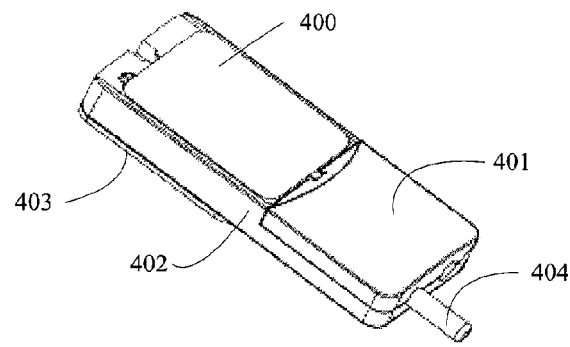
FIG. 4 is a perspective view of a reciprocating cutter having an upper, substantially planar cutting element.
Figure 5:
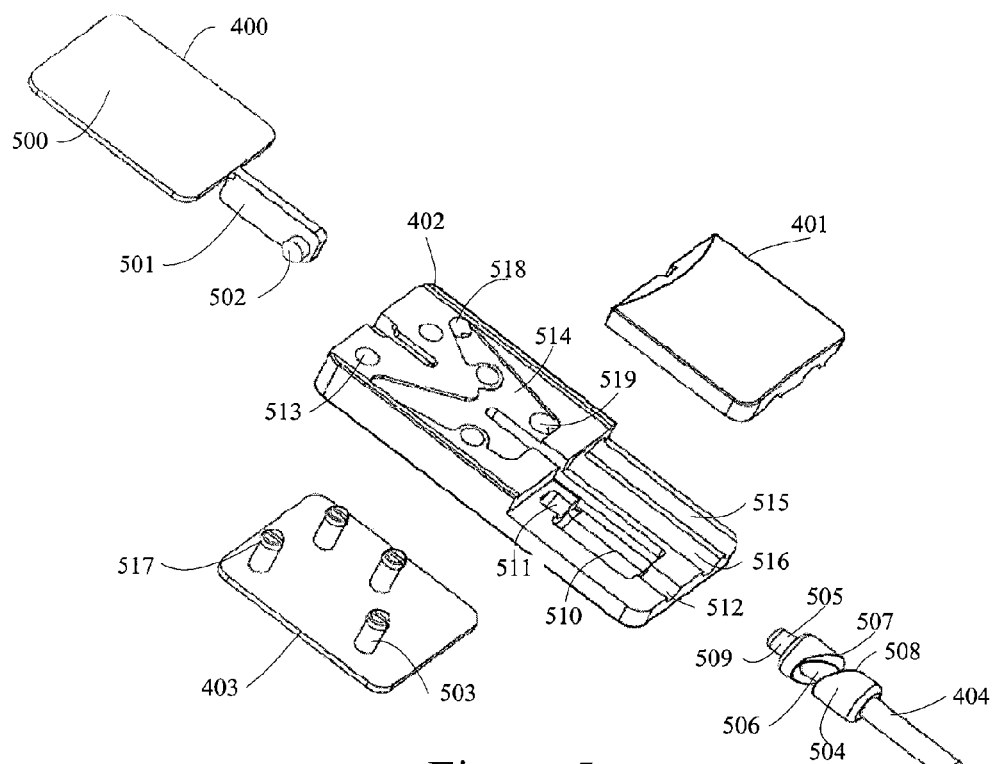
FIG. 5 is an exploded view of the reciprocating cutter of FIG. 4, showing the irrigation ports and the reciprocating drive shaft mechanism.

FIGS. 4 and 5 illustrate a reciprocating cutter designed to be placed in either the tibiofemoral compartment and/or in the patellofemoral compartment. Cutting element 400 is designed with cutting teeth on top surface 500. The cutting teeth may be continuous from side to side or include individual cutters staggered over the surface of the cutting element so as to provide uniform material removal over the surface of the cutting element. Alternatively, the top surface may have an abrasive texture to remove material. In either case, the surface of the cutting element may be continuous or may have holes to allow material removed from the femur to pass through.

Figure 33:
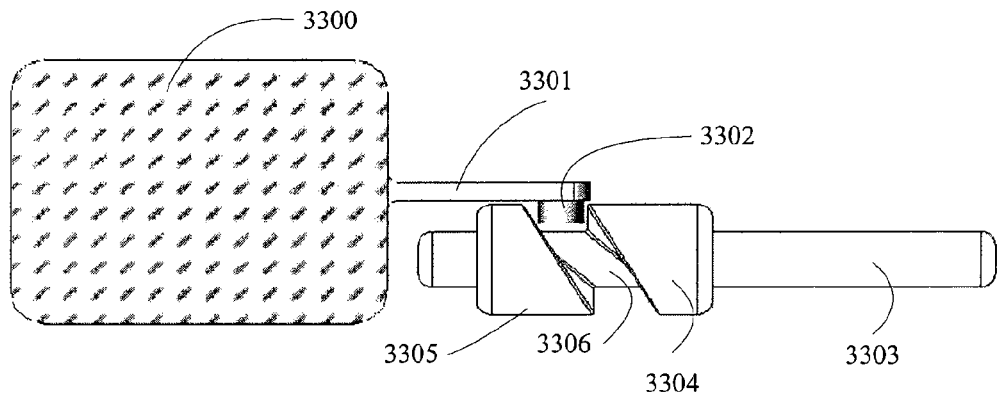
FIG. 33 is a schematic top view of a reciprocating drive top cutting element and drive shaft.

Cutting element 400 is driven in a reciprocating fashion by applying torque to drive shaft 404. Torque may be supplied by a surgical power drill or a motor. A flexible or solid drive shaft can be used to connect the surgical power drill or motor to drive shaft 404. A reciprocating drive groove 506 is formed by an upper boss 505 and a lower boss 504, and having an upper groove wall 507 and a lower groove wall 508. As the drive shaft spins, reciprocating drive groove 506 imparts a reciprocating motion to cutting element 400. A hub 502 rides within reciprocating drive groove 506 and moves in an axial direction to drive cutting element 400 via cutter arm 501. Drive shaft 404 includes an end hub 509 which is received in hub support 511 adjacent a reciprocating drive recess 510 and a drive shaft recess 512. Distal end of drive shaft 404 is structured with hub 509 to align and support distal end of drive shaft 404. Drive shaft 404 is supported in drive housing 402 and drive cover 401 each structured with hub support 511 to support distal end of drive shaft 404 and drive shaft support 512 to support drive shaft 404. Clearance for lower boss 504 and upper boss 505 within drive housing 402 and drive cover 401 is provided by recess 510. FIG. 33 illustrates that cam 3302 rides in the groove 3306 between bosses 3304 and 3305 while drive shaft 3303 rotates, resulting in a reciprocating motion of arm 3301 and cutting element 3300. Cutting element 400 is supported by drive housing 402. Drive shaft 404 and cutter arm 501 are held in relative position by drive housing 402 and enclosed by drive cover 401.

Figure 40:
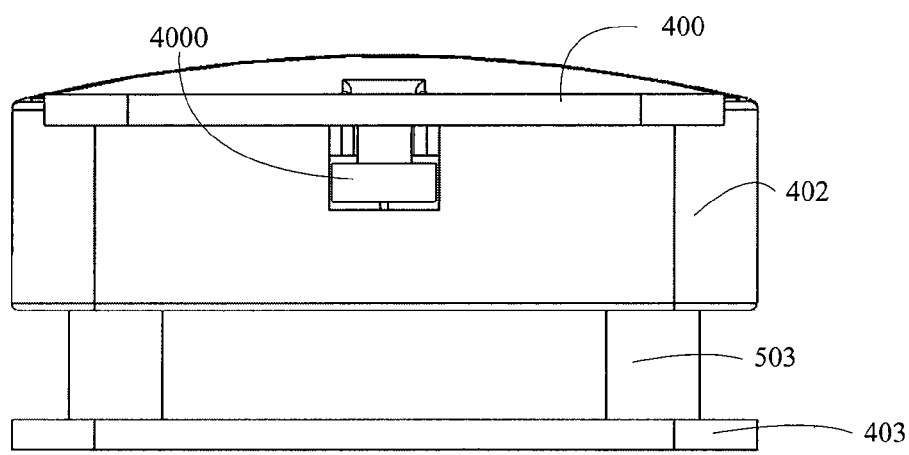
FIG. 40 is an end elevation view of a reciprocating cutter, having the telescoping platform in an extended configuration.
Figure 41:
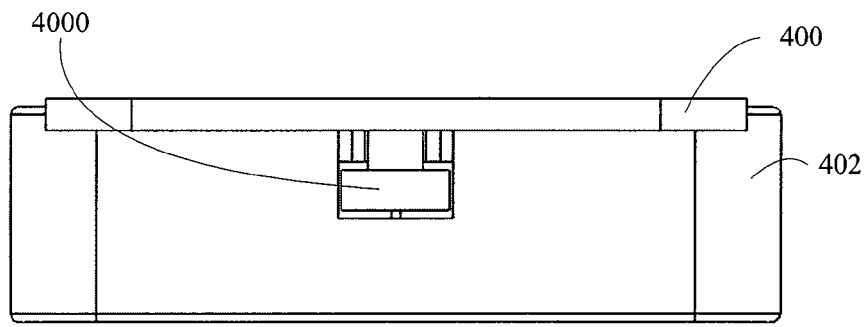
FIG. 41 is an end elevation view of the reciprocating cutter of FIG. 40, having the telescoping platform in a retracted or collapsed configuration.
Figure 42:
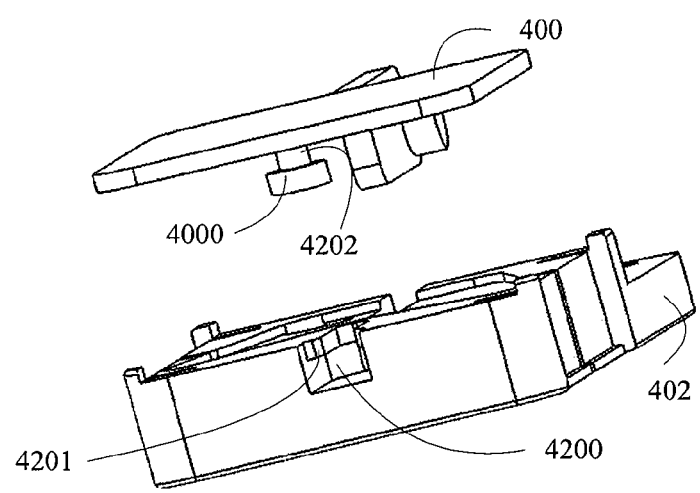
FIG. 42 is an exploded view of the reciprocating cutter of FIG. 40, showing the retainer for securing the top cutting element.

FIGS. 40, 41, and 42 show that as cutting element 400 reciprocates, the posterior aspect of the cutting element 400 is beneficially guided and cutting element 400 is retained on the surface of the drive housing 402. A retainer 4000 is visible on the underside of cutting element 400. The retainer 4000 fits into cavity 4200 and is held vertically by a shoulder 4201 fitting into a groove 4202. The cavity is elongated to allow reciprocating motion of the cutter element 400.

Figure 21:
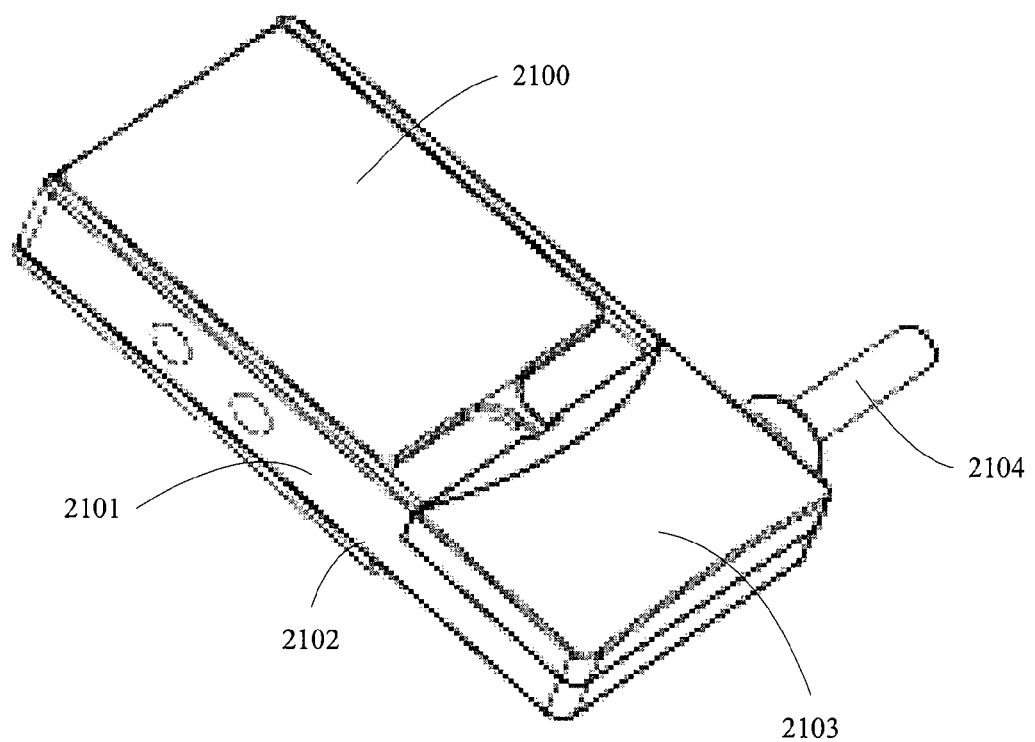
FIG. 21 is a perspective view of a reciprocating cutter having a substantially planar upper cutting element and a side drive shaft.
Figure 22:
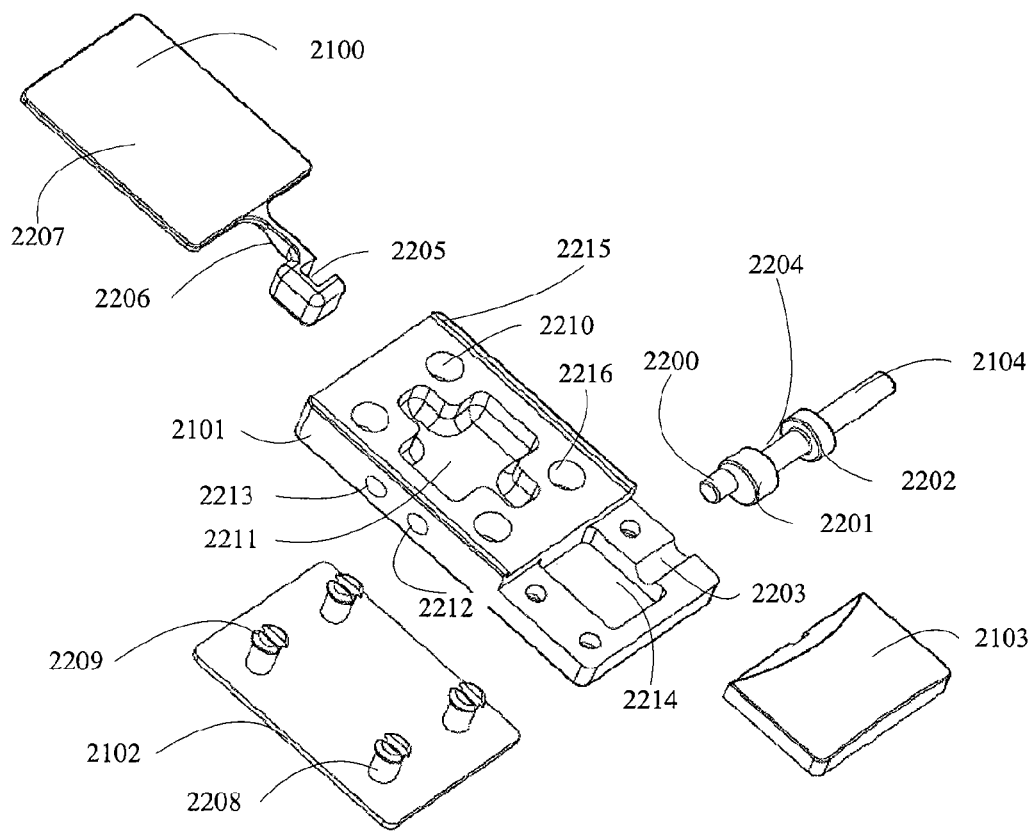
FIG. 22 is an exploded view of the reciprocating cutter of FIG. 21, showing irrigation ports and plenum, and an off-set cam reciprocating mechanism within.

FIGS. 21 and 22 illustrate an alternate embodiment having a cutting element 2100 structured to be supported on housing base 2101. Said housing 2101 base structured to support drive shaft 2104 and enclose said drive shaft 2104 with housing cap 2103. Drive shaft 2104 structured to oscillate cutting element 2100. Offset cam 2200 is in communication with channel 2205 in cutting element 2100 arm 2206. Housing base 2101 is structured with chamber 2214 to provide clearance for drive shaft 2104 bosses 2201 and 2202. Drive shaft 2104 cylinder 2204 is slidably received in channel 2203 in housing base and in adjoining channel (not shown) in housing cap 2103. Bosses 2201 and 2202 capture said channel 2203 to slidably retain drive shaft 2104. As drive shaft 2104 rotates, cam 2200 rotates and slides within channel 2104 thereby moving cutting element back and forth within bosses 2215 protruding from housing base 2101. Cutting surface 2207 structured to remove tissue when oscillated against adjoining bone. Cutting surface structure includes embodiments described herein, to include ridges, grit surface, protuberances, or other suitable cutting feature known to those skilled in the art. Reciprocating cutter is structured to telescope. Telescoping platform 2102 is structured to slidably assemble with housing base 2101. Guide posts 2208 are slidably received in holes 2210. The leading end of guide posts 2208 are structured with snap retainers 2209 that engage lips 2216 within holes 2210. Tissue removed from the femur flows into chamber 2211. Input hole 2212 is structured to attachably receive a tube (not shown) through which irrigation fluid flows into chamber 2211. Irrigation fluid is transported out of chamber 2211 through output hole 2213. Said output hole 2213 structure to attachably receive a tube (not shown) which may be connected to a vacuum system (not shown).

FIG. 5 illustrates that a port 515 brings irrigation fluid, e.g. sterile saline, into a cavity 514 behind cutting element 400 via opening 518. The fluid exits the cavity via opening 519 and port 516. As mentioned earlier, it is beneficial to wash debris from femoral resections away from the cutter.

FIGS. 4 and 5 illustrate a reciprocating cutter which can expand. A telescoping platform 403 is provided on the base of the cutter. Guide posts 503 align the telescoping platform 403 and limit travel by snap-in retainers 517. Guide posts 503 are designed to fit into and snap into receiving holes 513 in the drive housing 402.

FIG. 41 illustrates the reciprocating cutter in a fully collapsed position. The collapsed reciprocating cutter fits easily into a tibiofemoral compartment, or into the patellofemoral compartment. To tension the ligaments and capsule the reciprocating cutter can be expanded as shown in FIG. 40. Expansion of the telescoping platform may be accomplished by a mechanical cam, screw mechanism or scissors jack (not shown), or by a bladder. Bladder designs are described below.

Figure 18:
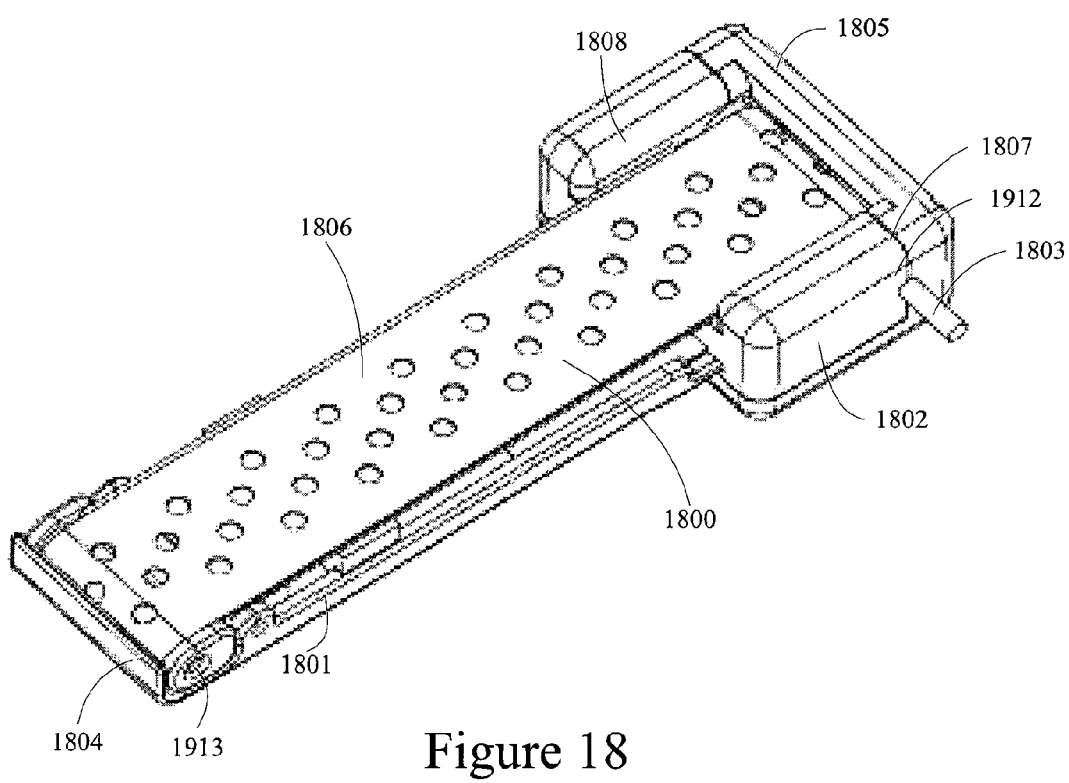
FIG. 18 is a perspective view of a belt cutter having a linear tensioning frame using a screw mechanism to tension the cutting belt.

FIG. 18 illustrates yet another embodiment, a femoral cutter having a cutting belt 1800. Cutting belt 1800 is supported on a frame and driven to move the cutting surface across the adjacent femoral condyle or trochlea. Cutting belt 1800 can be tensioned and supported on rollers. Torque is applied to the drive shaft 1803 by a surgical drill or motor with a flexible or rigid drive shaft as previously described. As the belt cutter is placed into a tibiofemoral compartment and operated, the tissue structures in the back of the knee need to be protected. A tissue protector 1804 is designed as part of the housing base 1801 for this purpose. A housing end cap 1805 may be seen at the anterior end.

Figure 19:
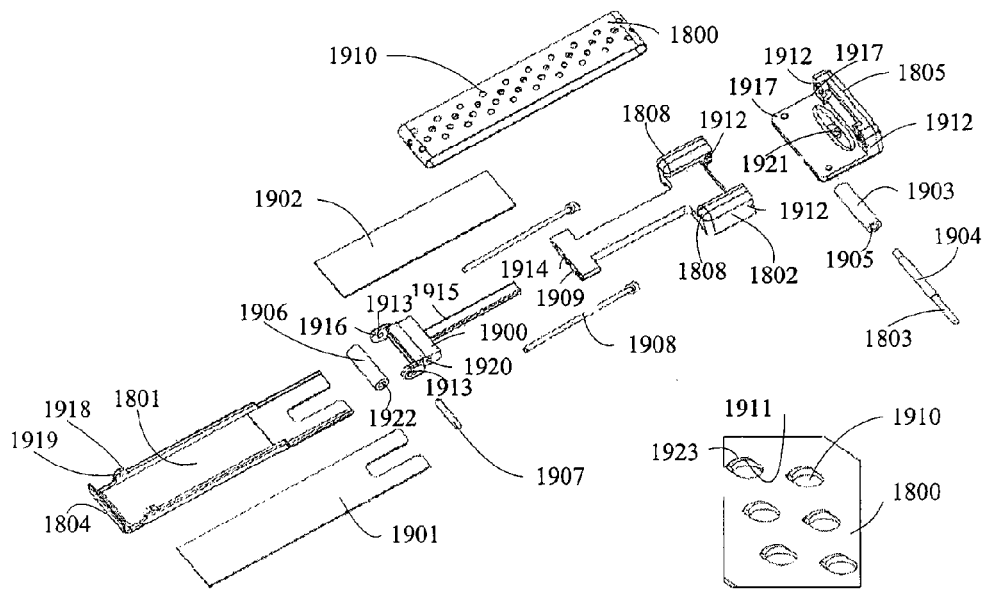
FIG. 19 is an exploded view of the belt cutter of FIG. 18 having a linear tensioning frame.

FIG. 19 illustrates the femoral cutter of FIG. 18 in an exploded view. Cutting belt 1800 is supported on an idler roller 1906 having a shaft 1907 received within, and a drive roller 1903 having a drive shaft cylinder 1904 received within. Hole 1922 through idler roller 1906 snuggly receives shaft 1907 structured to press fit shaft 1907 in hole 1922. Tensioning arm 1900 is structured with tabs 1916 protruding from distal end through which holes 1913 pass. Idler roller 1906 is positioned between tabs 1916 and shaft 1907 is slidably received through first hole 1913, press fit through hole 1922 in idler roller 1906, and slidably received in second hole 1913. As for the drive roller 1903, housing frame 1802 and housing end cap 1805 adjoin along interface 1807. Hole 1912 extends along interface 1807 and slidably receives drive shaft 1803. Hole 1905 through drive roller 1903 snuggly receives drive shaft 1803 structured to press fit drive shaft 1803 in hole 1905. Drive shaft 1803 is press fit into hole 1905. Boss 1915 protruding from housing frame 1802 is slidably received in channel 1914 in housing frame 1802. Screws 1908 are assembled in threaded holes 1909 in housing frame 1802. Assembled drive roller 1903 and drive shaft 1803 are slidably received by the portion of hole 1912 formed in housing frame 1802. Skid 1902 is placed on said assembly and the combination placed inside cutting belt 1800 with said cutting belt positioned between bosses 1808 protruding from housing frame 1802. Screws 1908 are advanced to properly tension cutting belt 1800. Drive shaft 1803 is secured by the portion of hole 1912 formed in housing end cap 1804. Housing end cap 1804 is assembled to housing frame with threaded fasteners (not shown) slidably received through holes 1917 and threaded into receiving holes (not shown) in housing frame 1802. Skid 1901 is placed inside housing base 1801 and combination is placed onto assembled cutting belt 1800, housing frame 1802 and housing end cap 1805. Housing base 1801 is assembled to tensioning arm 1900 with threaded fasteners (not shown) slidably received through holes 1919 in tabs 1918 protruding from housing base 1801. Said screws treadably received in threaded holes 1920 in tensioning arm 1900. Hole 1921 in housing frame 1802 is structured to attachably receive a plastic tube to which operating room suction is applied to remove fluid and tissue debris from tissue and bone cutting.

As the cutting surface 1806 of cutting belt 1800 works against the femoral condyle or trochlea, compressive force is carried by a skid 1902 below the belt and structural support is provided to the frame by a second skid 1901. Tissue is removed by one or more protuberances 1923 structured in the cutting belt 1800. Such protuberances 1923 formed by stamping or pressing a form into cutting belt 1800, or by attaching a formed or machined protuberance to the cutting belt 1800. Such attachment by adhesive, welding, diffusion bonding, press fit or other attachable means know in the art. Cutting belt 1800 is fabricated from stainless steel, cobalt chromium molybdenum alloy, or other suitable metal. Alternatively, cutting belt 1800 may be fabricated from rubber, urethane, or other suitable polymeric material with embedded protuberances as described above. Optionally, said polymeric cutting belt may be reinforced by fibers, metal mesh or other suitable material to increase strength and durability. A polymeric cutting belt can have integral metal cutting elements with protuberances. Alternatively, the metal cutting elements can be abrasive. To tension the cutting belt 1800, the housing frame 1802 is adjustable by turning two screws 1908 to advance a tensioning arm 1900 to increase tension on the belt cutter. The belt is driven in the direction shown in FIG. 19 by applying torque to the drive shaft 1803 which is attached to the drive roller 1903. The belt slides across upper skid 1902 and lower skid 1901, and turns on an idler roller 1906. A surgical drill, or a motor, with a flexible drive shaft as previously described can be used to apply torque to the drive shaft 1803.

To remove material from the femur, the cutting belt 1800 is designed with holes 1910 that create a rough edge when run against the femur. Alternately, the trailing edge 1911 of the hole 1800 is elevated to form a grater for more aggressive cartilage and bone removal (see the belt detail in FIG. 19). The cutting belt is formed by cutting or stamping the hole pattern in a strip of metal or other suitable material and welding or bonding the ends together to form a belt. Alternatively, the outer surface of belt 1800 can be abrasive.

Figure 43:
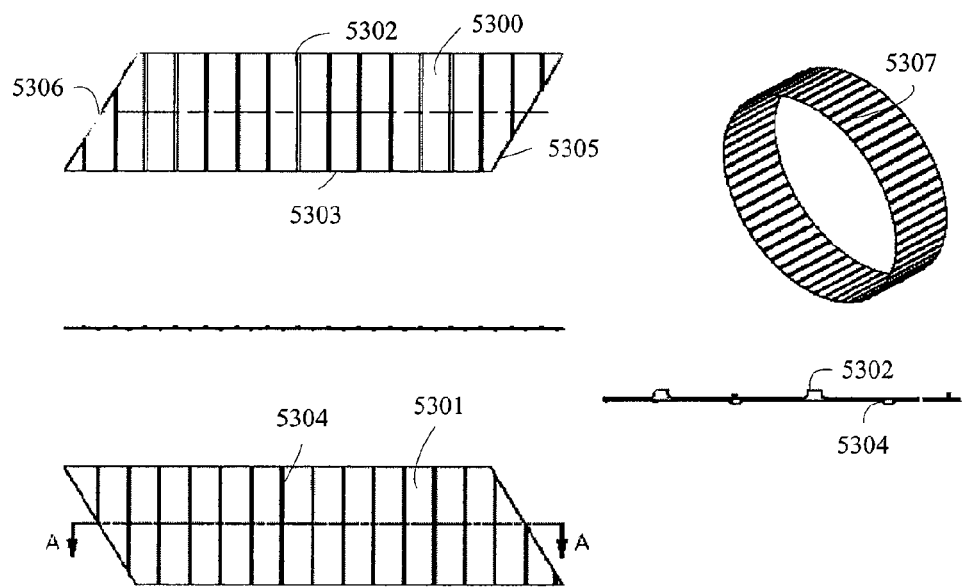
FIG. 43 includes orthogonal views and a perspective view of a cutting belt.
Figure 44:
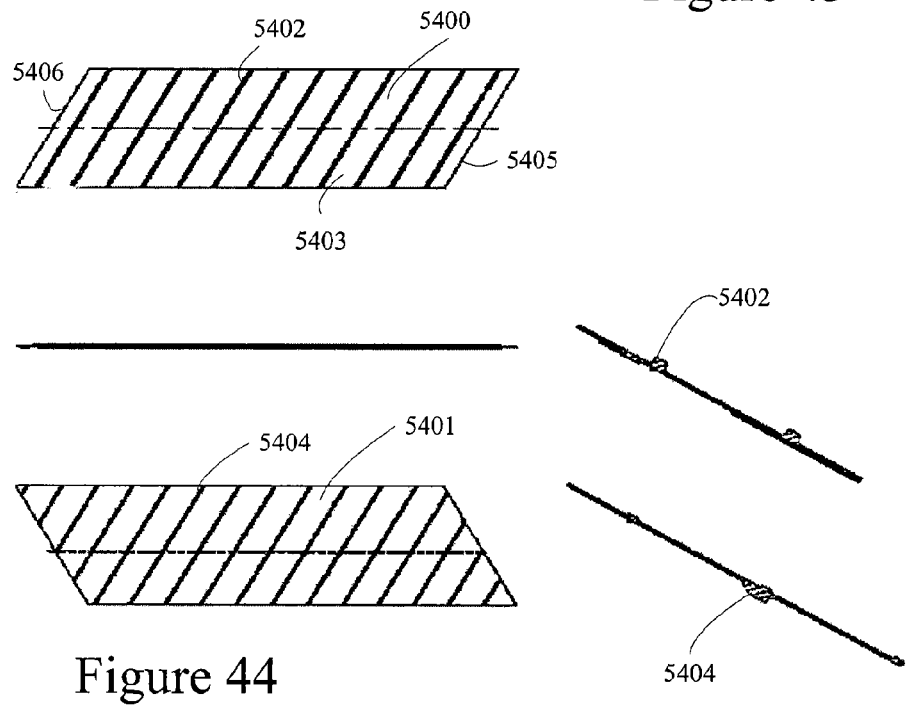
FIG. 44 includes orthogonal views of a cutting belt.
Figure 45:
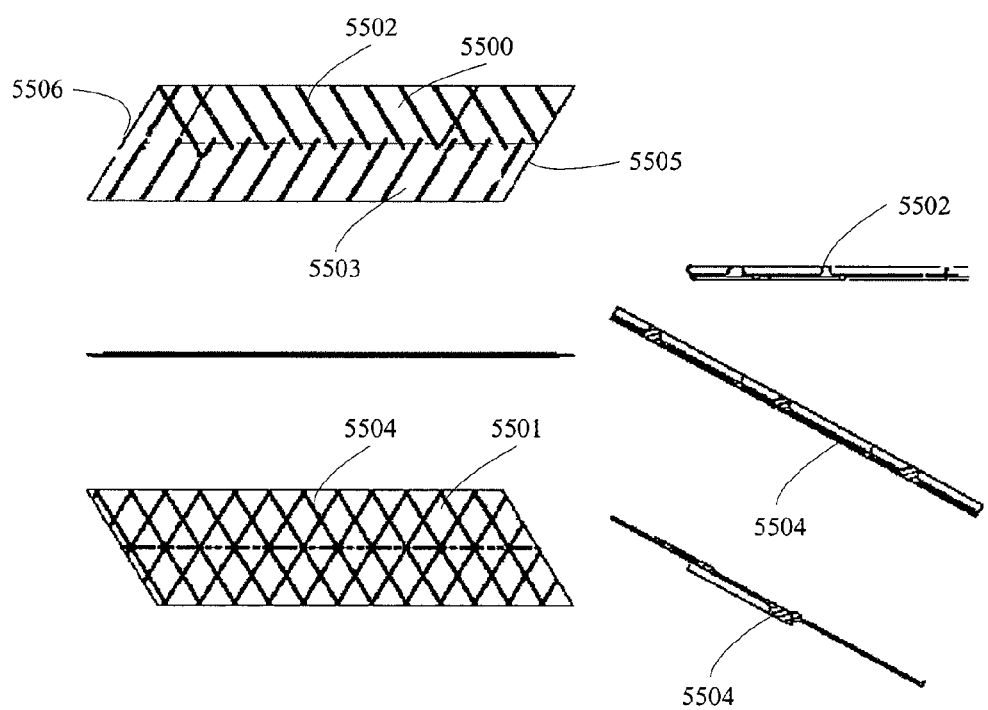
FIG. 45 includes orthogonal views of a cutting belt.

FIGS. 43, 44 and 45 illustrate alternate cutting belt embodiments fabricated from a strip that is welded or bonded (e.g. at 5307) into a belt or loop. In an alternate embodiment, a cutting pattern is chemically etched, stamped or machined into the outer surface of the cutting belt. As shown in FIG. 43, ridges 5302 are formed into the outer surface 5300 of the cutting belt. The outer ridge pattern 5302 is perpendicular to the side 5303 of the belt. The inner surface 5301 may have a pattern chemically etched, stamped or machined in it to enhance traction with the drive roller described above, or the inner surface may be smooth or roughened. The inner ridge pattern 5304 is perpendicular to the side 5303 of the belt. The belt is formed into a loop and the fastening edges 5305 and 5306 are welded or bonded together.

FIG. 44 shows an alternate embodiment, in which a cutting pattern is chemically etched, stamped or machined into the outer surface of the cutting belt. Ridges 5402 are formed into the outer surface 5400 of the cutting belt. The outer ridge pattern 5402 is inclined relative to the side 5403 of the belt. The inner surface 5401 may have a pattern chemically etched, stamped or machined in it to enhance traction with the drive roller described above, or the inner surface may be smooth or roughened. The inner ridge pattern 5404 is inclined relative to the side 5403 of the belt. The belt is formed into a loop and the fastening edges 5405 and 5406 are welded or bonded together.

FIG. 45 shows an alternate embodiment belt having a side 5503, in which belt a cutting pattern is chemically etched, stamped or machined into the outer surface of the cutting belt. Alternatively, the outer surface of belt can be abrasive. Abrasive surface, as used herein, formed by grit blasting, plasma spray, bonding abrasive material, or other fabrication method known to one skilled in the art. Ridges 5502 are formed into the outer surface 5500 of the cutting belt. The outer ridge pattern 5502 is alternating, opposing, inclined ridges partially spanning the belt. The inner surface 5501 may have a pattern chemically etched, stamped or machined in it to enhance traction with the drive roller described above, or the inner surface may be smooth or roughened. The inner ridge pattern 5504 is a diamond pattern. The belt is formed into a loop and the fastening edges 5505 and 5506 are welded or bonded together.

Figure 46:
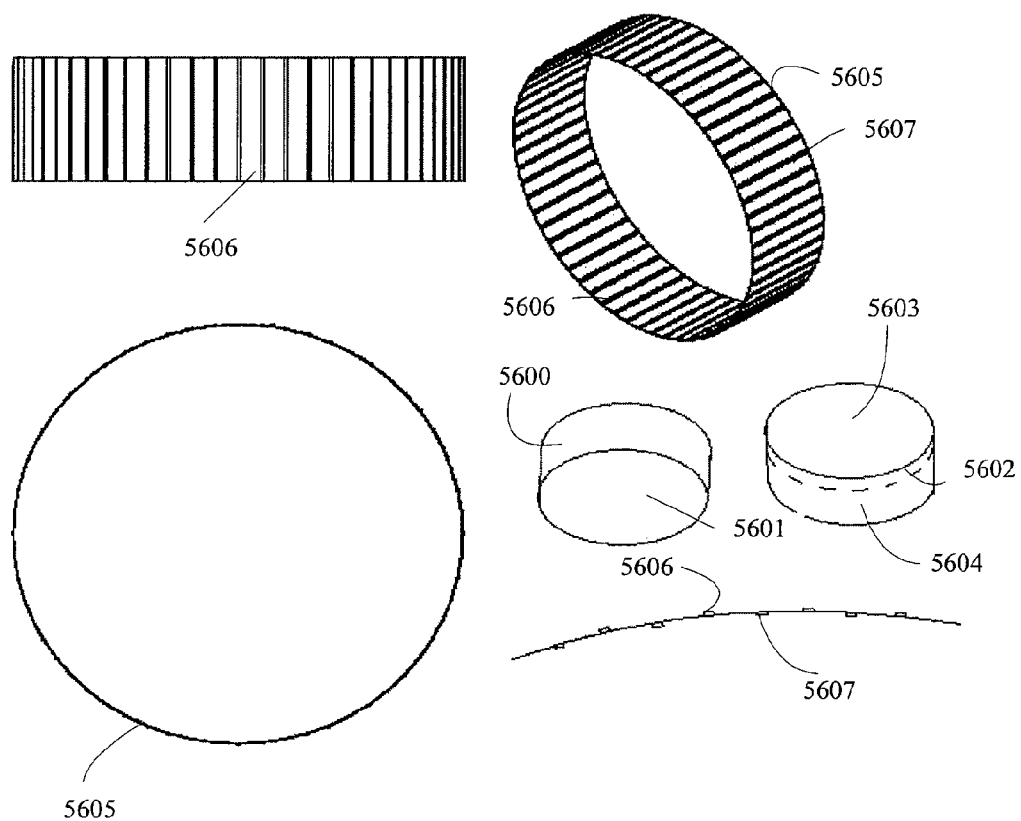
FIG. 46 includes orthogonal views of a cutting belt.

FIG. 46 illustrates yet another embodiment, in which the cutting belt 5605 is made from a deep drawn can 5600. A right cylinder is formed by deep drawing stainless steel or other suitable material. The can 5600 is open on one end 5601 and closed on the other 5603. The closed end of the can is removed along out line 5602 forming a continuous belt 5604 into which the patterns described above can be chemically etched, machined or stamped. For example, perpendicular ridges 5607 are chemically etched, stamped or machined into the outer surface of the cutting belt 5605. For traction with the drive roller a ridge pattern may be formed into the inner surface of the belt. A perpendicular ridge pattern 5606 on the inner surface is shown in FIG. 46. It should be noted that the outer and inner surface patterns described above can be used in any combination and that holes through the belt as previously described can be added.

Figure 20:
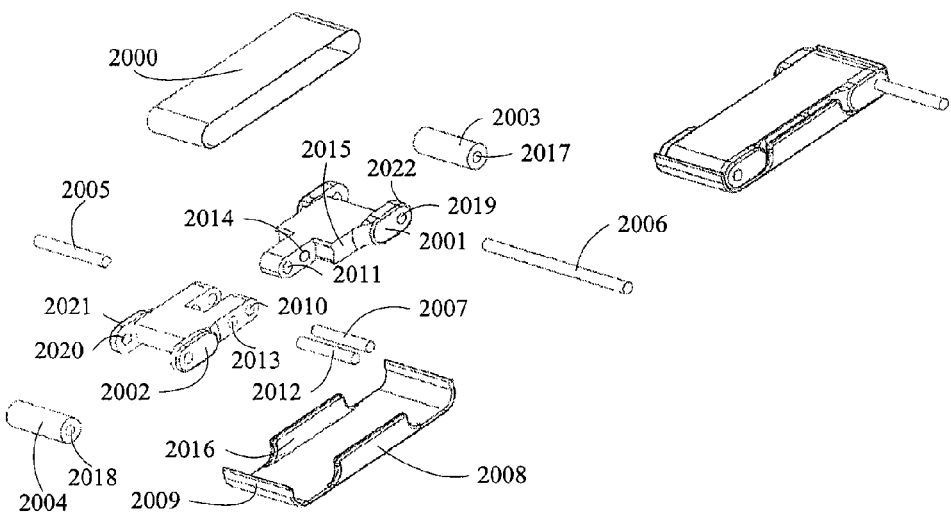
FIG. 20 is an exploded view of another belt cutter, having a hinge tensioning frame using a scissors mechanism to tension the cutting belt.

FIG. 20 illustrates an alternate embodiment belt cutter in which the frame and tensioning mechanism uses a hinged frame. In this embodiment, the anterior tensioning frame 2001 having support face 205 and hole 204, and the posterior tensioning frame 2002 are initially pinned together with one pin 2007 to form a hinge. Pin 2007 is slidably received through first hole 2010 then press fit through hole 2014 then slidably received in second hole 2010. The tensioning frame 2001 and 2002 support drive roller 2003 that is press fit or attached to drive shaft 2006 received within a drive roller 2003, and an idler roller 2004 rotating on a shaft 2005. Idler roller 2004 is placed between tabs 2021 protruding from posterior tensioning frame 2002. Shaft 2005 is slidably received through first hole 2020 and press fit through hole 2018 in idler roller 2004 then slidably received in second hole 2020. Drive roller 2003 is placed between tabs 2022. Drive shaft 2006 is slidably received through first hole 2019 and press fit through hole 2017 in drive roller 2003 then slidably received in second hole 2019. The tensioning frame is angled about the pivot pin 2007 to allow placing the tensioning frame into the cutting belt 2000. Once in place, the tensioning frame is opened into a straight position aligning the anterior and posterior tensioning frames, 2001 and 2002, respectively. The tensioning frame is held in this position by placing locking pin 2012 into a receiving hole 2013 in the posterior tensioning frame 2002 that is now aligned with a receiving hole 2011 in the anterior tensioning frame 2001. Pin 2012 is slidably received through first hole 2013 then press fit through hole 2011 the slidably received in second hole 2013. The assembled tensioning frame includes a distal tissue protector 2009, and a cutting belt which is supported in a housing base 2008 having a support face 2016. Support faces 2016 of housing base 2008 are structured to snap fit on to tension frame assembly at adjoining support faces 2015 on anterior tensioning frame 2001.

Figure 28:
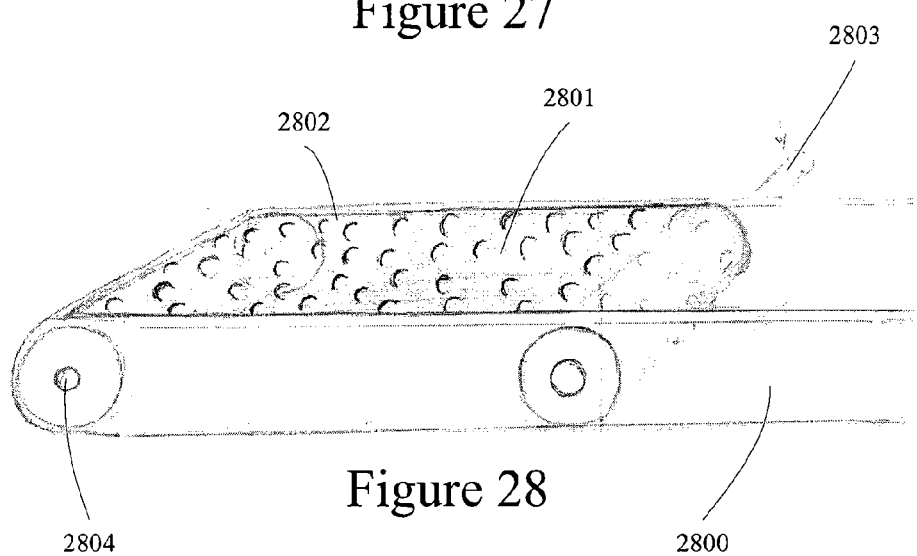
FIG. 28 is a perspective view of a belt cutter.

FIG. 28 illustrates another embodiment in which the belt cutter 2801, having frame 2800, drive shaft 2803, and shaft 2804, has the cutting teeth 2802 directed posteriorly, so as to force the femur posteriorly while cutting.

Figure 29:
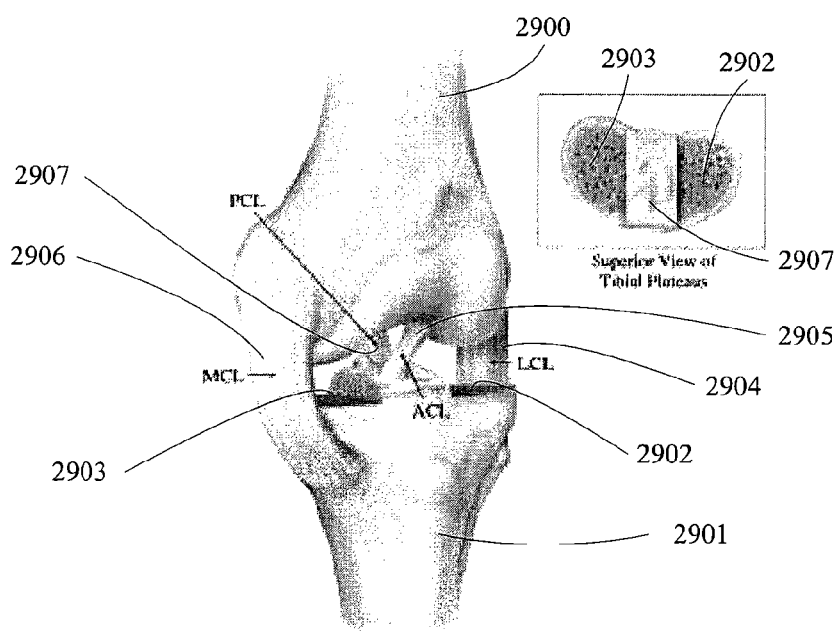
FIG. 29 is a perspective view of a knee joint with the tibial plateaus resected.

FIG. 29 illustrates how the tibial plateau can be prepared by resecting the articular surfaces leaving lateral support surface 2902 and medial support surface 2903 on which tissue guided femoral cutters are placed to prepare the adjacent femoral condyles. The medial 2903 and lateral 2902 support surfaces may be prepared at the same time thereby allowing simultaneous preparation of medial and lateral femoral condyles. Optionally, either medial 2903 or lateral 2902 support surface may be prepared initially followed by preparation of the adjacent femoral condyle. A spacer may be placed in the prepared tibiofemoral compartment followed by preparation of the adjacent tibial support surface followed by preparation of the adjacent femoral condyle. The medial and lateral tibial articular surfaces may be resected independently as shown in FIG. 29 in which case the tibial eminence 2907 is preserved. Alternatively, the anterior portion of the tibial eminence 2907 may be resected to allow for a bridge or connection between the medial and lateral tibial implants, or the tibial eminence 2907 may be resected. The medial and lateral tibial resections may be co-planar. Alternatively, the medial and lateral resection may be parallel, but not co-planar. In yet another embodiment the medial and lateral tibial resection may not be co-planar nor parallel. The femoral condyles may be resected independently, simultaneously, or in combination with the femoral trochlea. In one embodiment the femoral cutters telescope to distract the joint; either one or both of the tibiofemoral compartments and/or the patellofemoral compartment. Such distraction can be performed under constant load. Alternatively, such distraction may be at discrete displacement steps or distracted to a desirable displacement for condyle(s) and/or trochlea resection. Femoral condyle preparation is guided by the kinematics of the knee joint. The tibia 2901 moves in a predetermined fashion about the femur 2900. This motion is determined by the soft tissue structures spanning the knee. The anterior cruciate ligament (ACL) 2905 and the posterior cruciate ligament (PCL) 2907 extend from the femoral intracondylar notch to the tibial eminence 2908. The medial collateral ligament (MCL) 2906 extends from the medial side of the femur to the medial side of the tibia. The lateral collateral ligament (LCL) 2904 extends from the lateral side of the femur to the lateral side of the tibia. The ACL 2905, PCL 2907, MCL 2906 and LCL 2904 are the primary ligamentous structures guiding motion of the tibia relative to the femur.

In tissue guided surgery a femoral cutter may be placed in each tibiofemoral compartment and in the patellofemoral compartment. The cutting elements are held against the femur while the knee is flexed and extended in order to remove bone from the femur to prepare support surfaces for trochlear and/or condylar implants. Initially, it is beneficial to tension the ligaments spanning the knee and the joint capsule to stabilize the joint with the cutters in place and to provide uniform kinematic motion. As bone is removed it is beneficial to expand the cutters to maintain tension on the ligaments spanning the knee and the joint capsule. The cutters may be expanded incrementally to discrete heights, or variably under constant distraction force. In the first case, which is referred to as "displacement control," spacers may be placed under the cutters to expand the cutter, or a hydraulic cylinder with incremental fluid filling may be designed into the cutter to expand the cutter, in the patellofemoral compartment or in either of the tibiofemoral compartments. In the second case, which is referred to as "load control," a hydraulic cylinder, or a bladder, with pressure controlled fluid filling may be designed into the cutter to expand the cutter in the patellofemoral compartment or in the either of the tibiofemoral compartments.

Figure 30:
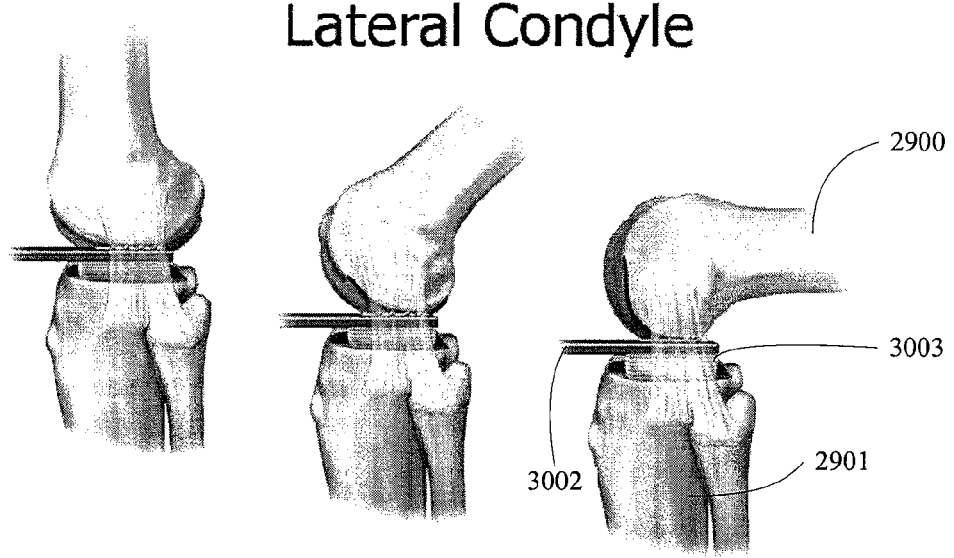
FIG. 30 is a lateral side view of the knee with a telescoping cutter positioned in the lateral tibiofemoral joint.
Figure 31:
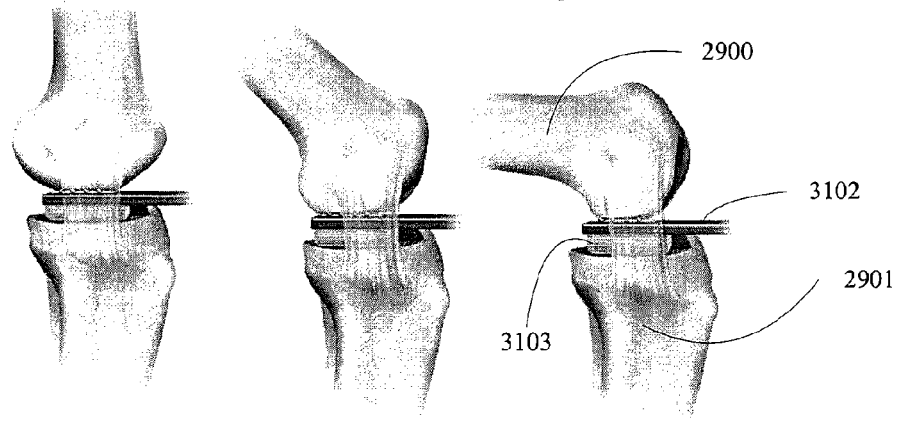
FIG. 31 is a medial side view of the knee with a telescoping cutter positioned in the medial tibiofemoral joint.
Figure 32:
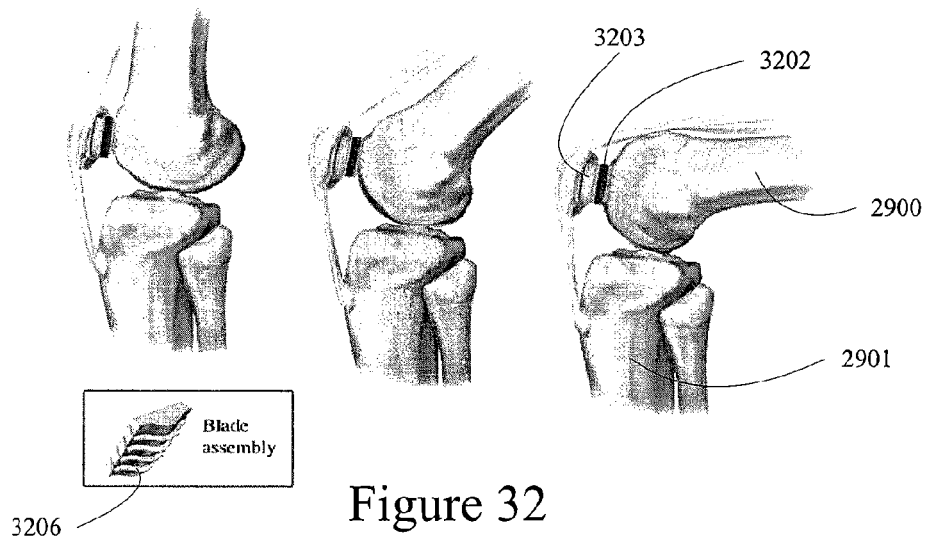
FIG. 32 is lateral side view of the knee with a telescoping cutter positioned in the patellofemoral joint.

FIGS. 30, 31 and 32 illustrate that the medial and lateral femoral condyles may be prepared independently with a femoral cutter 3002, placed in the lateral tibiofemoral compartment first to prepare the lateral femoral condyle. A spacer is placed in the lateral tibiofemoral compartment (not shown) after preparation of the lateral condyle, and the procedure is repeated by placing a femoral cutter 3102 in the medial tibiofemoral compartment. A bladder 3003 or 3103 may be used in conjunction with the lateral or medial femoral cutter, respectively.

FIG. 32 illustrates that the femoral trochlea may be prepared by placing a femoral cutter 3202 on the patella. The cutter can be structured to prepare a linear surface generally in a medial—lateral orientation and curved in a sagittal plane. Alternately, cutting elements 3206 as shown in inset of FIG. 32, the cutter, structured with various cutting elements to include barrel cutters, belt cutters, reciprocating cutters or shavers, may be contoured to simulate the shape of the patellar groove. Telescoping bellows 3203 may be used as well.

Figure 34:
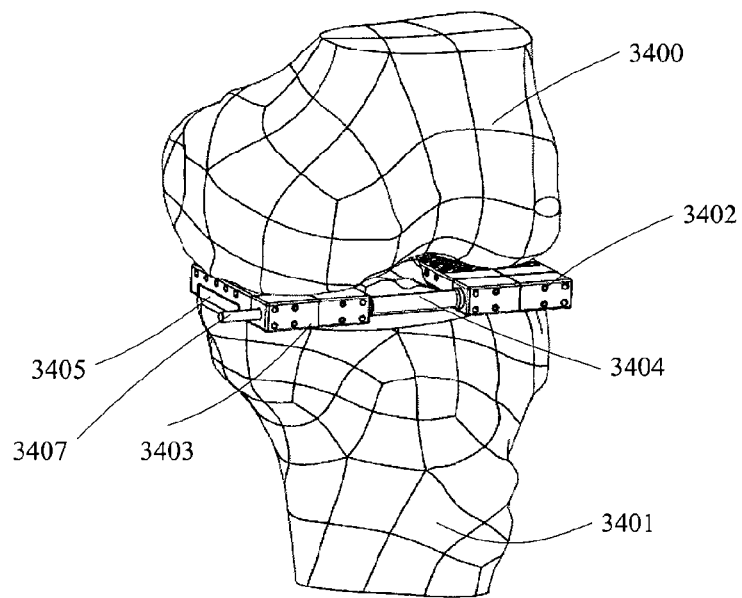
FIG. 34 is a perspective view of dual barrel cutters, which can be similar to the barrel cutters of FIG. 12, shown in position in the tibiofemoral compartments.
Figure 35:
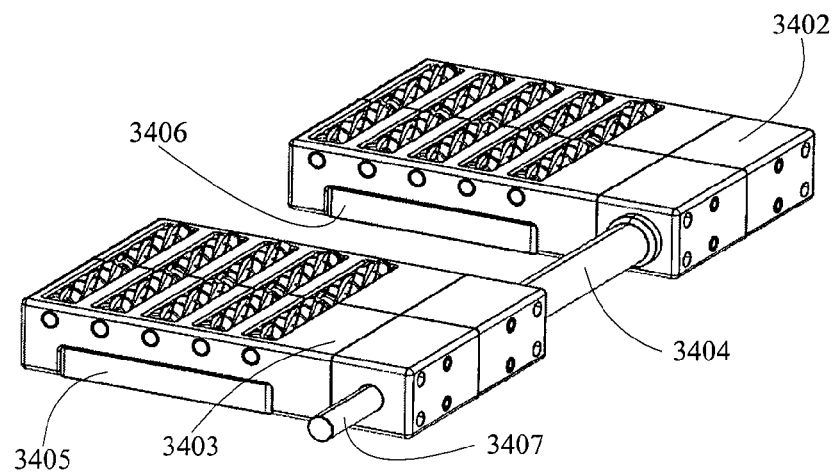
FIG. 35 is a perspective view of dual barrel cutters, for example the barrel cutters of FIG. 12.

FIGS. 34 and 35 illustrate two barrel cutters linked together. In preparing the medial and lateral tibiofemoral compartments it may be beneficial to place femoral cutters in each compartment and simultaneously prepare the medial and lateral femoral condyles. In the case of the barrel cutters, the two cutters are linked together with one cutter 3402, having telescoping platform 3406, placed in the lateral tibiofemoral compartment and the other cutter 3403, having telescoping platform 3405, placed in the medial tibiofemoral compartment. The connecting bridge 3404 transfers torque from drive shaft 3407 between the two femoral cutters. Alternately, the two cutters may be powered independently. The connecting bridge 3404 may be rigid and of fixed length or in another embodiment the connecting bridge 3404 is flexible and telescopes to enable independent positioning of the femoral cutters within each tibiofemoral compartment.

Figure 36:
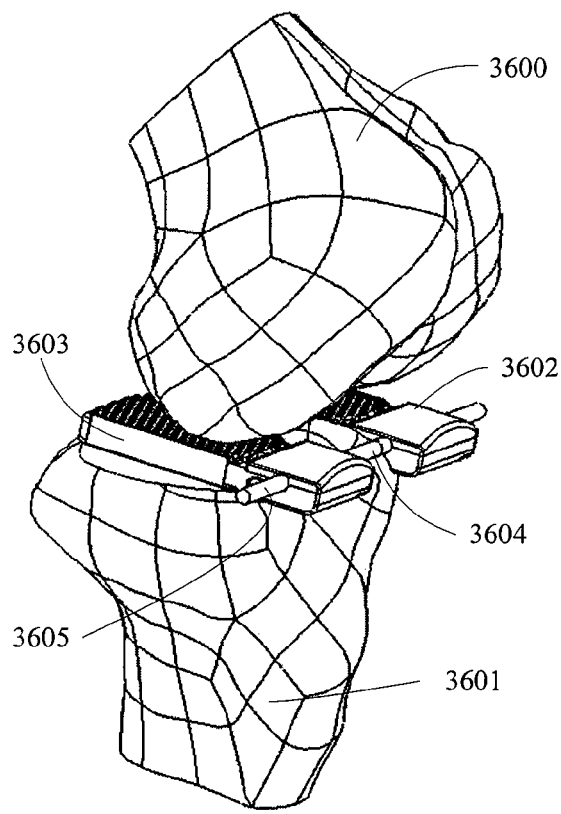
FIG. 36 is a perspective view of dual reciprocating cutters shown in position in the tibiofemoral compartments.
Figure 37:
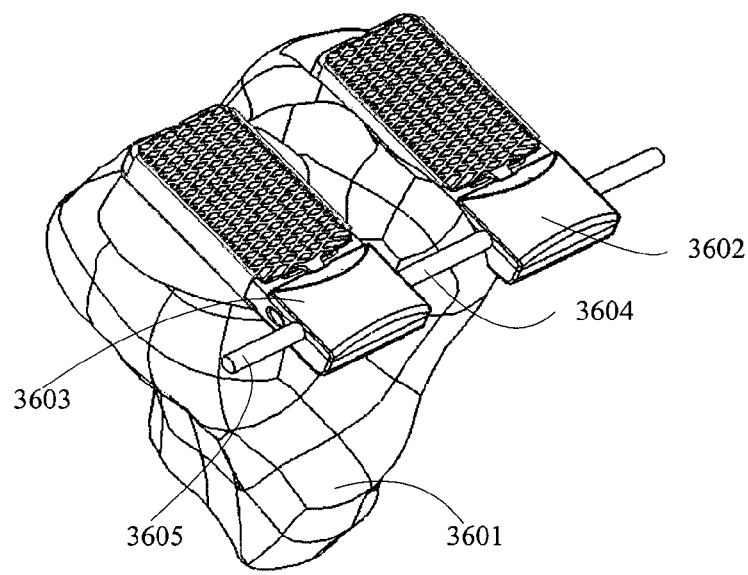
FIG. 37 is a perspective view of dual barrel cutters positioned in the knee joint.

FIGS. 36 and 37 illustrate two reciprocating cutters linked together, with one cutter 3602 placed in the lateral tibiofemoral compartment and the other cutter 3603 placed in the medial tibiofemoral compartment. The connecting bridge 3604 transfers torque from drive shaft 3605 between the two femoral cutters. Alternately, the two cutters may be powered independently. The connecting bridge 3604 may be rigid and of fixed length or in a preferred embodiment the connecting bridge 3604 is flexible and telescopes to enable independent positioning of the femoral cutters within each tibiofemoral compartment.

Figure 27:
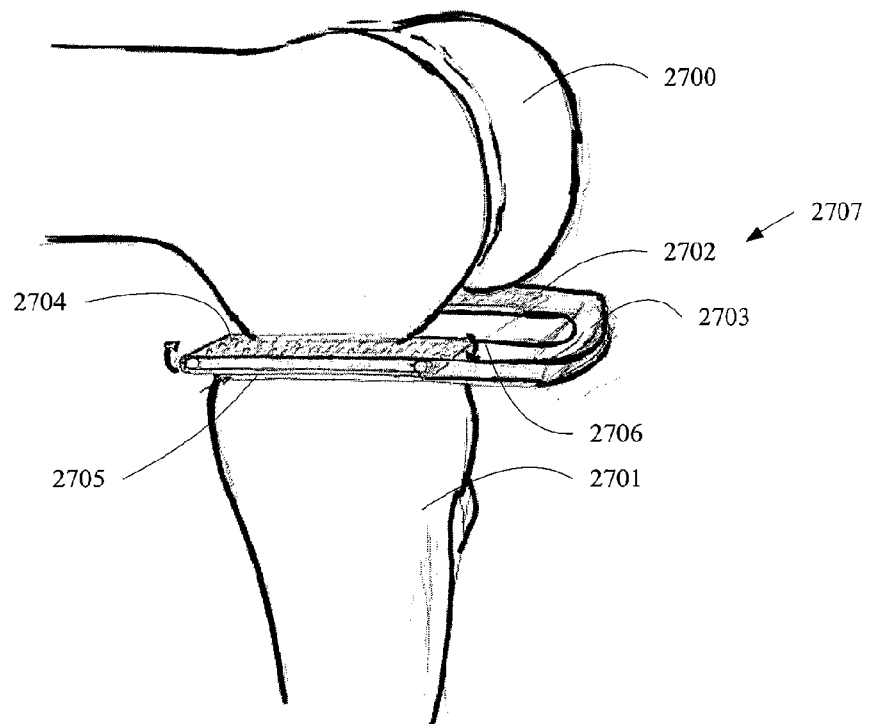
FIG. 27 is a perspective view of a dual belt cutter positioned in the knee joint.
Figure 38:
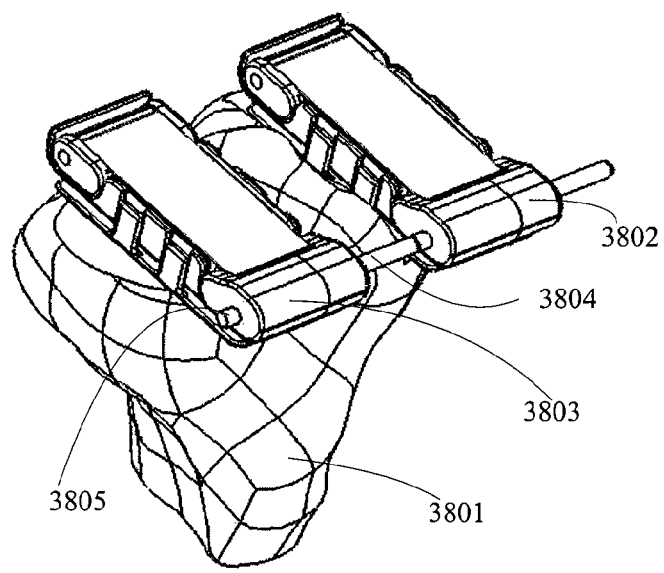
FIG. 38 is a perspective view of dual belt cutters, for example the belt cutters of FIG. 20, shown in position in the tibiofemoral compartments.
Figure 39:
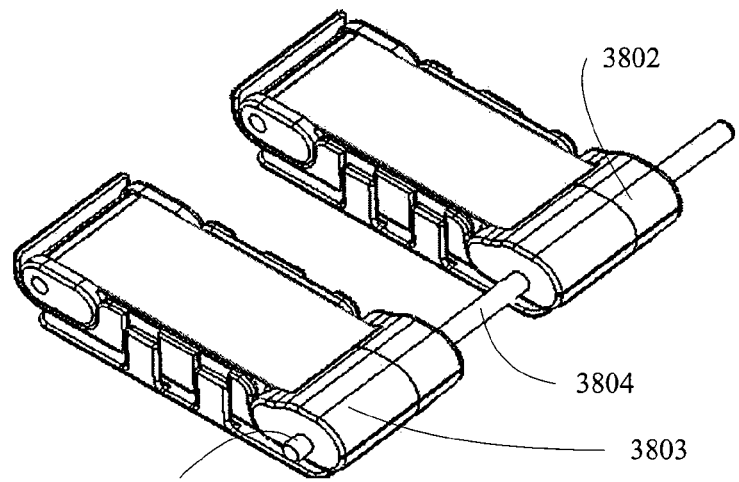
FIG. 39 is a perspective view of dual belt cutters, for example the belt cutters of FIG. 20.

FIGS. 27, 38 and 39 illustrate two belt cutters linked together, to form a dual belt cutter 2707, with one cutter 2702 or 3802 placed in the lateral tibiofemoral compartment (between femurs 2700 or 3600 and tibias 2701 or 3601) and the other cutter 2706 or 3803 placed in the medial tibiofemoral compartment. The connecting bridge 2703 or 3804 transfers torque between the two femoral cutters. Alternately, the two cutters may be powered independently. The connecting bridge 2703 or 3804 may be rigid and of fixed length or in a preferred embodiment the connecting bridge 2703 or 3804 is flexible and telescopes to enable independent positioning of the femoral cutters within each tibiofemoral compartment. A telescoping bladder 2705 may be placed under each belt cutter.

Figure 23:
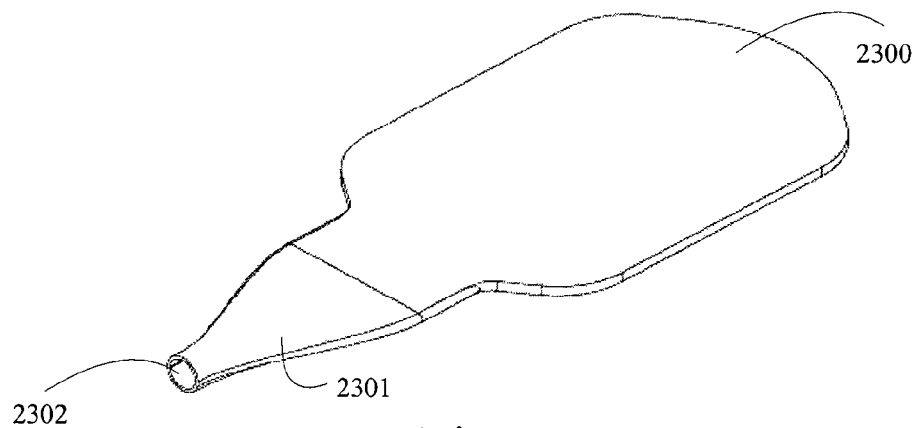
FIG. 23 is perspective view of an expandable telescoping bladder, shown in a collapsed configuration.

FIG. 23 illustrates a bladder, shown in a collapsed form. As described above, it is desirable to extend a femoral cutter once it has been placed in either of the tibiofemoral compartments or in the patellofemoral compartment. In one embodiment a fluid or gas filled bladder is placed under the femoral cutter to extend the bladder—cutter combination within the joint space. A bladder 2300 as shown in FIG. 23 can be made of a suitable material, such as, but not limited to. PET, nylon, polyethylene or urethane. In its collapsed form the bladder 2300 is flat and can be filled via a port 2302 and neck 2301 in one end. Alternately, there may be two ports (not shown) to allow air to bleed from the bladder as fluid is injected into the bladder. The bladder may be compliant to enable expansion in all directions once placed between a femoral cutter and the tibia, or between a femoral cutter and patella. Alternatively, the bladder may be non-compliant to constrain bladder expansion to a designed volume.

In preparing the femoral articular surfaces the femoral cutters may require greater translational stability than what is provided by a free standing bladder. Such stability can be provided by designing a telescoping device within the cutter as described herein, then placing the bladder within this telescoping section. In addition, the bladder may be susceptible to puncture by instruments used in the surgical procedure or by the bony support surface. Hence, it may be desirable to house the bladder in an expandable platform that can be placed between the femoral cutter and the tibia or the patella.

Figure 24:
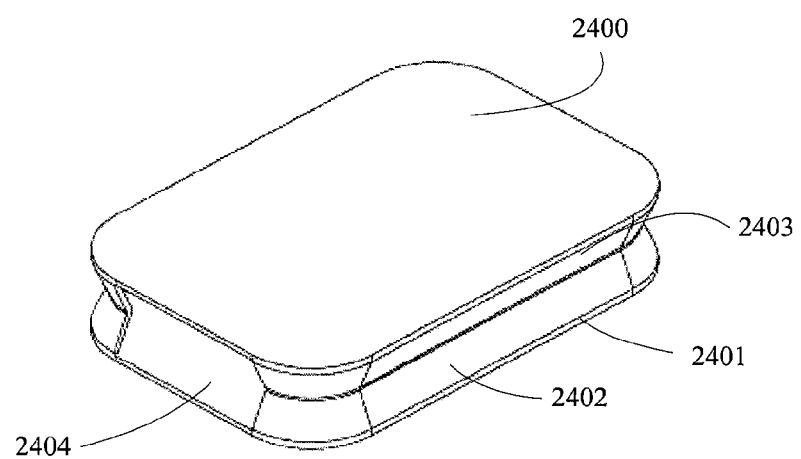
FIG. 24 is a perspective view of an expandable housing, suitable for receiving the bladder of FIG. 23 within.
Figure 25:
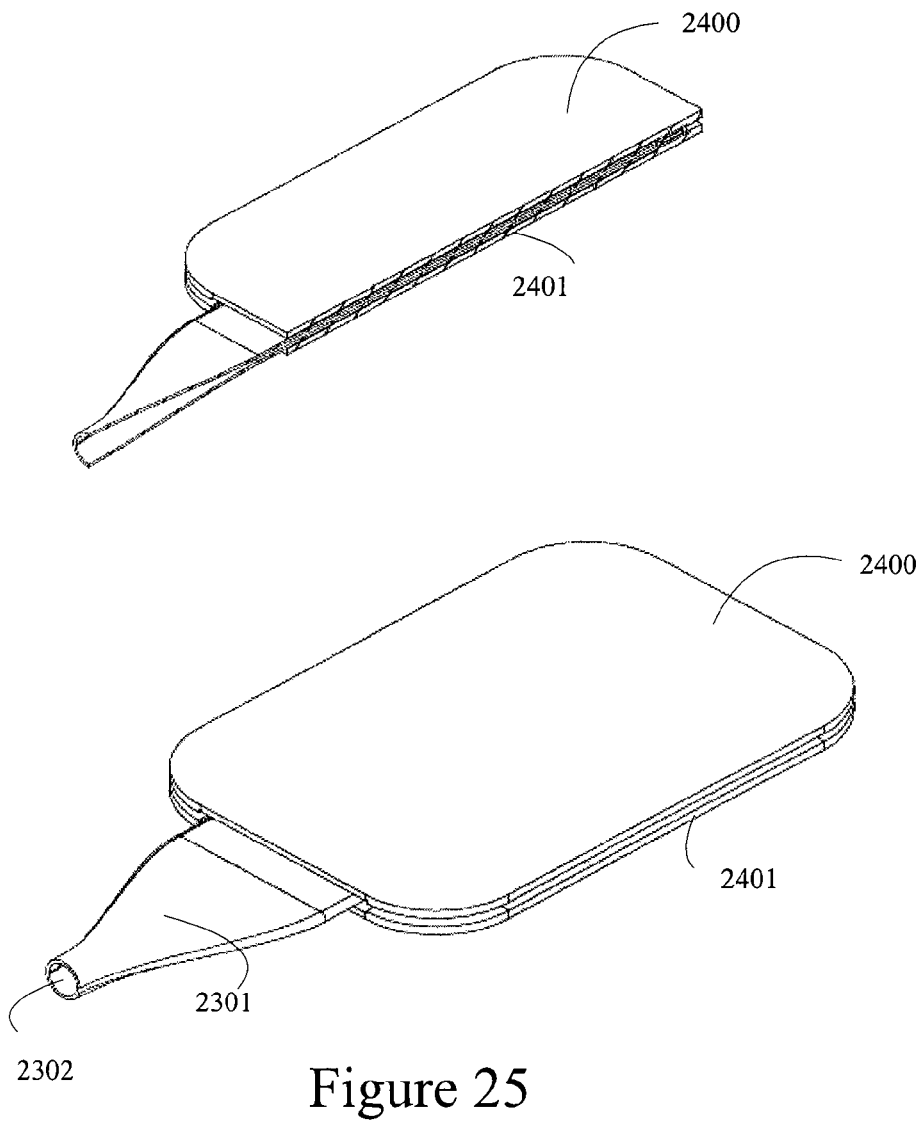
FIG. 25 is a perspective, cutaway view, and a non-cutaway view, of the bladder of FIG. 23 disposed within the platform of FIG. 24, shown in a collapsed configuration.
Figure 26:
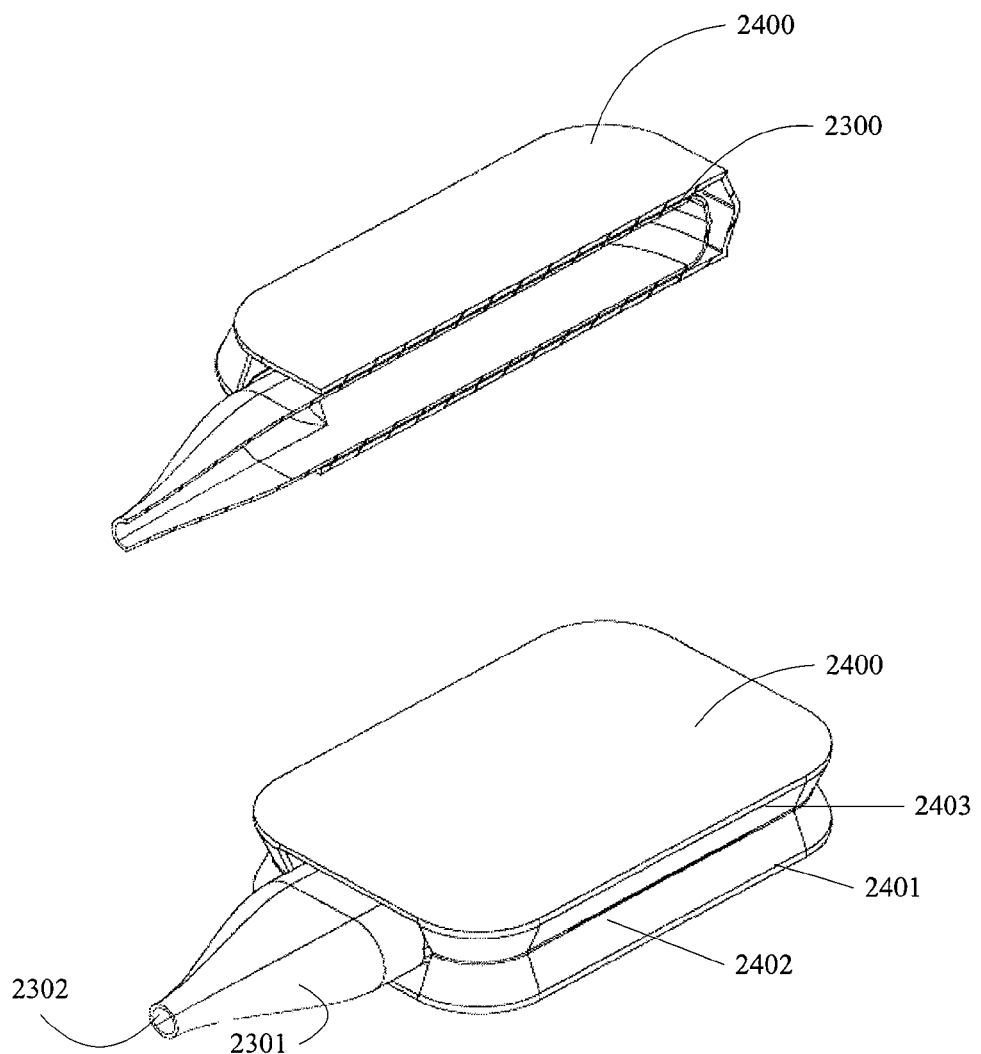
FIG. 26 is a perspective, cutaway view, and a non-cutaway view, of the bladder of FIG. 23 disposed within the platform of FIG. 24, shown in an expanded configuration.

FIGS. 24, 25 and 26 illustrate an expandable housing which may have an expandable bladder housed within. The expandable housing may be fabricated out of metal, plastic or other suitable material. The top plate 2400 and bottom plate 2401 can be rigid or semi-rigid. The sidewalls 2402 and 2403 can fold either in on one another or out on one another to minimize thickness in a collapsed state (see FIG. 25). An opening 2404 is provided for the neck 2301 of the bladder.

FIG. 26 illustrates the housing as the bladder within is filled such that the expandable housing telescopes to a designed height. If filled with sterile saline or other suitable fluid that is incompressible the height of the expandable housing can be incrementally increased or decreased to facilitate appropriate femoral resection. Alternatively, the fluid can be introduced into the bladder 2300 within the expandable housing under pressure control in which case the distraction force within the tibiofemoral or patellofemoral compartment can be controlled to facilitate appropriate femoral resection.

Figure 47:
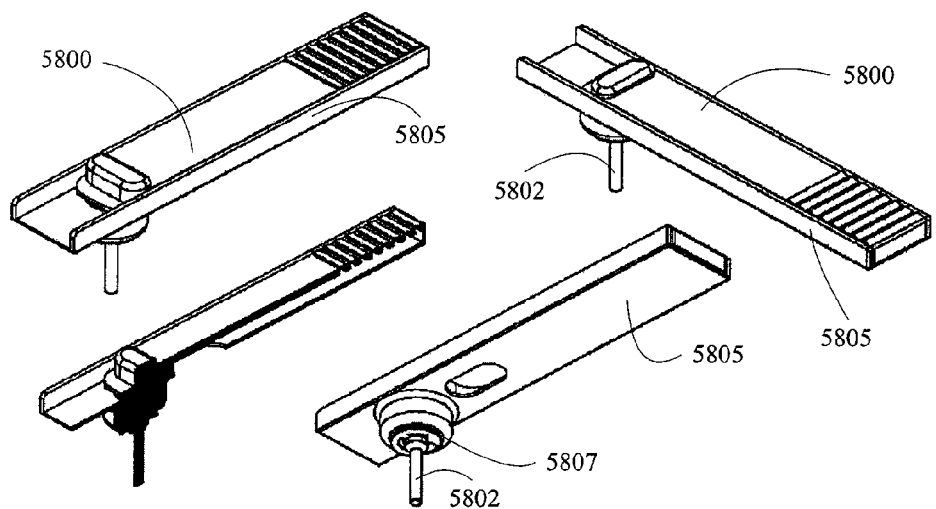
FIG. 47 includes perspective views of a cartridge for use in removing bone.
Figure 48:
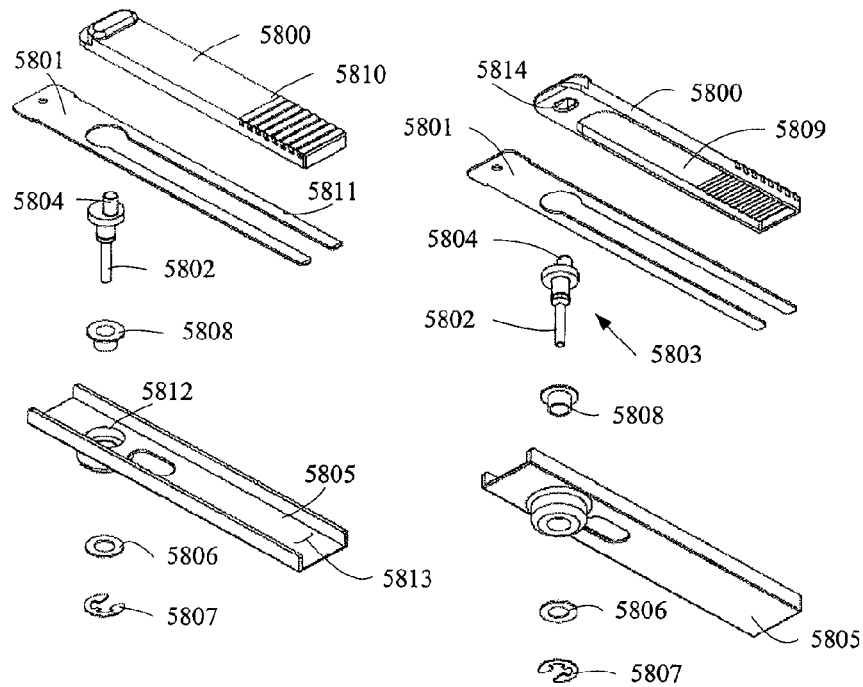
FIG. 48 includes exploded views of the cartridge of FIG. 47.

FIGS. 47 and 48 illustrate a shaver being placed in a tibiofemoral joint and the knee flexed and extended to move the femoral condyle over the cutting elements of the shaver to remove material from the condyle. In another embodiment a reciprocating motion is applied to the shaver to enhance material removal from the condyle while the knee is flexed and extended. As shown in FIGS. 47 and 48, a femoral shaver designed for use in either the medial or lateral tibiofemoral compartments provides a frame 5805 with a flat support surface for support on the prepared tibial plateau. The femoral condyle is sculpted by a not of cutting elements 5810 integral to a cartridge 5800. Alternately, the cutting elements 5810 may be designed as an insert that fits into the cartridge 5800. A rigid or flexible drive shaft extension (not shown) can be attached between the drive shaft 5802 and a rotational power supply such as a surgical power drill or a motor.

A reciprocating motion can be applied to the cartridge 5800 to enhance material removal from the femoral condyle. The cartridge shown is designed to move axially in a channel 5813 within the frame 5805. In one embodiment a drive cam 5803 converts rotational input to the drive shaft 5802 via an off-set cam 5804 spinning in a transverse slot 5814 in the cartridge 5800. The drive cam 5803 is supported in a bearing 5808 placed in a countersunk hole 5812 in the frame 5805 and held in place with a washer 5806 and a retainer 5807.

As material is removed from the femoral condyle it is desirable to increase the height of the shaver accordingly that is to extend the shaver within the tibiofemoral compartment. The cartridge 5800 is free to move vertically in the frame 5805. One or more shims 5801, each having two arms 5811 designed to pass along side the drive cam 5803, can be placed between the cartridge 5800 and frame 5805 to extend the shaver.

Figure 49:
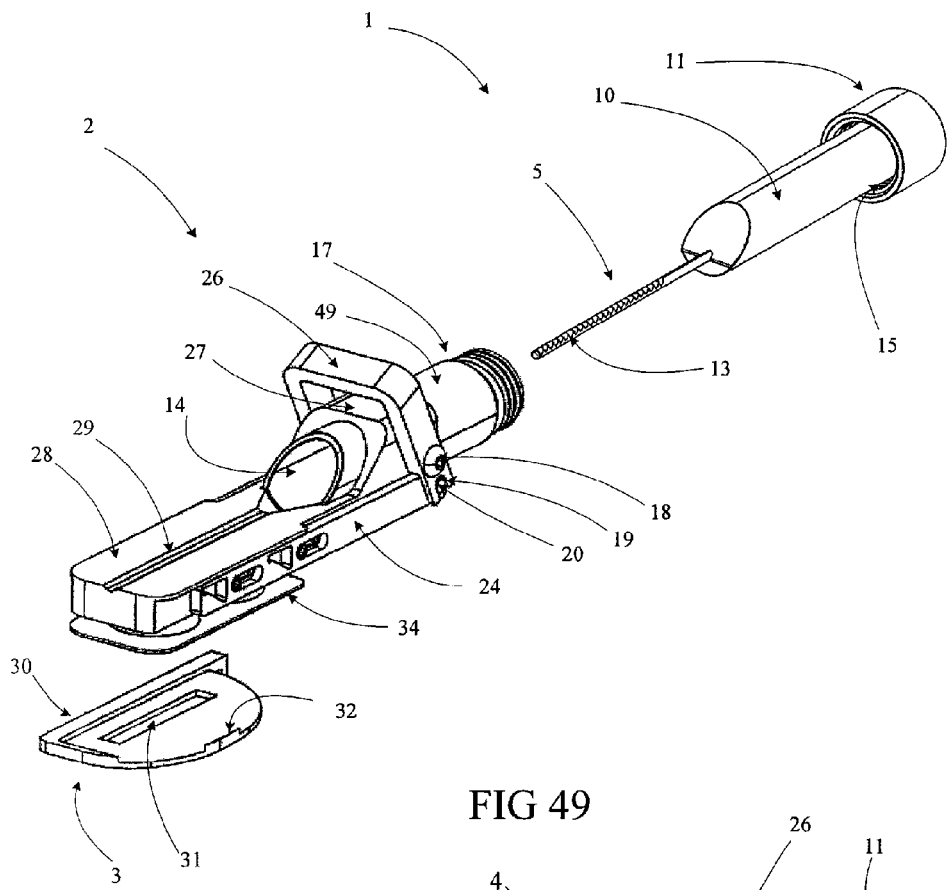
FIG. 49 is an exploded view of a bone scribing instrument showing a serial distractor, a scribing insert with longitudinal rasping element and a tibial trial base.
Figure 51:
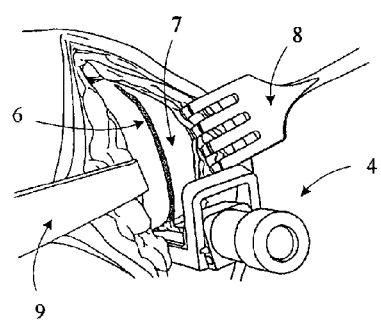
FIG. 51 is an illustration of a surgically exposed knee with the medial femoral condyle visible showing a bone scribing instrument in place and a line scribed into the femoral condyle.
Figure 50:
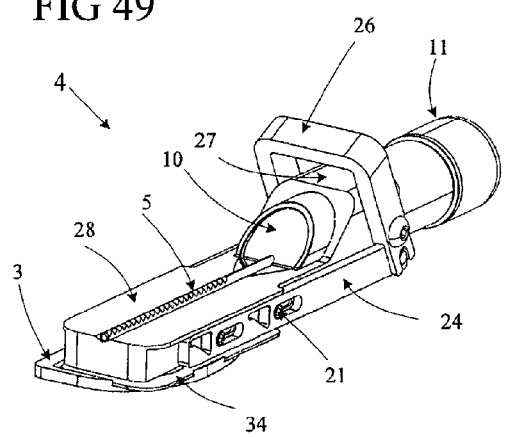
FIG. 50 is a perspective view of a bone scribing instrument assembled with a tibial trial base and the spring loaded distraction platform retracted.

FIGS. 49, 50, 51 and 57 illustrate an instrument, the bone scribe assembly 4 as shown in FIG. 50, to prepare or scribe a guide line in the articular surface of the distal femur. Turning to FIG. 49, such instrument including a bone scribing insert 1, serial distractor 2 and tibial trial base 3. The area of contact between the bony surfaces of the tibiofemoral and patellofemoral compartments move along the surface of the femur, within each compartment, as the knee flexes and extends. After one or both of the tibial plateaus has been resected, the knee is placed in flexion and a tibial trial base 3 and a bone scribe assembly 4 are placed on resected bone surface positioning rasp 5 appropriately along the respective femoral condyle. As the knee is extended, rasp 5 scribes a shallow groove into the femoral condyle indicating the path to be followed by a primary sculpting instrument described below. As illustrated in FIG. 51, the bone scribe assembly 4 scribes a guide line 6 in the surface of the medial femoral condyle 7 to provide the surgeon an indication of guide surface location and implant location before committing to preparing the guide surface, analogous to the adage "measure twice and cut once." Exposure to the surgical site attained by tissue retractors 8 and 9. In similar fashion, a bone scribe assembly (not shown) may be structured for support by a resected patella to prepare a guide line in the femoral trochlea before use of a primary sculpting instrument to prepare a guide surface in the trochlea as described later in this specification.

Figure 57:
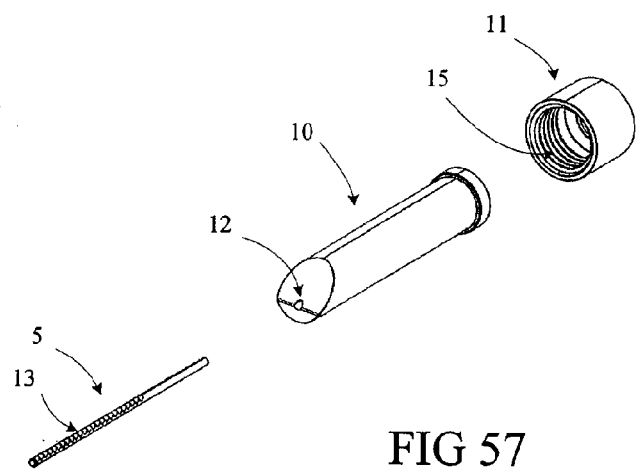
FIG. 57 is an exploded view of the scribing insert of FIG. 49 and FIG. 50.
Figure 58:
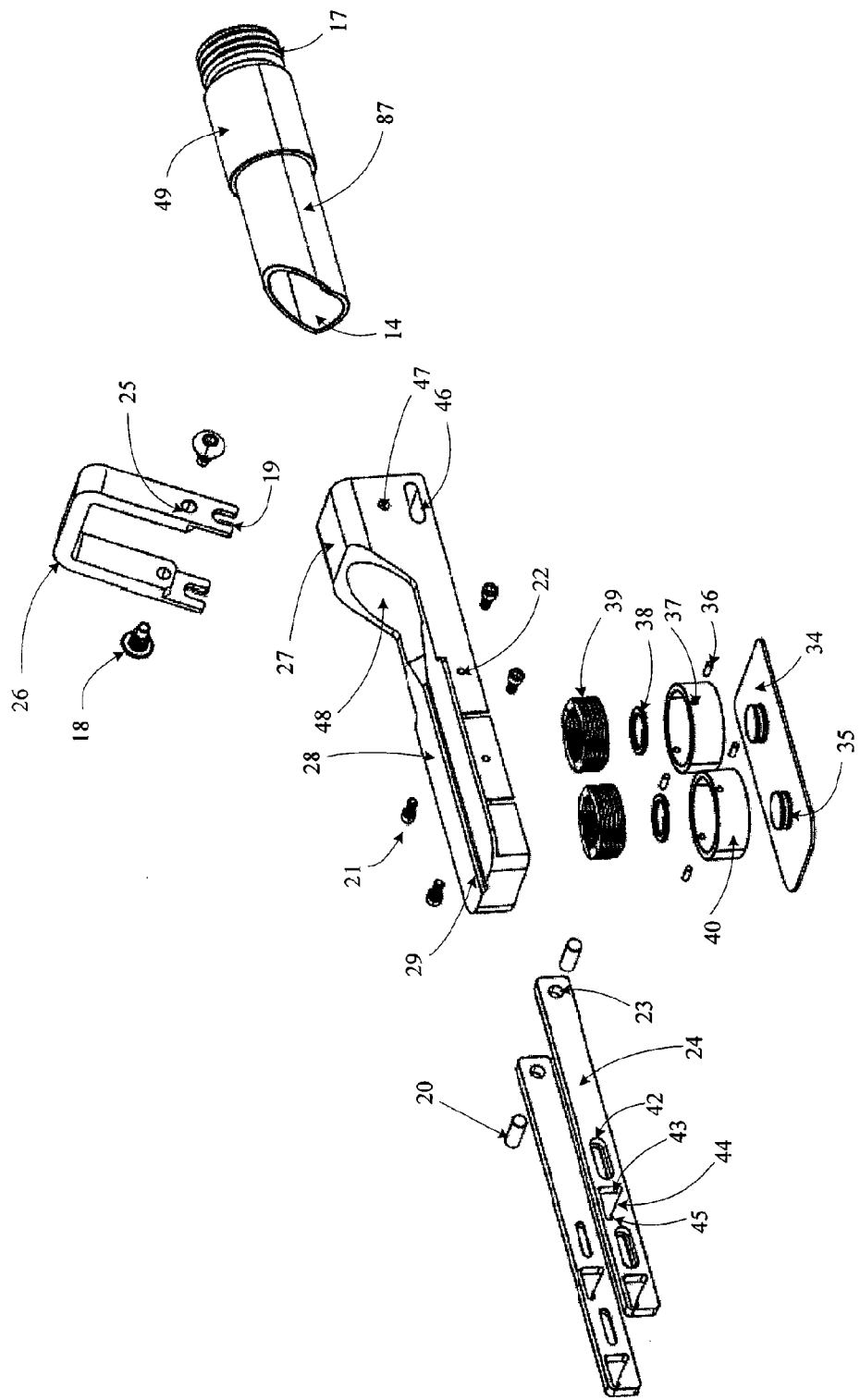
FIG. 58 is an exploded view of the serial distractor shown in FIG. 49, FIG. 50, FIG. 52 and FIG. 53.
Figure 59:
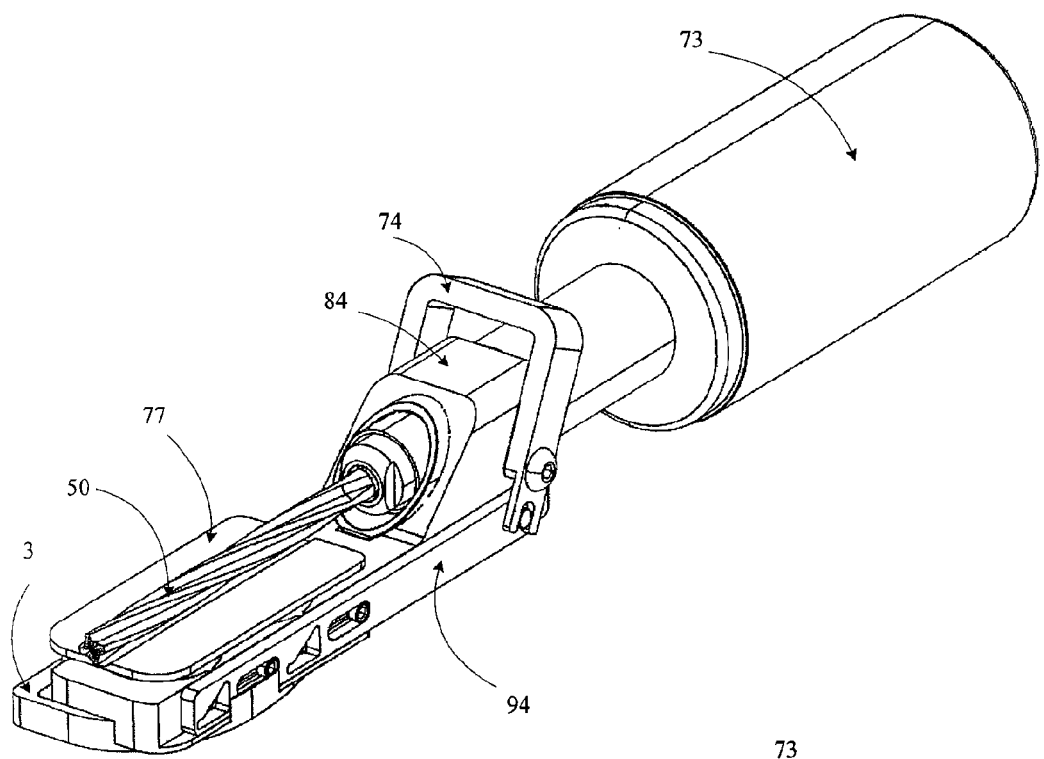
FIG. 59 is a primary sculpting instrument with a parallel distractor and tibial trial base.

The bone scribe insert 1 includes a rasp 5, scribe body 10 and scribe cap 11 as shown in FIGS. 49, 50 and 57. The rasp 5 is slidably received and secured in hole 12. At least one surface of the rasp 5 is serrated 13 to provide a cutting surface to remove cartilage and bone when slid along the surface of an adjacent bone. Scribe body 10 is slidably received in channel 14 of adaptor 49 which is releasably fixed in receiving chamber 48 of serial distractor 2 and secured in place by scribe cap 11 by internal threads 15 engaging with external threads 17 on serial distractor 2. Rasp 5 is longitudinally supported in groove 29 in support face 28. As shown in FIGS. 50, 51 and 58 the bone scribe assembly 4 is placed on the resected tibial plateau between the tibial resection and femoral condyle. The distraction platform 34 is held in a collapsed position when handle 26 is in a forward position, which is towards the patient, thereby moving pin 36 up incline 44 to compress springs 39 and retract cylinders 40 into housing 27. The forward aspect of incline 44 is structured with a flat 45 to lock the distraction platform 34 in a collapsed position. With the bone scribe assembly 4 in position, handle 24 is moved backward releasing distraction platform 34 forcing the rasp 5 against the femoral condyle. Starting with the knee in flexion, the knee is extended sliding the rasp 5 along the surface of the femoral condyle 7 to prepare a shallow groove 6 in the condyle. Groove 6 providing an indication to the surgeon of proper positioning of the serial distractor 2 for subsequent sculpting of the condyle 7.

Referring to FIG. 58, springs 39 provide distraction force in the range of 2 to 20 pounds. Springs 39 are contained in cylinders 40. Bosses 35 extending from distraction platform 34 pass through clearance holes (not shown) in cylinders 40. Retaining rings 38 secure to bosses 35 to fix distraction platform 34 to cylinders 40. Pins 36 retain cylinders 40 by engaging openings 43 in ramp bar 24.

Figure 52:
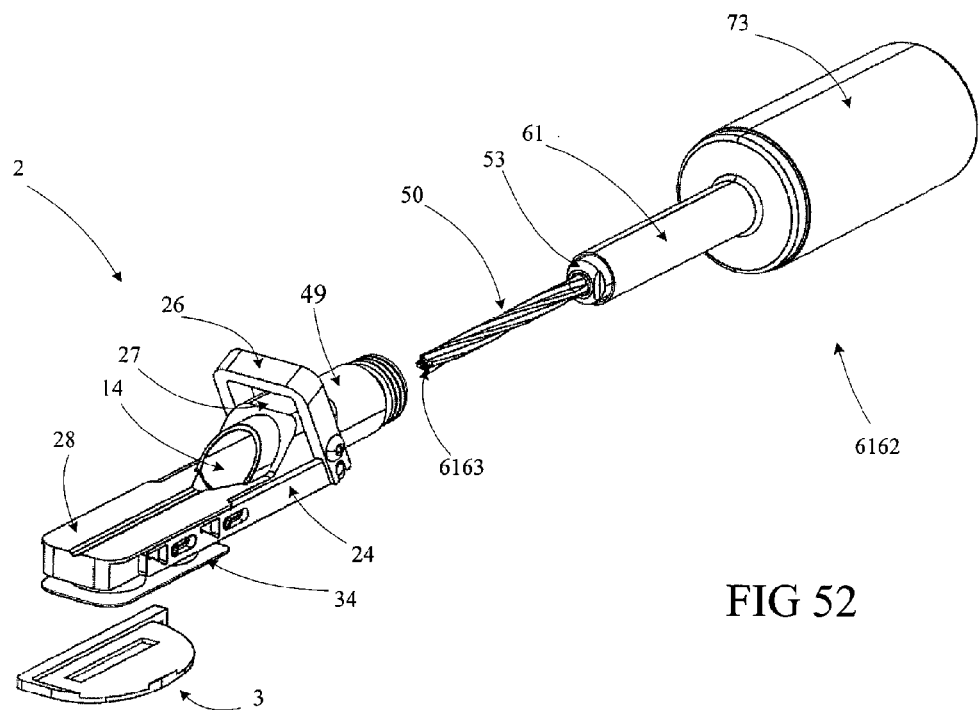
FIG. 52 is an exploded view of a primary sculpting instrument showing a longitudinal sculpting element and a distal spring loaded distraction platform.
Figure 53:
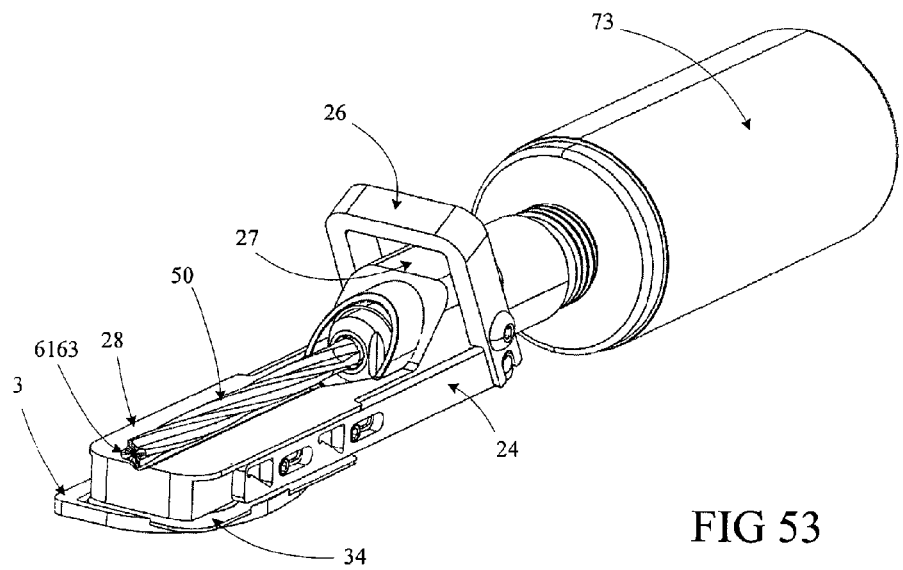
FIG. 53 a perspective view of a primary sculpting instrument of FIG. 52 showing the distal distraction platform retracted.
Figure 55:
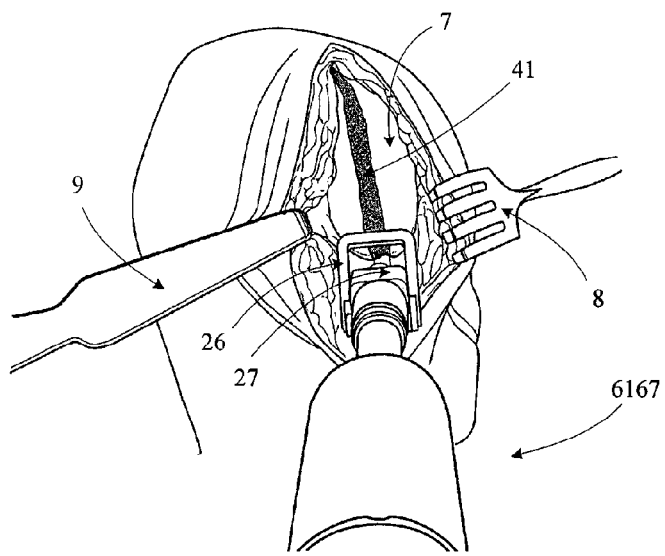
FIG. 55 is an illustration of a surgically exposed knee with the medial femoral condyle visible showing a primary sculpting instrument in place and a prepared guide surface in the medial femoral condyle.

The scribe insert 1 is removed from the serial distractor 2 by unthreading scribe cap 11 from adapter 49 leaving the serial distractor 2 within the tibiofemoral joint space. Referring to FIGS. 52 and 55, the motor sculpting element assembly 6162 is slidably received in adapter 49. The knee is placed in flexion. With the motor running, the forward end 6163 of the sculpting element 50 is advanced into the femoral condyle 7 with the motor sculpting element assembly 6162 releasably fixed to serial distractor 2. As assembled, serial distractor 2 and motor sculpting assembly 162 form one embodiment of the primary sculpting instrument. The primary sculpting instrument is supported by the tibial trial base which in turn is supported by the resected tibial plateau. Alternatively, the primary sculpting instrument is supported directly on the resected tibial plateau. The knee is extended to machine an initial guide surface 41 in the femoral condyle 7 as illustrated in FIG. 55. Such guide surface being of uniform depth from the articular surface of the condyle 7. The motor sculpting element assembly 6162 is released and removed from the serial distractor 2. The serial distractor 2 is collapsed and removed from the tibiofemoral joint.

Figure 54:
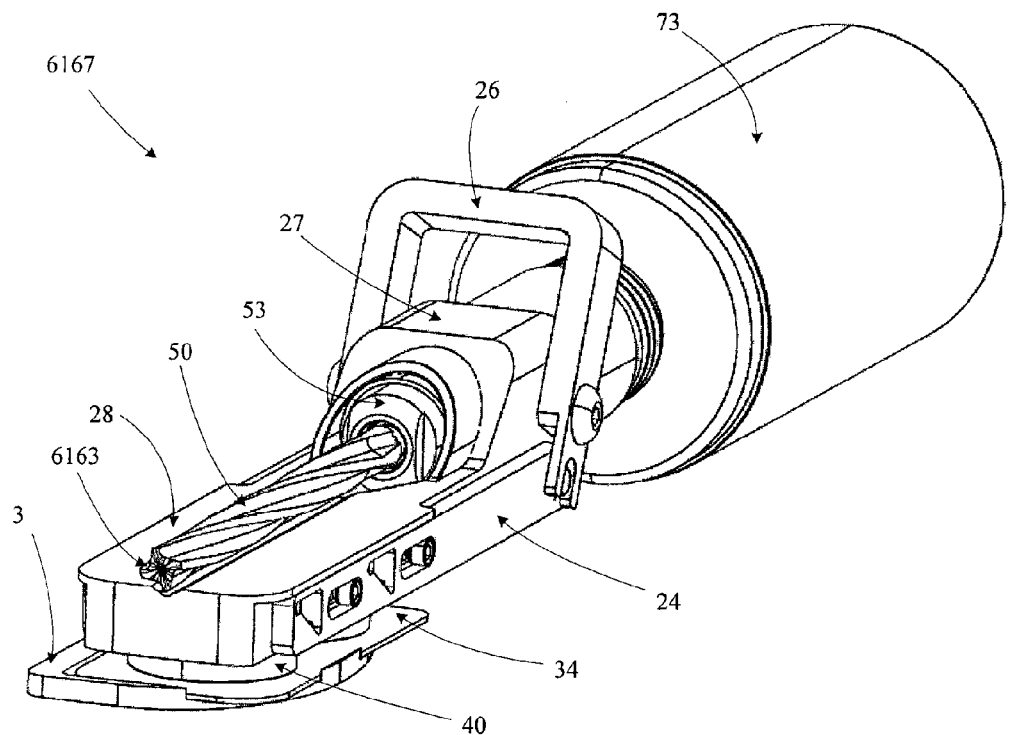
FIG. 54 is a perspective view of the primary sculpting instrument of FIG. 53 showing the distraction platform released and extended.
Figure 60:
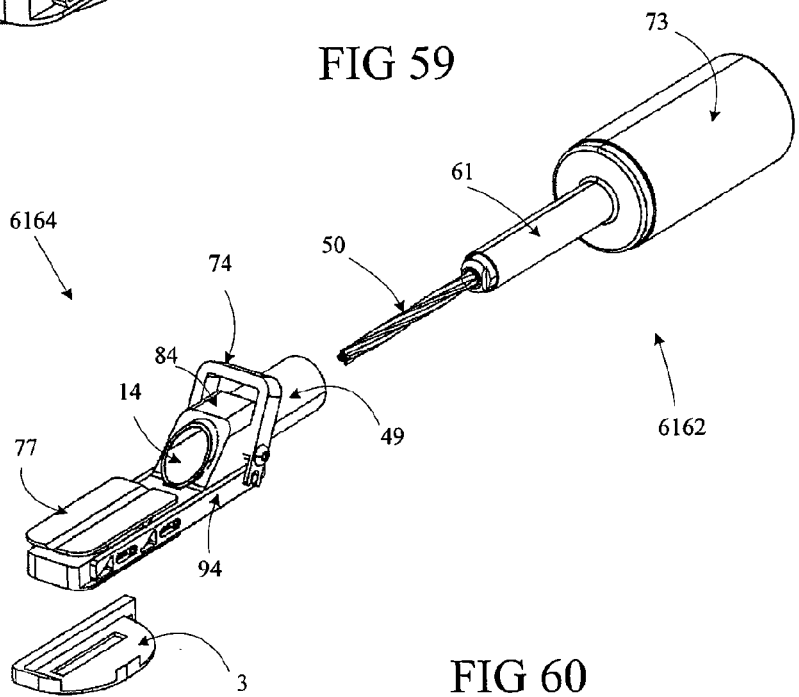
FIG. 60 is an exploded view of the primary sculpting instrument of FIG. 59.
Figure 65:
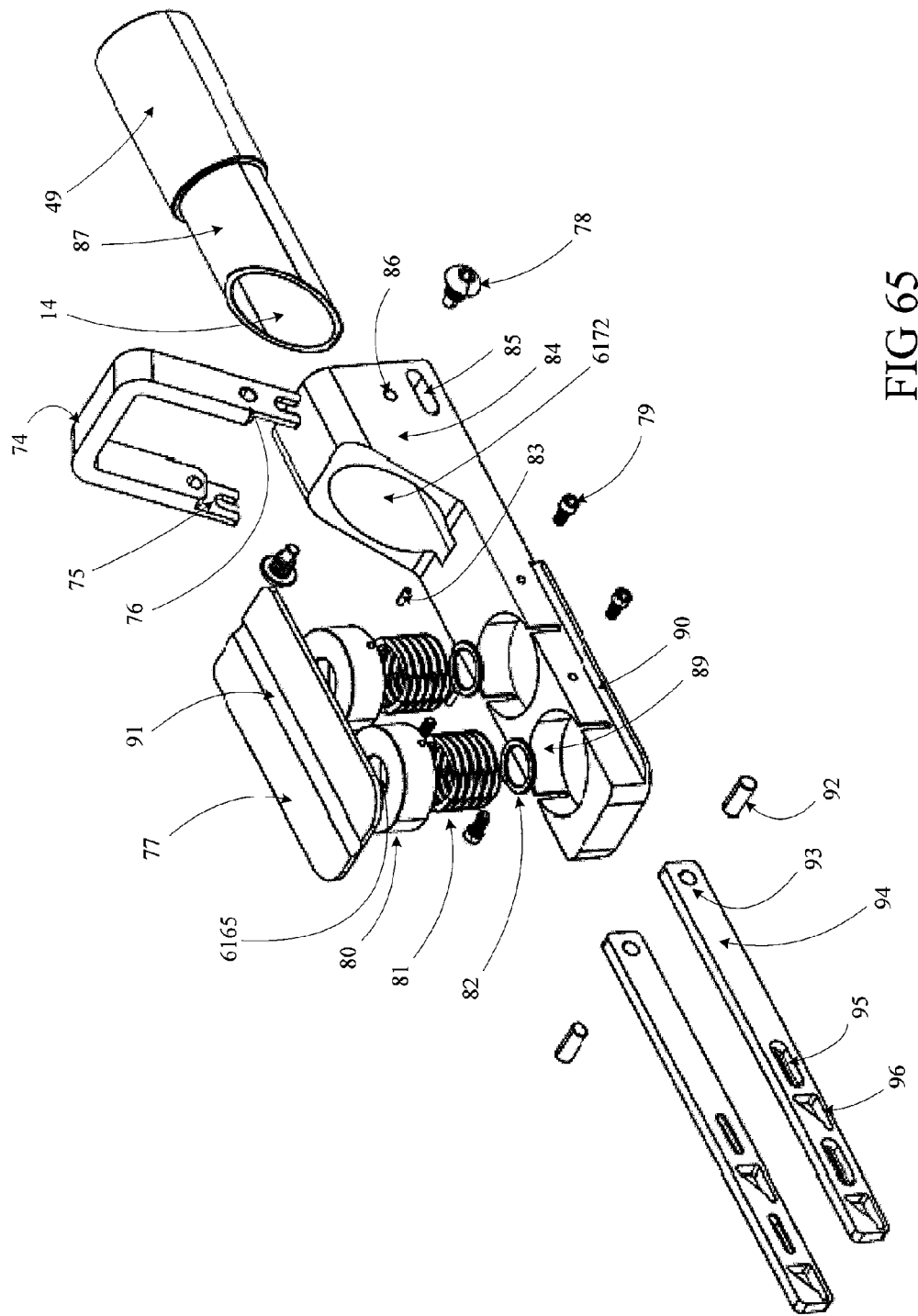
FIG. 65 is an exploded view of the parallel distractor of FIG. 59.

FIG. 54 illustrates one embodiment of a serial distractor 2 assembled with motor sculpting element assembly 1 and tibial trial base 3 in which the distraction platform 34 is supported by the tibial trial base 3. One embodiment of the primary sculpting instrument is formed by the assembled serial distractor 2 and motor sculpting element assembly 1. In this embodiment the primary sculpting instrument distracts the tibiofemoral joint while positioning the sculpting element 50 at a constant depth below the femoral articular surface thereby creating an initial guide surface at a uniform depth below the condyle surface. Such initial surface is deepened and kinematically prepared with another embodiment of the primary sculpting instrument structured with the parallel distractor 164, shown in FIGS. 60 and 65, described below. Alternatively, the secondary sculpting instrument, as described later in the specification, may use the initial guide surface prepared by the primary sculpting instrument structured with the serial distractor 2 to guide preparation of an implant bone support surface in the femoral condyle.

Referring to FIG. 54, handle 26 is in a backward position releasing the distraction platform 34 to apply distraction force between tibial distraction platform 34 and femoral condyle 7 as shown in FIG. 55 in contact with support face 28. Sculpting element 50 is supported releasably secured in collet 55 by clamp nut 53 and drive tube 57. Drive tube 57 is rotatably supported by bearing 59 contained in hole 60 of barrel 61. Barrel 61 is secured to motor 73 with threaded fasteners (not shown) in flange 70 and extending from holes 72 of motor 73. Adaptor 49 is slidably received over barrel 61 of motor sculpting assembly 6162. Adaptor 49 is then passed into receiving chamber 48 of body 27 of serial distractor 2.

Figure 56:
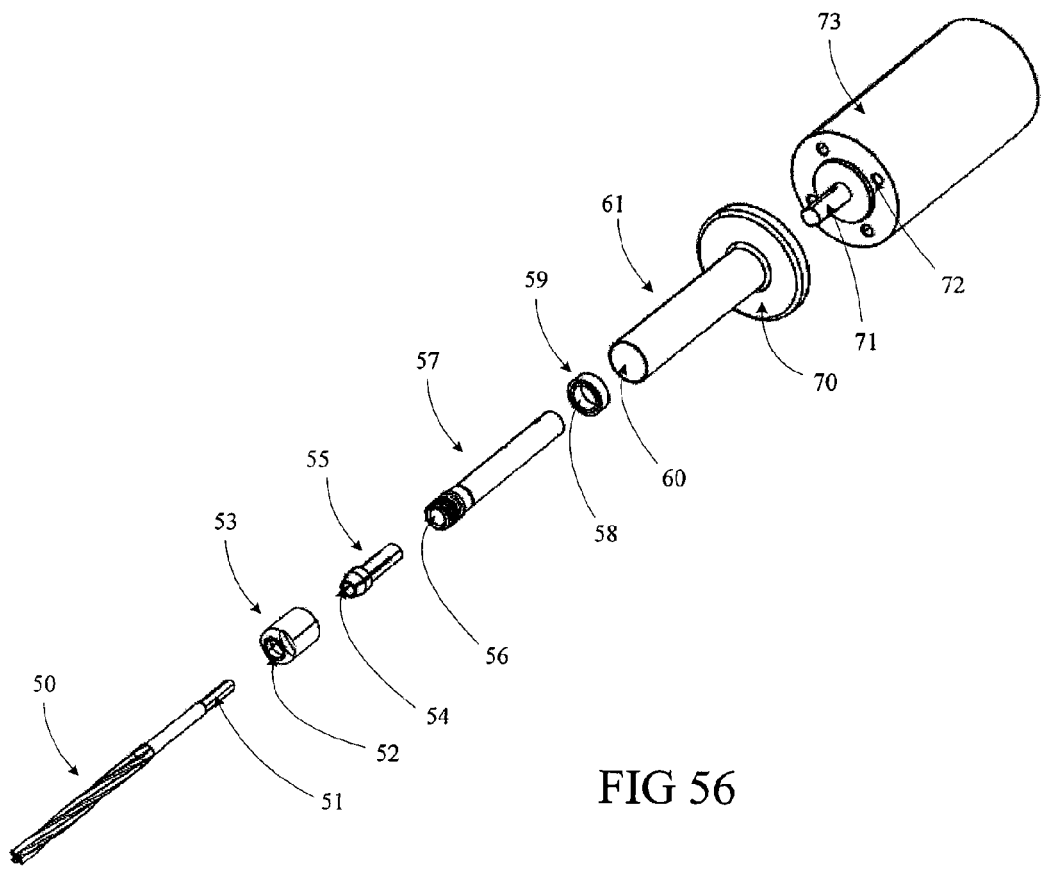
FIG. 56 is an exploded view of a sculpting element and drive motor assembly of the primary sculpting instrument of FIG. 52, FIG. 53, FIG. 54, FIG. 59, FIG. 60, FIG. 61 and FIG. 63, showing a motor, a sculpting element and collet locking mechanism.

Referring to FIG. 56, one embodiment of the motor sculpting element assembly 6162 is assembled by fixing drive tube 57 to drive shaft 71 of motor 73 and attaching flange 70 to threaded holes 72 with threaded fasteners (not shown). Bearing 59 supported in barrel hole 60 supports drive tube 57. Collet 55 is slidably received in drive tube 57 and locked with clamp nut 53 threaded to drive tube 57. Collet 54 releasably clamps sculpting element 50 at hex attachment 51.

In one embodiment, tissue guided surgery is provided by distracting the tibiofemoral joint under load control while sculpting the femoral condyle with a sculpting element at a predetermined distance from the resected tibial plateau. Referring to FIGS. 59 through 64, parallel distractor 6164 applies a distraction force between the resected tibial plateau and femoral condyle. The distraction platform 77 is held in a collapsed position when handle 74 is in a forward position, which is towards the patient, thereby moving pin 83 down incline 97 to compress springs 81 and retract cylinders 80 into housing 84. The forward aspect of incline 97 is structured with a flat 99 to lock the distraction platform 77 in a collapsed position. Springs 81 provide distraction force in the range of 2 to 20 pounds. Springs 81 are contained in cylinders 80. Bosses 98 extending from distraction platform 77 pass through clearance holes 165 in cylinders 80. Retaining rings 82 secure to bosses 98 to fix distraction platform 77 to cylinders 80. Pins 83 retain cylinders 80 by engaging openings 96 in ramp bar 94.

The parallel distractor 6164 is locked in a collapsed position. With the knee in flexion, tibial trial base 3 and parallel distractor 6164 are placed on the resected tibial plateau. Alternatively, parallel distractor 6162 is placed directly on resected tibial plateau. The parallel distractor 6164 is unlocked by rotating handle 74 backward, away from the patient, to apply distraction force between the tibia and femur. Barrel 61 of motor sculpting assembly 162 is slidably received in channel 14 of adaptor 49 and is releasably fixed therein. The motor sculpting element assembly 6162 is aligned with the initial guide surface previously prepared in the femoral condyle and the sculpting element 50 is advanced into the femoral condyle. Adaptor 49 is slidably received in receiving chamber 6172 of body 84 and is releasably fixed therein. The assembled parallel distractor 6164 and motor sculpting element assembly 6162 is another embodiment of the primary sculpting instrument of the current invention. The knee is extended. The parallel distractor 6164 maintains tibiofemoral distraction force, thereby providing load control of distraction, during knee extension while supporting the sculpting element 50 at a predetermined distance from the resected tibial plateau. With a dynamic distraction force applied between the tibia and femur, knee kinematics as determined by the anterior and posterior cruciate ligaments, the medial and lateral collateral ligaments and soft tissue structures spanning the knee, guide the separation between the tibia and femur throughout range of motion. The sculpting element 50 at a fixed distance from the resected tibial plateau prepares a guide surface according to the patient's knee kinematics.

Referring to FIGS. 61 through 65, the primary sculpting instrument embodiment formed by the assembly of parallel distractor 6164 and motor sculpting assembly 6162 is structured for collapsing the parallel distractor 6164 by rotating handle 74 forward, as illustrated in FIGS. 61 and 62, to slide ramp bar 94 backward thereby sliding pin 83 along ramp 97 in hole 6168 to urge distraction platform 77 towards body 84 and compress springs 81. Lock 99, as shown in FIG. 63, at the end of ramp 97 locks pin 83 with the distraction platform 77 in a collapsed position.

Referring to FIGS. 63 and 64, handle 74 moved backwards unlocks pin 83 from lock 99 allowing distraction platform 77 to apply load to femoral condyle, such load reacted between the bottom of body 84 and tibial trial base 3 supported on resected tibial plateau. Alternatively, body 84 may be supported directly on resected tibial plateau.

Figure 66:
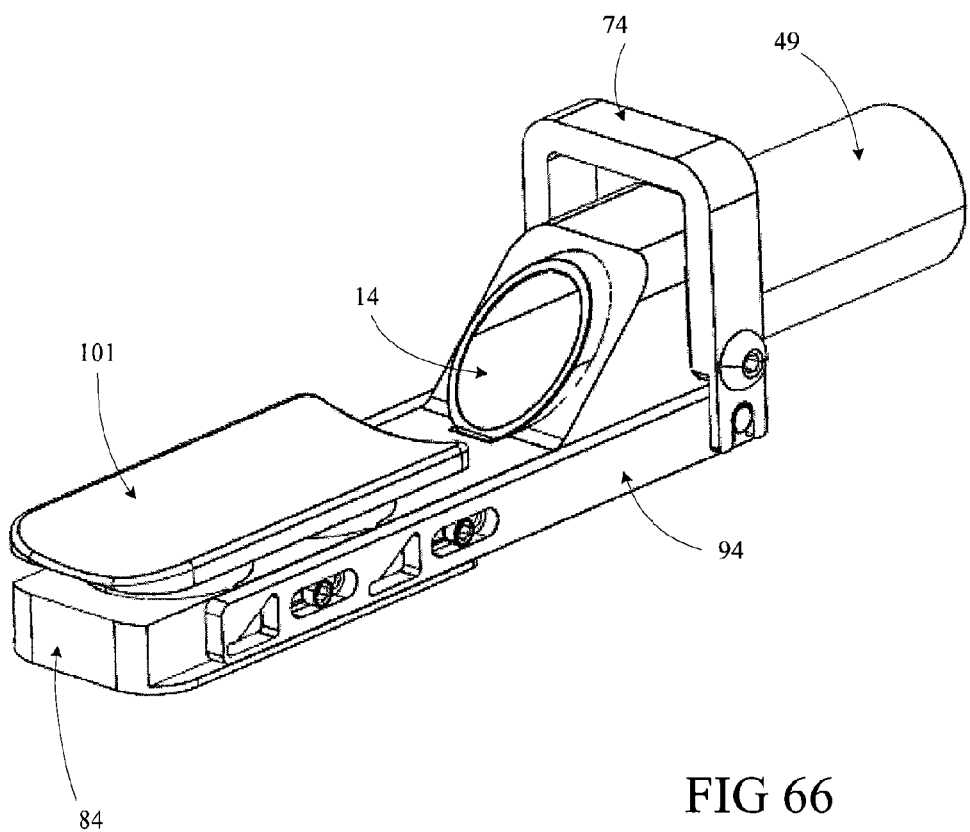
FIG. 66 is a perspective view of another embodiment of a parallel distractor showing a dished distraction platform for use in a primary sculpting instrument.

The secondary sculpting instrument references the guide surface to prepare an implant support surface in the femoral condyle at a predetermined distance from the guide surface as described below. The distraction platform 77 may be planar. Alternatively, as shown in FIG. 66, the distraction platform 6101 may be contoured as a cylinder to guide the femoral condyle centrally on the sculpting element (not shown). Alternatively, the distraction platform may be concave or dished to further capture the femoral condyle to guide the femoral condyle in a generally central location over the sculpting element.

Figures 67, 68:
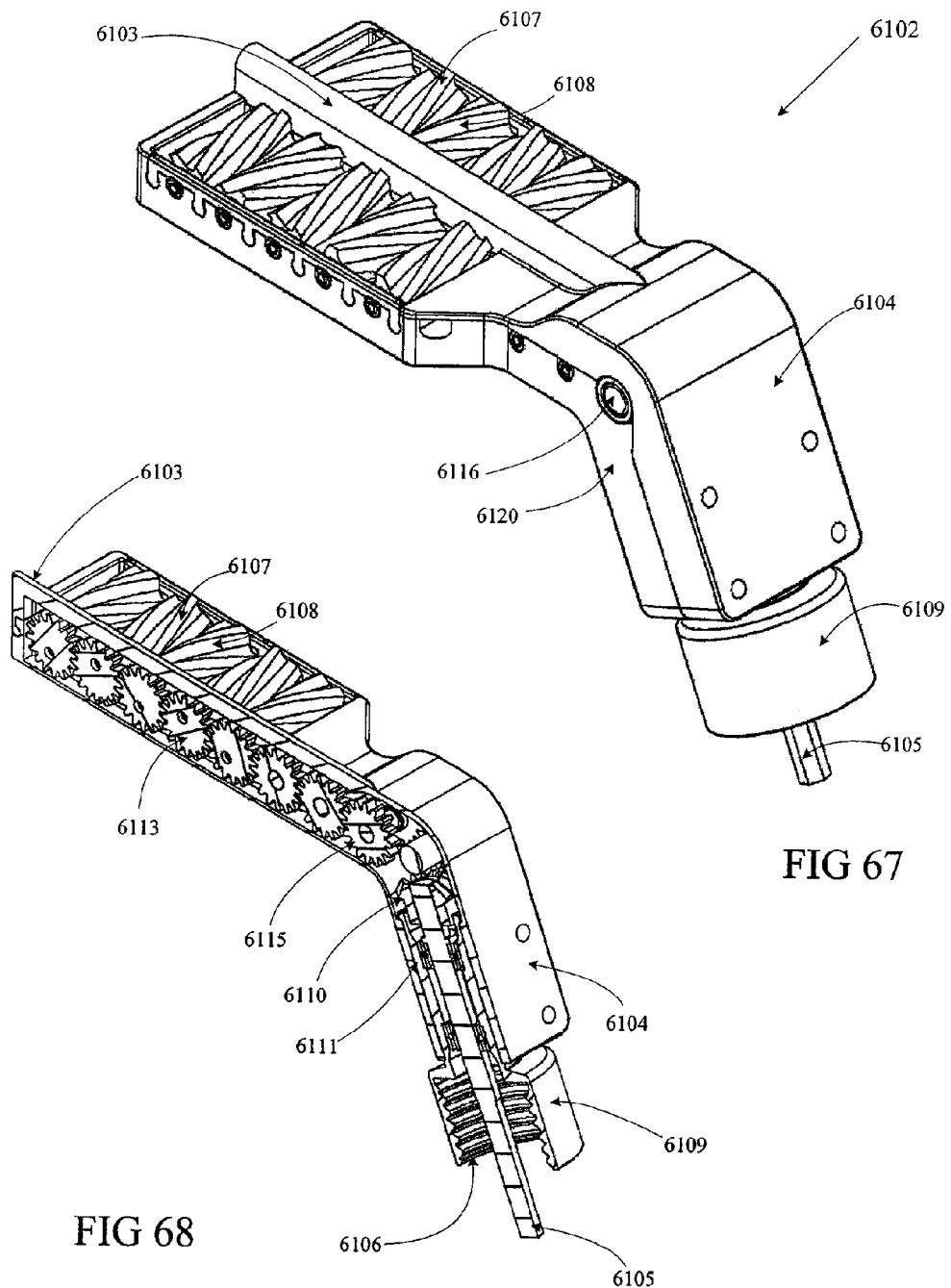
FIG. 67 is a perspective view of a secondary sculpting instrument showing barrel sculpting elements with adjacent sculpting elements rotating in opposite directions.
FIG. 68 is cross sectional view of the secondary sculpting instrument of FIG. 67 taken along the center of the guide element showing a spline gear drive train of the secondary sculpting instrument.
Figure 69:
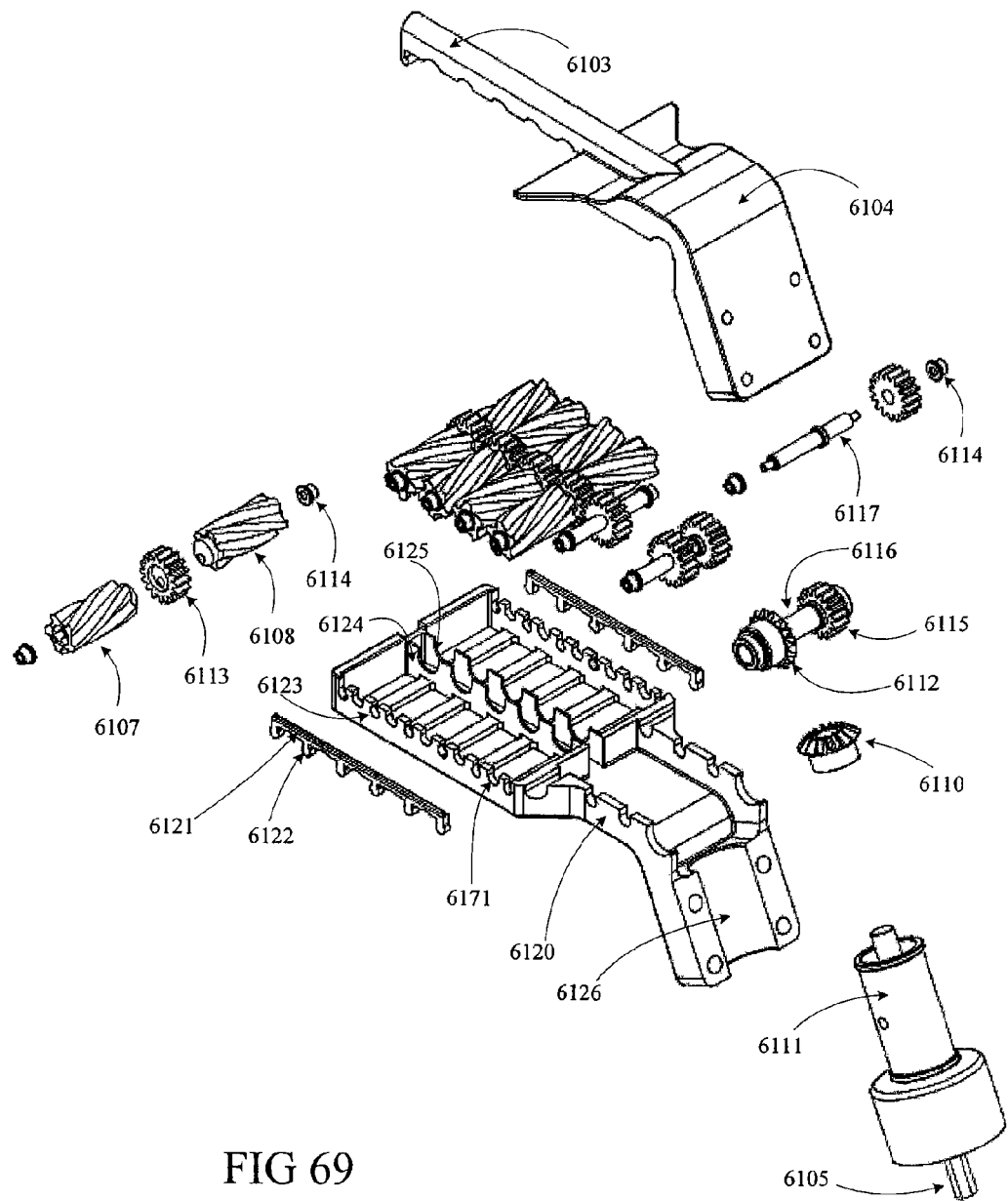
FIG. 69 is an exploded view of the secondary sculpting instrument of FIG. 67.

FIGS. 67, 68 and 69 illustrate one embodiment of the secondary sculpting instrument 6102 in which cutting elements 6107 and 6108 are supported by base 6120 and cover 6104. One or more cutting elements 6107 or 6108 are driven by spline gears 6113 supported between flanges 6124 in slots 6125. Torque is applied by a motor (not shown) releasably connected to adaptor 6109 by threaded interface 6106 and to driveshaft 6105. Driveshaft 6105 is assembled to bevel gear 6110 which meshes with bevel gear 6112 to transfer torque via shaft 6116 to spline gear 6115. Bushings 6114 provide wear resistance at shaft 6117 and 6116 base 6120 and cover 6104 interfaces. The drive train formed by spline gears 6113 rotate adjacent cutting elements 6107 and 6108 in opposite directions. Alternatively, idler spline gears (not shown) may be used between spline gears 6113 to rotate adjacent cutting elements 6107 and 6108 in the same direction. Cover 6104 is structured to form guide element 6103 which is structured to capture spline gears 6113 and cutting elements 6107 and 6108 between flanges 6124 within slots 6125.

Figure 70:
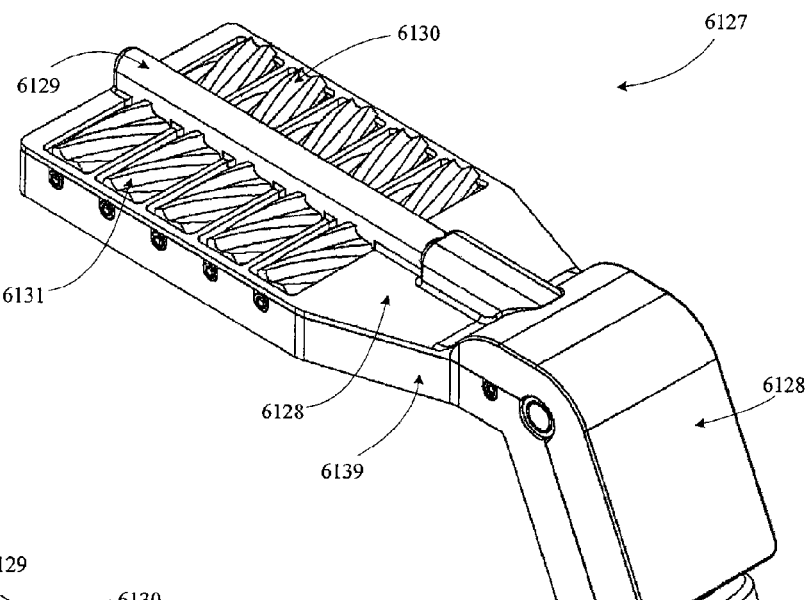
FIG. 70 is a perspective view of another embodiment of a secondary sculpting instrument showing barrel sculpting elements with adjacent sculpting elements rotating in the same direction.
Figure 71:
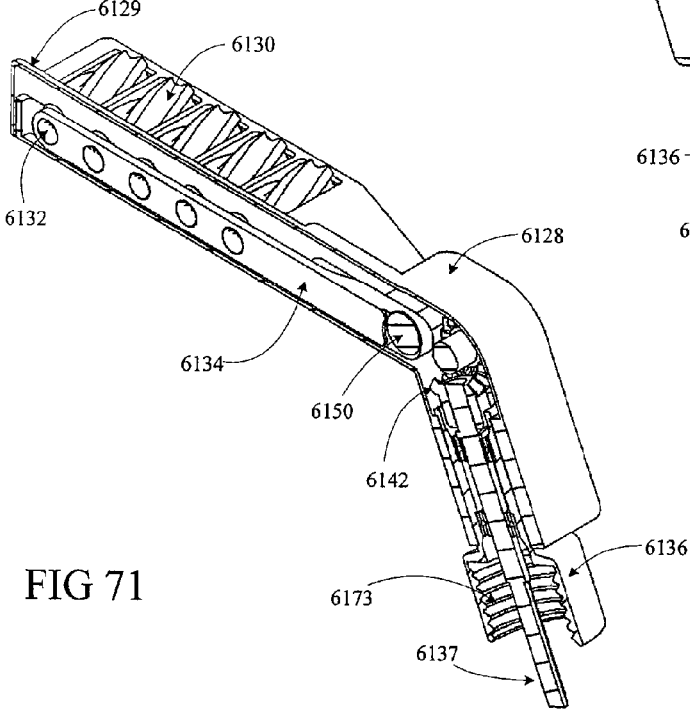
FIG. 71 is cross sectional view of the secondary sculpting instrument of FIG. 70 taken along the center of the guide element showing a crankshaft and connecting arm drive train of the secondary sculpting instrument.
Figures 72, 73:
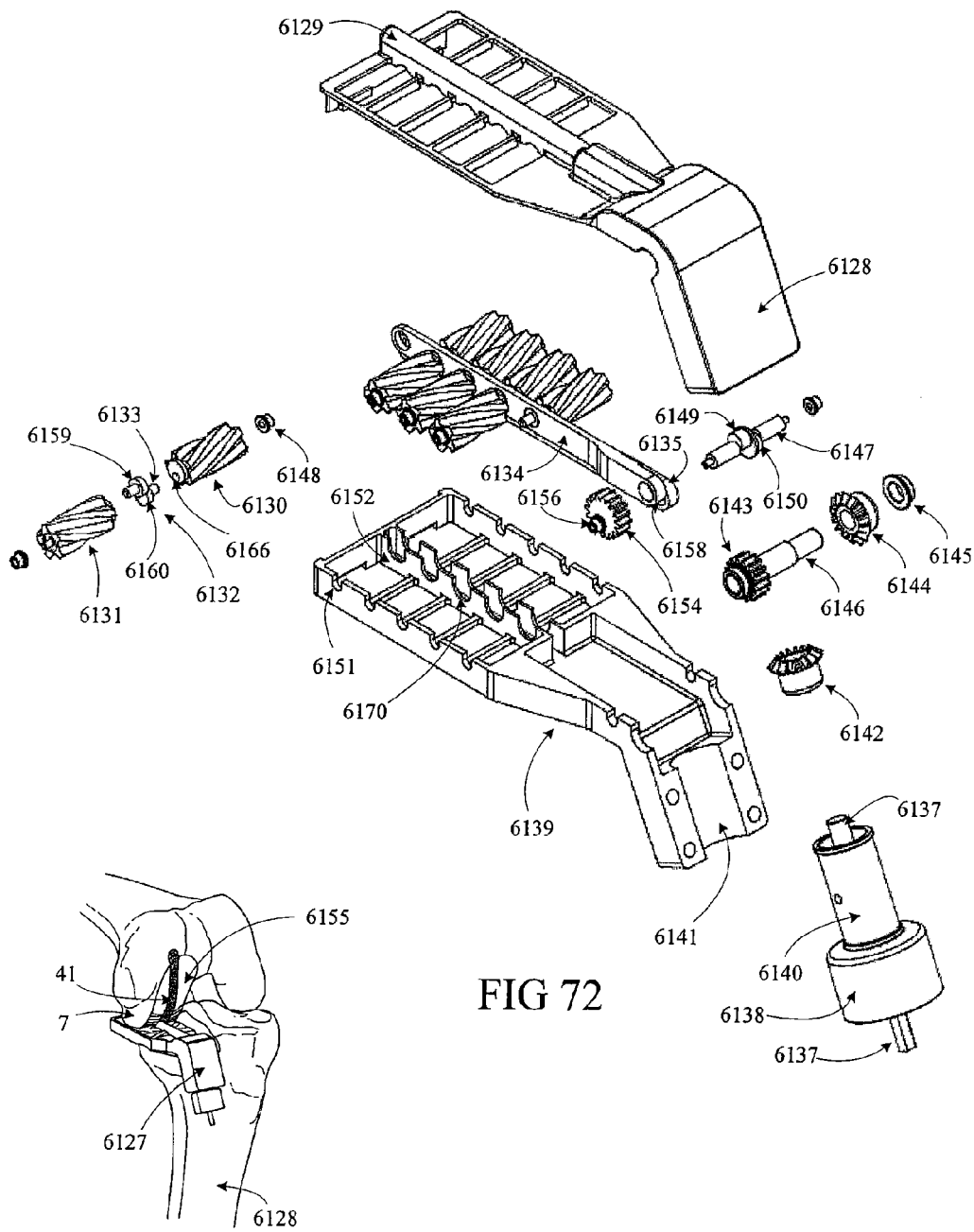
FIG. 72 is an exploded view of the secondary sculpting instrument of FIG. 71.
FIG. 73 is an illustration of a surgically exposed knee with the medial femoral condyle visible showing a secondary sculpting instrument in place and a prepared implant support surface in the medial femoral condyle.

Another embodiment of the secondary sculpting instrument is illustrated in FIGS. 70, 71 and 72 in which cutting elements 6130 and 6131 are supported by base 6139 and cover 6128. One or more cutting elements 6130 or 6131 are driven by connecting bars 6134 and 6135 supported between flanges 6152 in slots 6170. Torque is applied by a motor (not shown) releasably connected to adaptor 6136 by threaded interface 6173 and to driveshaft 6137. Driveshaft 6137 is assembled to bevel gear 6142 which meshes with bevel gear 6144 to transfer torque via shaft 6146 to spline gear 6143. Spline gear 6143 meshes with spline gear 6154 which assembles with crankshaft 6147. Crankshaft 6147 is structured with two cams 6149 and 6150. Cam 6149 is slidably received in hole 6169 in first connecting bar 6134. Can 6150 is slidably received in second connecting bar 6135. Rotation of crankshaft 6147 drives connecting bars 6134 and 6135 to transfer torque to one or more cutting elements 6130 or 6131 through crank 6132. Crank 6132 is structured with two cams 6159 and 6160 orientated to synchronize with crankshaft 6147 cams 6149 and 6150, respectively. Crank 6132 is structured with bosses 6133 that are slidably received by cutting elements 6130 and 6131 to transfer torque to cutting elements 6130 and 6131. Bushings 6145 and 6148 provide wear resistance at shaft 6146 and crankshaft 6147 to base 6120 and cover 6104 interfaces. The drive train formed by two connecting arms 6134 and 6135 rotate two or more cutting elements 6130 and 6131 in the same direction. Cover 6128 is structured to form guide element 6129 which is structured to capture connecting arms 6134 and 6135 and cutting elements 6130 and 6131 between flanges 6152 within slots 6170.

FIG. 73 illustrates the secondary sculpting instrument supported on a resected tibial plateau of tibia 6128 with guide element 6129 slidably received in guide surface 41 previously prepared by primary sculpting instrument described above. Secondary sculpting instrument preparing implant bone support surface 6155 by flexing and extending the knee. Alternatively, the secondary sculpting instrument may be structured to include or work with each embodiment of distraction apparatus described herein. Numerous embodiments of the primary sculpting instrument may be structured by incorporating each embodiment of distraction apparatus described herein. Numerous embodiments of the primary and secondary sculpting instruments may be structured by incorporating combinations of each of the sculpting elements or cutter elements and drive mechanisms described herein.

The description above is provided in order to illustrate various examples and embodiments of the invention and is not an exhaustive list of all combinations and variations of the present invention. It should be understood that various changes, adaptations and modifications may be made therein without departing from the spirit of the invention and the scope of the appended claims. The scope of the invention is provided in the claims which follow.

What is claimed is:

1. A bone sculpting apparatus comprising:
    at least one distraction element, the distraction element including
        an elongate body having first and second ends, a top face and a bottom face, at least one extendable body slidingly receivable in the top face, the extendable body having a first configuration and a second configuration, the second end of said elongate body including a receiving chamber therewithin;
        an adaptor including a first end received into the receiving chamber, a second threaded end, and an adaptor receiving channel disposed therewithin;
        a first bone sculpting tool having first and second ends, the first end including a barrel slidably received into the adaptor receiving channel, the barrel including a sculpting element releasably clamped therein;
    wherein the extendable body is further away from the bottom face in the second configuration than in the first configuration and the first bone sculpting tool is releasably fixed within said receiving channel and positioned at a predetermined distance from the bottom face; and further wherein movement of the extendable body from the first configuration to the second configuration is transverse to an axis of rotation of the sculpting tool.

2. The apparatus of claim 1 wherein the extendable body is spring-loaded, hydraulically powered, or comprises a scissors mechanism.

3. The apparatus of claim 1 wherein said first bone sculpting tool further comprises:
   a. a motor including a drive shaft;
   b. a drive tube engageable with the drive shaft;
   c. a collet slidably received in said drive tube; and
   d. a sculpting element engageable with said collett,
wherein said first bone sculpting tool is configured to prepare a guide surface on a first bone.

4. The apparatus of claim 1 further comprising a second bone sculpting tool interchangeable with said first bone sculpting tool, said second bone sculpting tool receivable within said adaptor receiving channel, said second bone sculpting tool including:
   a base;
   a drive shaft operably connected to said base;
   a plurality of spline gears operably connected to said drive shaft for receiving torque from said drive shaft; and
   a plurality of cutting elements connected to said spline gears and rotatable by said spline gears when torque is applied.

5. The apparatus of claim 4 wherein said plurality of cutting elements are positioned on opposite sides of a guide element.

6. The apparatus of claim 5 wherein said guide element is received in a guide surface on a first bone prepared by the bone sculpting tool.

7. The apparatus of claim 1 wherein the predetermined distance of the bone sculpting tool from the bottom face is adjustable.

8. The apparatus of claim 1 further including a closed-loop control system.

9. The apparatus of claim 8 wherein the closed-loop control system operates under displacement control, load control or combinations thereof.

10. The apparatus of claim 3 wherein the first bone sculpting tool in integrally formed with the distraction element.

11. The apparatus of claim 1 further comprising a guide element structured to be slidably received in the first bone guide surface.

12. The apparatus of claim 11 wherein the bone sculpting tool is integrally formed with said distraction element.

13. The apparatus of claim 4 wherein the bone sculpting tool is integrally formed with the distraction element.

14. The apparatus of claim 1 wherein said at least one distraction element further comprises
   at least one sensor selected from the group consisting of a load sensor operable to measure force across the distraction element, a displacement sensor to measure change in height of the distraction element, and combinations of the foregoing.

15. The apparatus of claim 14 further comprising
   a surgical navigation apparatus configured to measure a motion of the first bone, the second bone or the first and second bones.

16. An apparatus comprising:
   at least one distraction element of claim 1 or 2;
   at least one sculpting element adjustably configured on the distraction element; and
   at least one channel programmable closed loop controller using at least one of a load signal from load sensors, a displacement signal from displacement sensors, a movement signal from surgical navigation, or a combination thereof, to guide said sculpting element in cutting bone.

17. The apparatus of claim 1 wherein the first configuration of the extendable body is a collapsed position and the second configuration of the extendable body is a released position.

18. The apparatus of claim 17 wherein said at least one distraction element further comprises a handle in operable engagement with the extendable body, said handle positionable between a first position in which the extendable body is in said first collapsed position and a second position in which the extendable body is in said released position.

19. An apparatus comprising:
   at least one distraction element, the distraction element including an elongate body having first and second ends, a top face and a bottom face, at least one extendable body slidingly receivable in the top face, the extendable body having a first configuration and a second configuration, the second end of said elongate body including a receiving chamber therewithin;
   an adaptor including a first end received into the receiving chamber, a second threaded end, and an adaptor receiving channel disposed therewithin;
   a scribing instrument releasably fixed within said adaptor receiving channel, the scribing instrument including a rasp, a scribe body having an opening for receiving and securing the rasp, and a cap engageable with said adaptor second threaded end for securing said scribing instrument to said adaptor;
wherein the extendable body is further away from the bottom face in the second configuration than in the first configuration; and further wherein movement of the extendable body from the first configuration to the second configuration is transverse to an axis of rotation of the scribing instrument.

20. The apparatus of claim 19 wherein said extendable body has a top face and a longitudinal groove therein and said rasp is operably received in the longitudinal groove.

21. The apparatus of claim 19 wherein at least one side of said rasp is serrated.

22. The apparatus of claim 21 wherein said rasp is forced against a first bone when said extendable body is released towards the second configuration.

23. The apparatus of claim 19 wherein the elongated body top face has a longitudinal groove therein and said rasp is operably received in the longitudinal groove.

* * * * *

UNITED STATES PATENT AND TRADEMARK OFFICE
CERTIFICATE OF CORRECTION

| | | |
|---|---|---|
| PATENT NO. | : 8,425,516 B2 | Page 1 of 1 |
| APPLICATION NO. | : 12/594389 | |
| DATED | : April 23, 2013 | |
| INVENTOR(S) | : Wesley D. Johnson et al. | |

It is certified that error appears in the above-identified patent and that said Letters Patent is hereby corrected as shown below:

Title Page, item (75) Inventors: replace "Kevin T. Stables", with --Kevin T. Staples--

In the Specifications:

Column 4, Line 58, after "resection", replace "." with --,--

Column 7, Line 57, replace "TGG", with --TGS--

Column 12, Line 43, after "element", replace "out" with --cuts--

Column 24, Line 60, after "along", replace "out" with --cut--

Column 27, Line 43, after "limited to", replace "." with --,--

Column 28, Line 24, after "sculpted by a", replace "not" with --set--

Signed and Sealed this
Eleventh Day of June, 2013

Teresa Stanek Rea
*Acting Director of the United States Patent and Trademark Office*